United States Patent
Epstein et al.

(10) Patent No.: US 6,784,184 B2
(45) Date of Patent: Aug. 31, 2004

(54) 5-(ARYLSULFONYL)-,5-(ARYLSULFINYL), AND 5-(ARYLSULFANYL)-THIAZOLIDINE-2,4-DIONES USEFUL FOR INHIBITION OF FARNESYL-PROTEIN TRANSFERASE

(75) Inventors: Joseph William Epstein, Monroe, NY (US); Semiramis Ayral-Kaloustian, Tarrytown, NY (US); Gary Harold Birnberg, Tuxedo Park, NY (US); Edward James Salaski, Tenafly, NJ (US); Gloria Jean Macewan, Monroe, NY (US); Katherine Cheung, Paramus, NJ (US)

(73) Assignee: Wyeth Holdings Corporation, Madison, NJ (US)

(*) Notice: Subject to any disclaimer, the term of this patent is extended or adjusted under 35 U.S.C. 154(b) by 139 days.

(21) Appl. No.: 10/227,084

(22) Filed: Aug. 23, 2002

(65) Prior Publication Data

US 2003/0149063 A1 Aug. 7, 2003

Related U.S. Application Data

(60) Provisional application No. 60/314,621, filed on Aug. 24, 2001, and provisional application No. 60/314,586, filed on Aug. 24, 2001.

(51) Int. Cl.$^7$ .................... C07D 417/08; C07D 417/12; C07D 417/14; A61K 31/426; A61K 31/427

(52) U.S. Cl. ...................... 514/256; 514/314; 514/342; 514/367; 514/369; 544/335; 546/175; 546/269.7; 548/181; 548/183

(58) Field of Search ............................... 514/256, 314, 514/342, 367, 369; 544/335; 546/175, 269.7; 548/181, 183

(56) References Cited

U.S. PATENT DOCUMENTS

| | | |
|---|---|---|
| 5,574,051 A | 11/1996 | Wrobel et al. |
| 5,576,313 A | 11/1996 | Fisher et al. |
| 5,605,918 A | 2/1997 | Wrobel et al. |

FOREIGN PATENT DOCUMENTS

| | | |
|---|---|---|
| EP | 0618221 A2 | 10/1994 |
| WO | WO 95/24400 | 9/1995 |
| WO | WO9535108 | 12/1995 |
| WO | WO 99/05117 | 2/1999 |
| WO | WO0198302 A1 | 12/2001 |

OTHER PUBLICATIONS

G.L. Bolton, J.S. Sebolt–Leopold, J.C. Hodges; *Annu. Rep. Med. Chem.*, 1994, 29, 165.
R.J.A. Grand in "New Molecular Targets in Cancer Chemotherapy", J.D. Kerr and P. Workman, Eds. *CRC Press*, Boca Raton, FL., 1994, p. 97.
J.L. Bos, *Cancer Res.*, 1989, 49, 4682.
J.F. Hancock, H. Paterson, C.J. Marshall, *Cell*, 1990, 63, 133.
H.W. Park, S.R. Boduluri, J.F. Moomaw, P.J. Casey, L.S. Beese, *Science*, 1997, 275, 1800.
P.J. Casey, P.A. Solski, C.J. Der, J.E. Buss, *Proc. Natl. Acad. Sci. U.S.A.*, 1989, 86, 8323.
S. Ayral–Kaloustian, J.S. Skotnicki, *Annu. Rep. Med. Chem.*, 1996, 31, 171.
T.M. Williams, *Exp. Opin. Ther. Patents*, 1998, 8, 553.
SCH–66336, *Pharmaprojects*, 1998, No. 5128.
R–115777, *Pharmaprojects*, 1998, No. 5532.
A. Zask, I. Jirkovsky, J.W. Nowicki, M.L. McCaleb, *J. Med. Chem.*, 1990, 33, 1418–1423.
L.M. Harwood, M. Julia, G. Le Thuillier, *Tetrahedron*, 1980, 36, 2483–2487.
G.L. James, M.S. Brown, J.L. Goldstein, *Methods in Enzymology*, 1995, 255, 38–46.
M.A. Garcia, et al.,*J. Biol. Chem.*, 1993, 268, 18415–18420.
J.F. Moomaw, P.J. Casey, *J. Biol. Chem.*, 1992, 267, 17438–17443.
P. Skehan, R. Storeng, D. Scudiero, A. Monks, J. Mcmohan, D: Vistica, J. Warren, J. Bokesh, S. Kenney, M.R. Boyd, *J. Natl. Cancer Instit.*, 1990, 82(13), 1107–1112.
L.V. Rubinstein, R.H. Shoemaker, K.D. Paull, R.M. Simon, S. Tosini, P. Skehan, D.A. Scudiero, A. Monks, M.R. Boyd, *J. Natl. Cancer Instit.*, 1990, 82(13), 1113–1118.
A. Monks, et al.,*J. Natl. Cancer Instit.*, 1991, 83, 757–766.
M.R. Boyd, K.D. Paull, *Drug Development Res.*, 1995, 34, 91–109.
S.P. Fricker, R.G. Buckley, *Anticancer Research*, 1996, 16, 3755–3760.
J. Wrobel, L. Zenan, A. Dietrich, M. McCaleb, B. Mihan, J. Stredy, D. Sullivan, *J. Med. Chem.*, 1998, 41, 1084–1091.
Semiramis Ayral–Kaloustian, et al., "Thiazolidinediones as Novel Farnesyltransferase Inhibitors"; Abstracts of Papers; American Chemical Society; vol. 222, No. 1–2, p. MED183, 2001.
George C. Prendergast, Neena Rane; "Farnesyltransferase Inhibitors: Mechanism and Applications"; Expert Opinion on Investigational Drugs, vol. 10, No. 12, Dec. 2001, p. 2105–2116.
PCT International Search Report—Date of Mailing—Jul. 2, 2003.

*Primary Examiner*—James O. Wilson
*Assistant Examiner*—Thomas McKenzie
(74) *Attorney, Agent, or Firm*—Daniel B. Moran

(57) ABSTRACT

This invention relates to a method of using novel 5-(arylsulfonyl)-,5-(arylsulfinyl), and 5-(arylsulfanyl)-thiazolidine-2,4-diones of Formula (I), wherein Ar, Ar', $R_6$, m and n are as defined in the specification as inhibitors of Ras FPTase, and may be used as an alternative to, or in conjunction with, traditional cancer therapy for treating ras-oncogene-dependent tumors, such as cancers of the pancreas, colon, bladder, and thyroid.

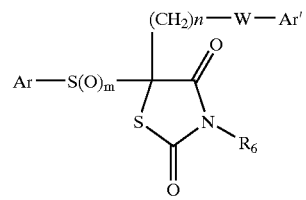

36 Claims, No Drawings

5-(ARYLSULFONYL)-,5-(ARYLSULFINYL), AND 5-(ARYLSULFANYL)-THIAZOLIDINE-2,4-DIONES USEFUL FOR INHIBITION OF FARNESYL-PROTEIN TRANSFERASE

"This application claims priority from copending provisional applications Serial No. 60/314,586 and 60/314,621 filed on Aug. 24, 2001 the entire disclosure of which are hereby incorporated by reference."

FIELD OF THE INVENTION

This invention relates to a novel series of 5-(arylsulfonyl)-,5-(arylsulfinyl), and 5-(arylsulfanyl)-thiazolidine-2,4-diones of formula (I) to their use in cancer therapy, to pharmaceutical compositions containing them, and to a process for their preparation. The compounds are inhibitors of Ras FPTase, and may be used as an alternative to, or in conjunction with, traditional cancer therapy for treating ras- oncogene-dependent tumors, such as cancers of the pancreas, colon, bladder, and thyroid. Compounds in the invention may also be useful for controlling metastasis, suppressing angiogenesis, inducing apoptosis, and in treating Ras-associated proliferative diseases other than cancer, such as restenosis, neuro-fibromatosis, endometriosis, and psoriasis. These compounds may also inhibit prenylation of proteins other than Ras, and thus be effective in the treatment of diseases associated with other prenyl modifications of proteins.

BACKGROUND OF THE INVENTION

Mammalian H-, K-, and N-Ras proteins, encoded by H-, K-, and N-ras proto-oncogenes, respectively, are 21 kD GTP-binding proteins which possess intrinsic GTPase activity and play a fundamental role in cell proliferation and differentiation (G. L. Bolton, J. S. Sebolt-Leopold, and J. C. Hodges, *Annu. Rep. Med. Chem.*, 1994, 29, 165; R. J. A. Grand in "New Molecular Targets in Cancer Chemotherapy" J. D. Kerr, and P. Workman, Eds., *CRC Press*, Boca Raton, Fla., 1994, p. 97). Specific mutations in the ras gene impair GTPase activity of Ras, leading to uninterrupted growth signals and to the transformation of normal cells into malignant phenotypes. Mutant ras oncogenes are found in approximately 25% of all human cancers, including 90% of pancreatic, 50% of colon, and 50% of thyroid tumors (J. L. Bos, *Cancer Res.*, 1989, 49, 4682). It has been shown that normal cells transfected with mutant ras gene become cancerous and that unfarnesylated, cytosolic mutant Ras protein does not anchor in cell membranes and cannot induce this transformation (J. F. Hancock, H. Paterson, and C. J. Marshall, *Cell*, 1990, 63,133). Posttranslational modification and plasma membrane association of mutant Ras is essential for this transforming activity. The first and required step in the processing of Ras is farnesylation at the cysteine residue of its carboxyl terminal motif, CAAX (C=Cys-186, A=aliphatic amino acid, X=usually methionine, serine or glutamine). Since its identification, the enzyme farnesyl-protein transferase (FPTase) that catalyzes this first processing step has emerged as a promising target for therapeutic intervention (H.-W. Park, S. R. Boduluri, J. F. Moomaw, P. J. Casey, and L. S. Beese, *Science*, 1997, 275, 1800; P. J. Casey, P. A. Solski, C. J. Der, and J. E. Buss, *Proc. Natl. Acad. Sci. U.S.A.*, 1989, 86, 8323; S. Ayral-Kaloustian and J. S. Skotnicki, *Annu. Rep. Med. Chem.*, 1996, 31, 165, and references therein). Major milestones have been achieved with small molecules, such as mimics of the tetrapeptide CAAX and analogs of farnesyl pyrophosphate, that show efficacy without toxicity in vitro as well as in mouse models bearing ras-dependent tumors or human xenografts with H-, N-, or K-ras mutations (S. Ayral-Kaloustian and J. S. Skotnicki, *Annu. Rep. Med. Chem.*, 1996, 31, 165, and references therein; T. M. Williams, *Exp. Opin. Ther. Patents*, 1998, 8, 553, and references therein). Several low-molecular weight compounds that inhibit FPTase have entered Phase I trials in humans (SCH-66336, *Pharmaprojects*, 1998, No. 5128; R-115777, *Pharmaprojects*, 1998, No. 5532).

5-[3-aryl-prop-2-ynyl]-5-(arylsulfonyl)thiazolidine-2,4-diones and 5-[3-aryl-prop-2-ynyl]-5-(arylsulfanyl) thiazolidine-2,4-diones which possess antihyperglycemic activity, are reported in U.S. Pat. Nos. 5,574,051 and 5,605,918.

Accordingly, there is still a need for drugs for treating and preventing cancer. In particular, there is a need for drugs which inhibit or treat the growth of tumors expressing an activated Ras oncogene and which include cancers of the pancreas, colon, bladder and thyroid.

BRIEF SUMMARY OF THE INVENTION

The present invention disclosed compounds represented by Formula (I):

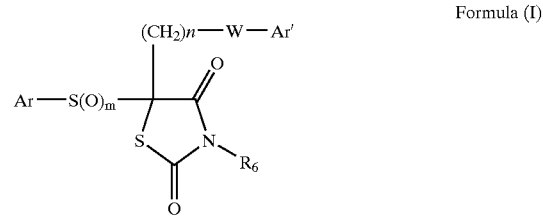

Formula (I)

wherein:

Ar is 1-naphthyl, 2-naphthyl, 8-quinolinyl, 2-thienyl, 5-chloro-2-thienyl, 5-(2-pyridyl)-2-thienyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-benzo-[b]-thienyl or a moiety of the formula:

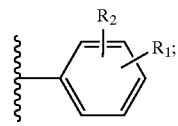

$R_1$ is hydrogen, fluoro, bromo, chloro, iodo, alkyl of 1 to 6 carbon atoms, alkoxy of 1 to 6 carbon atoms, 4-pyridyloxy, azido, nitro, acetamido, trifluoromethoxy, phenoxy, or benzyloxy;

$R_2$ is hydrogen, fluoro, bromo, chloro, iodo, alkyl of 1 to 6 carbon atoms, alkoxy of 1 to 6 carbon atoms, trifluoromethoxy, phenoxy, or benzyloxy;

m is 0, 1 or 2;

$R_6$ is hydrogen, alkyl of 1 to 6 carbon atoms, benzyl, substituted benzyl, imidazolylpropyl, or —$CO_2Y$;

Y is 2-methoxyethyl, alkyl is 1 to 6 carbon atoms, benzyl, or substituted benzyl;

W is

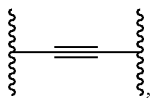

E— and Z——CH=CH—, —CONH—, —CONHCH$_2$—, —CONHCH$_2$CH$_2$—, or —CH$_2$—CH$_2$—;

n is an integer of 1 to 9;

Ar' is thienyl, pyridinyl or a moiety of the formula:

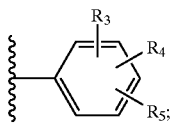

R$_3$, R$_4$, R$_5$, are independently selected from hydrogen, alkoxy of 1 to 6 carbon atoms, alkyl of 1 to 6 carbon atoms, fluoro, bromo, chloro, iodo, nitro, amino, hydroxy, azido, cyano, phenyl, phenoxy, trifluoromethyl, trifluoromethoxy, methanesulphonyl, 1-pyrrolyl, —CO$_2$R$_7$, —CONHR$_8$, —CH$_2$CONHR$_9$, —NHCO$_2$R$_{10}$, —NHCOR$_{11}$, and —NHCONHR$_{12}$;

R$_7$ is selected from H, and alkyl of 1 to 6 carbon atoms,

R$_8$ is selected from H, and alkyl of 1 to 6 carbon atoms;

R$_9$ is selected from H, and alkyl of 1 to 6 carbon atoms;

R$_{10}$ is selected from alkyl of 1 to 6 carbon atoms, benzyl, nitrobenzyl, and chlorophenyl;

R$_{11}$ is selected from alkyl of 1 to 6 carbon atoms, benzyl, phenyl, halophenyl, alkyl(1 to 6 carbon atoms)phenyl, alkoxy(1 to 6 carbon atoms)phenyl, and biphenyl;

R$_{12}$ is benzyl, alkyl of 1 to 6 carbon atoms, alkoxy(1 to 6 carbon atoms)phenyl, halophenyl, and alkyl(1 to 6 carbon atoms)phenyl;

provided that when W is

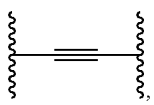

then n is other than 2;

further provided that when n is 1, m is 0 or 2, R$_6$ is H and W is

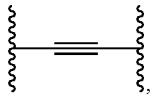

then:

Ar is not phenyl, 2-naphthyl, alkyl substituted phenyl, alkoxy substituted phenyl, halogen substituted phenyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, 2-benzo-[b]-thienyl; and Ar' is not phenyl, alkyl substituted phenyl, perfluoroalkyl (mono or di)substituted phenyl, halogen substituted phenyl, alkoxy substituted phenyl, perfluoroalkoxy substituted phenyl and alkylthio substituted phenyl;

or pharmaceutically acceptable salts thereof.

Among the preferred groups of compounds of Formula (I) of this invention including pharmaceutically acceptable salts thereof are those in the subgroups below, wherein the other variables of Formula (I) in the subgroups are as defined above wherein:

a.) R$_6$ is hydrogen, n is 3, m is 2, W is

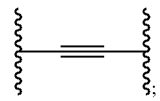

b.) R$_6$ is hydrogen, n is 3, m is 2, W is

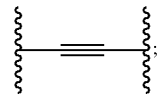

Ar is a moiety of the formula:

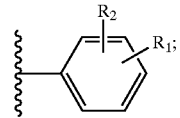

c.) R$_6$ is hydrogen, n is 3, m is 2, W is

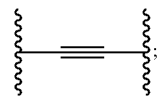

Ar is a moiety of the formula:

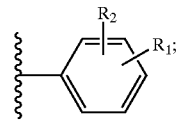

Ar' is a moiety of the formula:

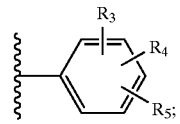

d.) R$_6$ is hydrogen, n is 3, m is 2, W is

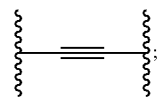

Ar is a moiety of the formula:

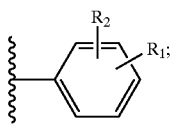

Ar' is thienyl or pyridinyl;

e.) R$_6$ is hydrogen, n is 3–6, m is 2, W is

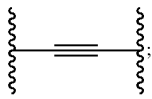

f.) R$_6$ is hydrogen, n is 3–6, m is 2, W is

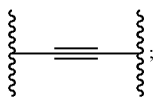

Ar is a moiety of the formula:

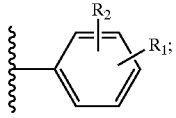

g.) R$_6$ is hydrogen, n is 3–6, m is 2, W is

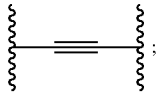

Ar is a moiety of the formula:

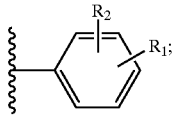

Ar' is a moiety of the formula:

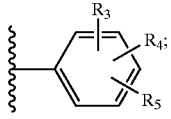

h.) R$_6$ is hydrogen, n is 3–6, m is 2, W is

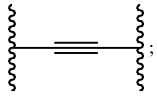

Ar is a moiety of the formula:

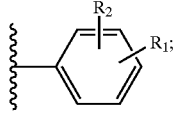

Ar' is thienyl or pyridinyl;

i.) R$_6$ is hydrogen, n is 1, m is 2, W is

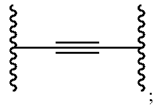

j.) R$_6$ is hydrogen, n is 1, m is 2, W is

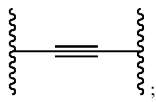

Ar is a moiety of the formula:

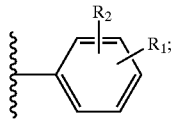

k.) R$_6$ is hydrogen, n is 1, m is 2, W is

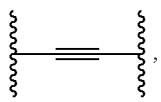

Ar is a moiety of the formula:

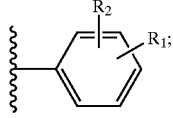

Ar' is a moiety of the formula:

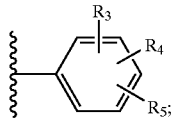

l.) R$_6$ is hydrogen, n is 1, m is 2, W is

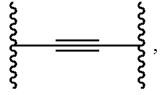

Ar is a moiety of the formula:

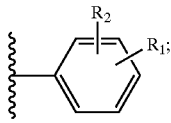

Ar' is thienyl or pyridinyl;

Additionally preferred compounds of this invention include compounds of Formula (I) in which m is 2, Ar is phenyl substituted in the 4-position by iodo, methoxy, trifluoromethoxy, 4-pyridyloxy; Ar' is phenyl substituted in the 2-position by chloro or methyl, and in the 5-position by amino, chloro, a carbamic acid ester, a substituted carboxamide group, or in the 4-position by nitro or a carbamic acid ester; W is an acetylenic group, and n is the integer 3.

Specifically preferred compounds of this invention according to Formula (I) for treating or controlling ras oncogene-dependent tumors and associated proliferative diseases in warm-blooded animals preferably mammals, most preferably humans in need thereof are the following compounds or a pharmaceutically acceptable salt thereof:

5-[5-(4-Chlorophenyl)pent-4-ynyl]-5-(4-methoxyphenylsulfanyl)-thiazolidine-2,4-dione, 5-[6-(4-Chlorophenyl)hex-5-ynyl]-5-(4-methoxyphenylsulfanyl)-thiazolidine-2,4-dione, 5-[11-(4-Chlorophenyl)undec-10-ynyl]-5-(4-methoxyphenylsulfanyl)-thiazolidine-2,4-dione, 5-(4-Methoxyphenylsulfanyl)-5-(5-thiophen-2-yl-pent-4-ynyl)-thiazolidine-2,4-dione, 5-[5-(4-Chlorophenyl)pent-4-ynyl]-5-(4-fluorophenylsulfanyl)-thiazolidine-2,4-dione, 5-[5-(4-Chlorophenyl)pent-4-ynyl]-5-(4-methoxyphenylsulfonyl)-thiazolidine-2,4-dione, 5-[6-(4-Chlorophenyl)hex-5-ynyl]-5-(4-methoxyphenylsulfonyl)-thiazolidine-2,4-dione, 5-[11-(4-Chlorophenyl)undec-10-ynyl]-5-(4-methoxyphenylsulfonyl)-thiazolidine-2,4-dione, 5-[5-(4-Chlorophenyl)pent-4-ynyl]-5-(4-methoxyphenylsulfonyl)-thiazolidine-2,4-dione, 5-[5-(2-Chlorophenyl)pent-4-ynyl]-5-(4-methoxybenzenesulfonyl)-thiazolidine-2,4-dione, 5-[5-(3-Chlorophenyl)pent-4-ynyl]-5-(4-methoxybenzenesulfonyl)-thiazolidine-2,4-dione, 5-[5-(4-Chlorophenyl)pent-4-ynyl]-5-(p-tolylsulfonyl)-thiazolidine-2,4-dione, 5-[5-(4-Chlorophenyl)pent-4-ynyl]-5-(4-iodobenzenesulfonyl)-thiazolidine-2,4-dione, 5-[5-(4-Chlorophenyl)pent-4-ynyl]-5-(4-fluorobenzenesulfonyl)-thiazolidine-2,4-dione, 5-[5-(4-Chlorophenyl)pent-4-ynyl]-5-(4-phenoxybenzenesulfonyl)-thiazolidine-2,4-dione, 5-[5-(4-Chlorophenyl)pent-4-ynyl]-5-(naphthalene-2-sulfonyl)-thiazolidine-2,4-dione, N-(4-{5-[5-(4-Chlorophenyl)pent-4-ynyl]-2,4-dioxothiazolidine-5-sulfonyl}phenyl)acetamide, 5-[5-(4-Chlorophenyl)pent-4-ynyl]-5-(quinoline-8-sulfonyl)-thiazolidine-2,4-dione, 5-[5-(4-Chlorophenyl)pent-4-ynyl]-5-(4-nitrobenzenesulfonyl)-thiazolidine-2,4-dione, 5-(4-Benzyloxybenzenesulfonyl)-5-[5-(4-chlorophenyl)pent-4-ynyl]-thiazolidine-2,4-dione, 5-(4-Butoxybenzenesulfonyl)-5-[5-(4-chlorophenyl)-pent-4-ynyl]-thiazolidine-2,4-dione, 5-[5-(4-Chlorophenyl)pent-4-ynyl]-5-(naphthalene-1-sulfonyl)-thiazolidine -2,4-dione, 5-[5-(2,5-Dichloro-phenyl)pent-4-ynyl]-5-(4-methoxy-benzenesulfonyl)-thiazolidine-2,4-dione, 5-[5-(2,5-Dichloro-phenyl)pent-4-ynyl]-5-(4-iodobenzenesulfonyl)-thiazolidine-2,4-dione, 5-[5-(2,5-Dichlorophenyl)pent-4-ynyl]-5-[4-(pyridin-4-yloxy)benzenesulfonyl]thiazolidine-2,4-dione, 5-[5-(2,4-Dichlorophenyl)pent-4-ynyl]-5-(4-methoxybenzenesulfonyl)-thiazolidine-2,4-dione, 5-(4-Methoxybenzenesulfonyl)-5-[5-(3-nitrophenyl)pent-4-ynyl]-thiazolidine-2,4-dione, 5-[5-(3-Nitrophenyl)pent-4-ynyl]-5-(4-phenoxybenzenesulfonyl)-thiazolidine-2,4-dione, 5-(4-Iodobenzenesulfonyl)-5-[5-(4-nitrophenyl)pent-4-ynyl]-thiazolidine-2,4-dione, 5-(4-Methoxybenzene sulfonyl)-5-[5-(4-nitrophenyl)pent-4-ynyl]-thiazolidine-2,4-dione, 5-(4-Methoxybenzene sulfonyl)-5-[5-(2-methyl-5-nitrophenyl)pent-4-ynyl]-thiazolidine-2,4-dione, 5-(4-Methoxybenzenesulfonyl)-5-[5-(2-methoxy-5-nitrophenyl)pent-4-ynyl]thiazolidine-2,4-dione, 5-[5-(2-Methyl-5-nitrophenyl)pent-4-ynyl]-5-(4-phenoxybenzenesulfonyl)-thiazolidine-2,4-dione, 5-(4-Iodobenzenesulfonyl)-5-[5-(2-methyl-5-nitrophenyl)pent-4-ynyl]-thiazolidine-2,4-dione, 5-[5-(2-Methyl-5-nitrophenyl)-pent-4-ynyl]-5-(naphthalene-1-sulfonyl)-thiazolidine-2,4-dione, 5-[5-(2-Methyl-5-nitrophenyl)pent-4-ynyl]-5-(naphthalene-2-sulfonyl)-thiazolidine-2,4-dione, 5-[5-(2-Methyl-4-nitrophenyl)pent-4-ynyl]-5-[4-(pyridin-4-yloxy)-benzenesulfonyl]-thiazolidine-2,4-dione, 5-[5-(2-Methyl-4-nitrophenyl)pent-4-ynyl]-5-(4-phenoxybenzene-sulfonyl)-thiazolidine-2,4-dione, 5-(4-Methoxybenzenesulfonyl)-5-[5-(2-methyl-4-nitrophenyl)-pent-4-ynyl]-thiazolidine-2,4-dione, 5-(4-Iodobenzenesulfonyl)-5-[5-(2-methyl-4-nitrophenyl)pent-4-ynyl]-thiazolidine-2,4-dione, 5-(4-Methoxybenzenesulfonyl)-5-[5-(2-methoxy-4-nitrophenyl)pent-4-ynyl]-thiazolidine-2,4-dione, 5-[5-(3-Fluoro-5-nitrophenyl)pent-4-ynyl]-5-(4-methoxybenzenesulfonyl)-thiazolidine-2,4-dione, 5-[5-(2,5-Dimethylphenyl)pent-4-ynyl]-5-(4-iodobenzenesulfonyl)-thiazolidine-2,4-dione, 5-[5-(2,5-Dimethylphenyl)pent-4-ynyl]-5-(4-methoxybenzenesulfonyl)-thiazolidine-2,4-dione, 5-[5-(2,4-Dimethylphenyl)pent-4-ynyl]-5-(4-methoxybenzenesulfonyl)-thiazolidine-2,4-dione, 5-[5-(2,4-Dimethylphenyl)pent-4-ynyl]-5-(4-iodobenzenesulfonyl)-thiazolidine-2,4-dione, 5-[5-(5-Chloro-2-methylphenyl)pent-4-ynyl]-5-(4-methoxybenzene-sulfonyl)-thiazolidine-2,4-dione, 5-[5-(5-Chloro-2-methylphenyl)pent-4-ynyl]-5-(4-trifluoromethoxybenzene-sulfonyl)-thiazolidine-2,4-dione, 5-[5-(4-Chloro-2-methylphenyl)pent-4-ynyl]-5-(4-trifluoromethoxy-benzenesulfonyl)-thiazolidine-2,4-dione, 5-[5-(4-Chloro-2-methylphenyl)-pent-4-ynyl]-5-(4-iodobenzenesulfonyl)-thiazolidine-2,4-dione, 5-[5-(4-Chloro-2-methylphenyl)pent-4-ynyl]-5-(4-methoxybenzene-sulfonyl)-thiazolidine-2,4-dione, 5-[5-(4-Bromo-2-methy-phenyl)pent-4-ynyl]-5-(4-methoxybenzene-sulfonyl)-thiazolidine-2,4-dione, 5-[5-(4-Bromo-2-methylphenyl)pent-4-ynyl]-5-(4-iodobenzenesulfonyl)-thiazolidine-2,4-dione, (4-{5-[5-(4-Methoxybenzensulfonyl)-2,4-dioxothiazolidin-5-yl]pent-1-ynyl}phenyl)carbamic Acid tert-Butyl Ester, (3-Chloro-4-{5-[5-(4-methoxybenzene sulfonyl)-2,4-dioxothiazolidin-5-yl]pent-1-ynyl}phenyl)carbamic Acid tert-Butyl Ester, N-tert-Butyl-3-{5-[5-(4-iodo-benzenesulfonyl)-2,4-dioxothiazol-idin-5-yl]-pent-1-ynyl}-4-methyl-benzamide, (3-{5-[5-(4-Iodobenzenesulfonyl)-2,4-dioxothiazolidin-5-yl]-pent-1-ynyl}-4-methylphenyl)carbamic Acid tert-Butyl Ester, (4-{5-[5-(4-Methoxybenzenesulfonyl)-2,4-dioxo-thiazolidin-5-yl]pent-1-ynyl}-3-methylphenyl) carbamic Acid tert-Butyl Ester, (3-{5-[5-(4-Methoxybenzenesulfonyl)-2,4-dioxothiazolidin-5-yl]pent-1-ynyl}-4-methylphenyl) carbamic Acid tert-Butyl Ester, (4-{5-[5-(4-Methoxybenzenesulfonyl)-2,4-dioxothiazolidin-5-yl]pent-1-ynyl}-3-trifluoromethylphenyl)carbamic Acid tert-Butyl Ester, N-tert-Butyl-3-{5-[5-(4-methoxy-benzenesulfonyl)-2,4-dioxothiazolidin-5-yl]pent-1-ynyl}-4-methyl-benzamide, 5-(4-Methoxybenzenesulfonyl)-5-[5-(4-trifluoromethylphenyl)pent-4-ynyl]-thiazolidine-2,4-dione, 5-(4-Methoxybenzenesulfonyl)-5-[5-(4-trifluoromethoxyphenyl)pent-4-ynyl]-thiazolidine-2,4-dione, 3-{5-[5-(4-Methoxybenzenesulfonyl)-2,4-dioxothiazolidin-5-yl]-pent-1-ynyl}-4-methylbenzoic Acid Methyl Ester, 5-[5-(4-tert-Butylphenyl)pent-4-ynyl]-5-(4-methoxybenzenesulfonyl)-thiazolidine-2,4-dione, 5-[5-(4-tert-Butylphenyl)pent-4-ynyl]-5-(toluene-4-sulfonyl)-thiazolidine-2,4-dione, 4-{5-[5-(4-Methoxybenzenesulfonyl)-2,4-dioxothiazolidin-5-yl]pent-1-ynyl}benzonitrile, 5-[5-(4-Methanesulfonylphenyl)-pent-4-ynyl]-5-(toluene-4-sulfonyl)-thiazolidine-2,4-dione, 4-{5-[5-(4-Methoxybenzenesulfonyl)-2,4-dioxothiazolidin-5-yl]pent-1-ynyl}-3-methylbenzoic Acid Methyl Ester, 5-(4-Methoxybenzenesulfonyl)-5-[5-(4-pyrrol-1-ylphenyl)pent-4-ynyl]-thiazolidine-2,4-dione, 5-(4-Iodo-benzenesulfonyl)-5-[5-(4-pyrrol-1-yl-phenyl)pent-4-ynyl]-thiazolidine-2,4-dione, 5-[5-(4-Pyrrol-1-ylphenyl)pent-4-ynyl]-5-(4-trifluoromethoxybenzenesulfonyl) -thiazolidine-2,4-dione, 5-(3-Methoxybenzenesulfonyl)-5-(5-thiophen-2-yl-pent-4-ynyl)-thiazolidine-2,4-dione, 5-(4-Methylphenylsulfonyl)-5-(5-thiophen-2-yl-pent-4-ynyl)-thiazolidine-2,4-dione, 5-(4-Methoxybenzenesulfonyl)-5-(5-thiophen-2-yl-pent-4-ynyl)-thiazolidine-2,4-dione, 5-(4-Methoxybenzenesulfonyl)-5-(3-pyridin-3-ylprop-2-ynyl)-thiazolidine-2,4-dione, 5-(3-Thiophen-2-yl-prop-2-ynyl)-5-(toluene-4-sulfonyl)-thiazolidine-2,4-dione, 5-(3-Biphenyl-4-yl-prop-2-ynyl)-5-(toluene-4-sulfonyl)-thiazolidine-2,4-dione, 5-[3-(4-Phenoxyphenyl)prop-2-ynyl]-5-(toluene-4-sulfonyl)-thiazolidine-2,4-dione, 5-(3-Biphenyl-4-yl-prop-2-ynyl)-5-(4-methoxybenzenesulfonyl)-thiazolidine-2,4-dione, 5-(5-Pyridin-3-yl-pent-4-ynyl)-5-(toluene-4-sulfonyl)-thiazolidine-2,4-dione, 5-[5-(5-Amino-2-methylphenyl)pent-4-ynyl]-5-(4-methoxybenzenesulfonyl)-thiazolidine-2,4-dione, (3-{5-[5-(4-Methoxybenzenesulfonyl)-2,4-dioxothiazolidin-5-yl]pent-1-ynyl}-4-methylphenyl) carbamic Acid Benzyl Ester, (3-{5-[5-(4-Methoxybenzenesulfonyl)-2,4-dioxothiazolidin-5-yl]pent-1-ynyl}-4-methylphenyl) carbamic Acid 4-Nitro-Benzyl Ester, (3-{5-[5-(4-Methoxybenzenesulfonyl)-2,4-dioxothiazolidin-5-yl]pent-1-ynyl}-4-methylphenyl) carbamic Acid 4-Chloro-phenyl Ester, (3-{5-[5-(4-Methoxybenzenesulfonyl)-2,4-dioxothiazolidin-5-yl]pent-1-ynyl}-4-methylphenyl) carbamic Acid Methyl Ester, (3-{5-[5-(4-Methoxybenzenesulfonyl)-2,4-dioxothiazolidin-5-yl]pent-1-ynyl}-4-methylphenyl) carbamic Acid Isopropyl Ester, (3-{5-[5-(4-Methoxybenzenesulfonyl)-2,4-dioxothiazolidin-5-yl]pent-1-ynyl}-4-methylphenyl) carbamic Acid Neopentyl Ester, (3-{5-[5-(4-Methoxybenzenesulfonyl)-2,4-dioxothiazolidin-5-yl]pent-1-ynyl}-4-methylphenyl) carbamic Acid Butyl Ester, (3-{5-[5-(4-Methoxybenzenesulfonyl)-2,4-dioxothiazolidin-5-yl]pent-1-ynyl}-4-methylphenyl) carbamic Acid Isobutyl, N-[3-(5-{5-[(4-Methoxyphenyl)sulfonyl]-2,4-dioxo-1,3-thiazolidin-5-yl}-1-pentynyl)-4-methylphenyl]-2-methylpropanamide, N-[3-(5-{5-[(4-Methoxyphenyl)sulfonyl]-2,4-dioxo-1,3-thiazolidin-5-yl}-1-pentynyl)-4-methylphenyl]-3,3-dimethylbutanamide, N-[3-(5-{5-[(4-Methoxyphenyl)sulfonyl]-2,4-dioxo-1,3-thiazolidin-5-yl}-1-pentynyl)-4-methylphenyl]-2,2-dimethylpropanamide, N-[3-(5-{5-[(4-Methoxyphenyl)sulfonyl]-2,4-dioxo-1,3-thiazolidin-5-yl}-1-pentynyl)-4-methylphenyl]-2-phenylacetamide, N-Benzyl-N'-[3-(5-{5-[(4-methoxyphenyl)-sulfonyl]-2,4-dioxo-1,3-thiazolidin-5-yl}1-pentynyl)-4-methylphenyl]urea, N-(4-Methoxyphenyl)-N'-[3-(5-{5-[(4-methoxy phenyl) sulfonyl]-2,4-dioxo-1,3-thiazolidin-5-yl}-1-pentynyl)-4-methylphenyl]urea, N-(4-Chlorophenyl)-N'-[3-(5-{5-[(4-methoxy-phenyl) sulfonyl]-2,4-dioxo-1,3-thiazolidin-5-yl}-1-pentynyl)-4-methylphenyl]urea, N-[3-(5-{5-[(4-Methoxyphenyl)sulfonyl]-2,4-dioxo-1,3-thiazolidin-5-yl}-1-pentynyl)methylphenyl]-N'-(4-methylphenyl)urea, 4-Chloro-N-[3-(5-{5-[(4-methoxyphenyl)-sulfonyl]-2,4-dioxo-1,3-thiazolidin-5-yl}-1-pentynyl)-4-methylphenyl]benzamide, 4-Methoxy-N-[3-(5-{5-[(4-methoxyphenyl)-sulfonyl]-2, 4-dioxo-1,3-thiazolidin-5-yl}-1-pentynyl)-4-methylphenyl]benzamide, N-[3-(5-{5-[(4-Methoxyphenyl)sulfonyl]-2,4-dioxo-1,3-thiazolidin-5-yl}-1-pentynyl)-4-methylphenyl][1,1'-biphenyl]-4-carboxamide, 4-(tert-Butyl)-N-[3-(5-{5-[(4-methoxyphenyl)-sulfonyl]-2,4-dioxo-1,3-thiazolidin-5-yl}-1-pentynyl)-4-methylphenyl]benzamide, 5-[5-(4-Chlorophenyl)-4-pentynyl]-5-[(5-chloro-2-thienyl)sulfonyl]-1,3-thiazolidine-2,4-dione, 5-[5-(4-Chlorophenyl)-4-pentynyl]-5-(2-thienylsulfonyl)-1,3-thiazolidine-2,4-dione, 5-[5-(4-Chlorophenyl)-4-pentynyl]-5-[(3,4-dimethoxyphenyl)sulfonyl]-1,3-thiazolidine-2,4-dione, 5-[5-(4-Chlorophenyl)-4-pentynyl]-5-{[4-(4-pyridinyloxy)phenyl]sulfonyl}-1,3-thiazolidine-2,4-dione, 5-[5-(4-Chlorophenyl)-4-pentynyl]-5-{[5-(2-pyridinyl)-2-thienyl]sulfonyl}-1,3-thiazolidine-2,4-dione, 5-[(5-Chloro-2-thienyl)sulfonyl]-5-[5-(2,5-dichlorophenyl)-4-pentynyl]-1,3-thiazolidine-2,4-dione, 5-[5-(2,5-Dichlorophenyl)-4-pentynyl]-5-(2-thienylsulfonyl)-1,3-thiazolidine-2,4-dione, 5-[5-(2,5-Dichlorophenyl)-4-pentynyl]-5-[(3,4-dimethoxyphenyl)sulfonyl]-1,3-thiazolidine-2,4-dione, 5-[5-(2,5-Dichlorophenyl)-4-pentynyl]-5-{[4-(4-pyridinyloxy)phenyl]sulfonyl}-1,3-thiazolidine-2,4-dione, 5-[5-(2,5-Dichlorophenyl)-4-pentynyl]-5-{[5-(2-pyridinyl)-2-thienyl]sulfonyl}-1,3-thiazolidine-2,4-dione, tert-Butyl 3-(5-{5-[(5-chloro-2-thienyl)-sulfonyl]-2,4-dioxo-1,3-thiazolidin-5-yl}-1-pentynyl)-4-methylphenylcarbamate, tert-Butyl 3-{5-[2,4-dioxo-5-(2-thienylsulfonyl)-1,3-thiazolidin-5-yl]-1-pentyn-yl}-4-methylphenylcarbamate, tert-Butyl 3-(5-{5-[(3,4-dimethoxy-phenyl)sulfonyl]-2,4-dioxo-1,3-thiazolidin-5-yl}-1-pentynyl)-4-methylphenylcarbamate, tert-Butyl 3-[5-(2,4-dioxo-5-{[4-(4-pyridinyloxy)phenyl]sulfonyl}-1,3-thiazolidin-5-yl)-1-pentynyl]-4-methylphenyl-carbamate, tert-Butyl 3-[5-(2,4-dioxo-5-{[5-(2-pyridinyl)-2-thienyl]sulfonyl}-1,3-thiazolidin-5-yl)1-pentynyl]-4-methylphenylcarbamate, N-(tert-Butyl)-3-(5-{5-[(5-chloro-2-thienyl)sulfonyl]-2,4-dioxo-1,3-thiazolidin-5-yl}-1-pentynyl)-4-methylbenzamide, N-(tert-Butyl)-3-{5-[2,4-dioxo-5-(2-thienylsulfonyl)-1,3-thiazolidin-5-yl]-1-pentynyl}-4-methylbenzamide, N-(tert-Butyl)-3-(5-{5-[(3,4-dimethoxyphenyl)sulfonyl]-2,4-dioxo-1,3-thiazolidin-5-yl}-1-pentynyl)-4-methylbenzamide, N-(tert-Butyl)-3-[5-(2,4-dioxo-5-{[5-(2-pyridinyl)-2-thienyl]sulfonyl}-1,3-thiazolidin-5-yl)-1-pentynyl]-4-methylbenzamide, 4-{5-[5-(4-Methoxybenzenesulfonyl)-2,4-dioxothiazolidin-5-yl]pent-1-ynyl}-3-methylbenzoic Acid, N-(4-Chlorobenzyl)-3-[5-(4-methoxybenzenesulfonyl)-2,4-dioxo-thiazolidin-4-yl]propionamide, N-[2-(4-Chlorophenyl)ethyl]-3-[5-(4-methoxybenzenesulfonyl)-2,4-dioxo-thiazolidin-5-yl]propionamide, 5-[(4Z)-5-(4-Chloro-phenyl)pent-4-enyl]-5-(toluene-4-sulfonyl)-thiazolidine-2,4-dione, 5-[(4E)-5-(4-Chlorophenyl)pent-4-enyl]-5-(4-methoxybenzenesulfonyl)thiazolidine-2,4-dione, 5-[3-(4-Chlorophenyl)propyl]-5-(4-methoxybenzenesulfonyl)-thiazolidine-2,4-dione, 5-[5-(3-Aminophenyl)pent-4-ynyl]-5-(4-methoxybenzenesulfonyl)-thiazolidine-2,4-dione, 5-(3-Phenylalkyl)-5-(toluene-4-sulfonyl)-thiazolidine-2,4-dione, Enantiomer of(3-{5-[5-(4-Methoxybenzenesulfonyl)-2,4-dioxothiazolidin-5-yl]pent-1-ynyl}-4-methylphenyl) carbamic Acid tert-Butyl Ester (less polar), Enantiomer of (3-{5-[5-(4-Methoxybenzenesulfonyl)-2,4-dioxothiazolidin-5-yl]pent-1-ynyl}-4-methylphenyl) carbamic Acid tert-Butyl Ester (more polar), 5-[5-(4-Chlorophenyl)pent-4-ynyl]-5-(4-methoxyphenylsulfinyl)-thiazolidine-2,4-dione, Benzyl 5-[5-(5-{[(benzyloxy)carbonyl]-amino}-2-methylphenyl)pent-4-ynyl]-5-[(4-methoxyphenyl)sulfonyl]-2,4-dioxo-1,3-thiazolidine-3-carboxylate, 4-Nitrobenzyl 5-[(4-methoxyphenyl) sulfonyl]-5-{5-[2-methyl-5-({[(4-nitro benzyl)oxy]carbonyl}amino) phenyl]pent-4-ynyl}-2,4-dioxo-1,3-thiazolidine-3-carboxylate, Methyl 5-(5-{5-[(methoxycarbonyl)amino]-2-methylphenyl}pent-4-ynyl)-5-[(4-methoxyphenyl) sulfonyl]-2,4-dioxo-1,3-thiazolidine-3-carboxylate, Isopropyl 5-(5-{5-[(isopropoxycarbonyl)-amino]-2-methylphenyl}pent-4-ynyl)-5-[(4-methoxyphenyl) sulfonyl]-2,4-dioxo-1,3-thiazolidine-3-carboxylate, Neopentyl 5-[(4-methoxyphenyl)sulfonyl]-5-[5-(2-methyl-5-{[(neopentyloxy)carbonyl]-amino}phenyl) pent-4-ynyl]-2,4-dioxo-1,3-thiazolidine-3-carboxylate, Butyl 5-(5-{5-[(butoxycarbonyl)amino]-2-methylphenyl}pent-4-ynyl)-5-[(4-methoxyphenyl) sulfonyl]-2,4-dioxo-1,3-thiazolidine-3-carboxylate, Isobutyl 5-(5-{5-[(isobutoxycarbonyl)-amino]-2-methylphenyl}pent-4-ynyl)-5-[(4-methoxyphenyl) sulfonyl]-2,4-dioxo-1,3-thiazolidine-3-carboxylate, 5-[5-(4-Chlorophenyl)pent-4-ynyl]-3-(3-imidazol-1-yl-propyl)-5-(4-methoxybenzenesulfonyl)-thiazolidine-2,4-dione, 5-[5-(4-Chlorophenyl)pent-4-ynyl]-5-(4-methoxybenzenesulfonyl)-3-methyl-thiazolidine-2,4-dione, 5-[5-(4-Chlorophenyl)pent-4-ynyl]-3-(2,4-diethoxybenzyl)-5-(toluene-4-sulfonyl)thiazolidine-2,4-dione, 5-[5-(4-Chlorophenyl)pent-4-ynyl]-5-(4-iodobenzenesulfonyl)-3-(4-nitrobenzyl)thiazolidine-2,4-dione, and 5-[5-(2,5-Dichlorophenyl)pent-4-ynyl]-5-(4-methoxybenzenesulfonyl)-2,4-dioxothiazolidine-3-carboxylic acid 2-methoxy ethyl ester.

The present invention also discloses a process for the preparation of a compound of Formula (I):

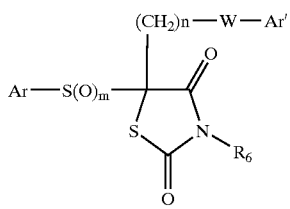

Formula (I)

wherein:
Ar is 1-naphthyl, 2-naphthyl, 8-quinolinyl, 2-thienyl, 5-chloro-2-thienyl, 5-(2-pyridyl)-2-thienyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-benzo-[b]-thienyl or a moiety of the formula:

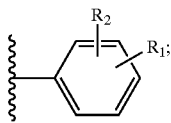

$R_1$ is hydrogen, fluoro, bromo, chloro, iodo, alkyl of 1 to 6 carbon atoms, alkoxy of 1 to 6 carbon atoms, 4-pyridyloxy, azido, nitro, acetamido, trifluoromethoxy, phenoxy, or benzyloxy;

$R_2$ is hydrogen, fluoro, bromo, chloro, iodo, alkyl of 1 to 6 carbon atoms, alkoxy of 1 to 6 carbon atoms, trifluoromethoxy, phenoxy, or benzyloxy;

m is 0, 1 or 2;

$R_6$ is hydrogen;

Y is 2-methoxyethyl, alkyl is 1 to 6 carbon atoms, benzyl, or substituted benzyl;

W is

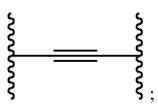

E— and Z——CH=CH—, —CONH—, —CONHCH$_2$—, —CONHCH$_2$CH$_2$— or —CH$_2$—CH$_2$—;

n is an integer of 1 to 9;

Ar' is thienyl, pyridinyl or a moiety of the formula:

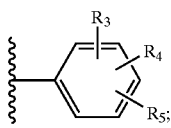

$R_3$, $R_4$, $R_5$, are independently selected from hydrogen, alkoxy of 1 to 6 carbon atoms, alkyl of 1 to 6 carbon atoms, fluoro, bromo, chloro, iodo, nitro, amino, hydroxy, azido, cyano, phenyl, phenoxy, trifluoromethyl, trifluoromethoxy, methanesulphonyl, 1-pyrrolyl, —CO$_2$R$_7$, —CONHR$_8$, —CH$_2$CONHR$_9$, —NHCO$_2$R$_{10}$, —NHCOR$_{11}$, and —NHCONHR$_{12}$;

$R_7$ is selected from H, and alkyl of 1 to 6 carbon atoms, $R_8$ is selected from H, and alkyl of 1 to 6 carbon atoms;

$R_9$ is selected from H, and alkyl of 1 to 6 carbon atoms;

$R_{10}$ is selected from alkyl of 1 to 6 carbon atoms, benzyl, nitrobenzyl, and chlorophenyl;

$R_1$ is selected from alkyl of 1 to 6 carbon atoms, benzyl, phenyl, halophenyl, alkyl(1 to 6 carbon atoms)phenyl, alkoxy(1 to 6 carbon atoms)phenyl, and biphenyl;

$R_{12}$ is benzyl, alkyl of 1 to 6 carbon atoms, alkoxy(1 to 6 carbon atoms)phenyl, halophenyl, and alkyl(1 to 6 carbon atoms)phenyl;

provided that when W is

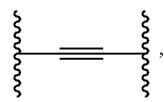

then n is other than 2;

further provided that when n is 1, m is 0 or 2, $R_6$ is H and W is

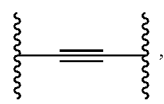

then:

Ar is not phenyl, 2-naphthyl, alkyl substituted phenyl, alkoxy substituted phenyl, halogen substituted phenyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, 2-benzo-[b]-thienyl; and Ar' is not phenyl, alkyl substituted phenyl, perfluoroalkyl (mono or di)substituted phenyl, halogen substituted phenyl, alkoxy substituted phenyl, perfluoroalkoxy substituted phenyl and alkylthio substituted phenyl;

or pharmaceutically acceptable salts thereof, which comprises:

reacting a compound of the formula:

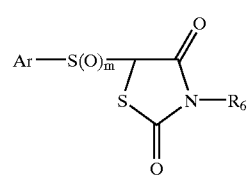

with an alkyne of the formula:

Ar'W—(CH$_2$)$_m$—LG wherein LG is a leaving group in the presence of a base to give a compound of Formula (I) or a pharmaceutically acceptable salt thereof.

It is understood that the definition of compounds of Formula (I) when $R_1$ to $R_{12}$, contain asymmetric carbons, encompass all possible stereoisomers and mixtures thereof which possess the activity discussed below. In particular, the definition encompasses racemic modifications and any optical isomers which possess the indicated activity. Optical isomers may be obtained in pure form by standard separation techniques or enantiomer specific synthesis. It is understood that this invention encompasses all crystalline forms of compounds of Formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic, and similarly known acceptable acids. Where $R_1$ to $R_{12}$, or Y contains a carboxyl group, salts of the compounds in this invention may be formed with bases such as alkali metals (Na, K, Li) or alkaline earth metals (Ca or Mg).

For the compounds of Formula (I) defined above and referred to herein, unless otherwise noted, the following terms are defined:

Halogen, as used herein means chloro, fluoro, bromo and iodo.

Alkyl as used herein means a branched or straight chain having from 1 to 6 carbon atoms. Exemplary alkyl groups include methyl, ethyl, propyl, isopropyl, butyl, isobutyl, t-butyl, pentyl and hexyl.

Aryl as used herein means an aromatic radical wherein Ar is 1-naphthyl, 2-naphthyl, 8-quinolinyl, 2-thienyl, 5-chloro-2-thienyl, 5-(2-pyridyl)-2-thienyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-benzo-[b]-thienyl or a moiety of the formula:

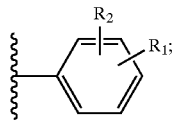

and further defined an aromatic radical Ar' is thienyl, pyridinyl or a moiety of the formula:

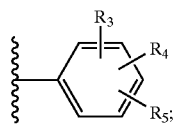

Alkoxy as used herein means an —O-alkyl group in which the alkyl group is as previously described. Exemplary alkoxy groups include methoxy, ethoxy, n-propoxy, i-propoxy, n-butoxy, and t-butoxy.

Alkyne as used herein means an alkynyl group

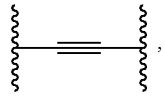

is present.

Phenyl as used herein refers to a 6-membered aromatic ring. Carbamic acid ester is —NHCO$_2$R$_{10}$ where preferred R$_{10}$ is alkyl of 1 to 6 carbon atoms.

Substituted carboxamide is —CONHR$_8$ wherein R$_8$ is alkyl of 0.1 to 6 carbon atoms.

Substituted 2-pyridinyl and substituted benzyl, unless otherwise provided for herein, preferably has from 1 to 3 substituents independently selected from fluoro, chloro, bromo, iodo, nitro, cyano, alkyl of 1 to 6 carbon atoms, alkoxy of 1 to 6 carbon atoms, trifluoromethyl and trifluoromethoxy.

This invention provides a method of treatment, by administration of an effective amount of compounds of Formula (I), of ras oncogene-dependent tumors, which include cancers of the pancreas, colon, bladder, and thyroid; a method of controlling metastasis, suppressing angiogenesis, and inducing apoptosis; a method of treating Ras-associated proliferative diseases other than cancer, which include restenosis, neuro-fibromatosis, endometriosis, and psoriasis The compounds of Formula (I) may also inhibit prenylation of proteins other than Ras, and thus provide a method of treatment of diseases associated with other prenyl modifications of proteins. The compounds of Formula (I) inhibit farnesyl-protein transferase and the farnesylation of the oncogene protein Ras. Thus, this invention further provides a method of inhibiting farnesyl protein transferase, (e.g., Ras farnesyl protein transferase) in mammals, especially humans, by the administration of an effective amount of the compounds of Formula (I). The administration of the compounds of this invention to patients, to inhibit farnesyl protein transferase, is useful in the treatment of the cancers and other diseases described below.

This invention provides a method for inhibiting or treating the abnormal growth of cells, including transformed cells by administering an effective amount of a compound of Formula (I). Abnormal growth of cells refers to cell growth independent of normal regulatory mechanisms (e.g., loss of contact inhibition). This includes abnormal growth of tumor cells (tumors) expressing an activated Ras oncogene; tumor cells in which the Ras protein is activated as a result of oncogenic mutation in another gene; and benign and malignant cells of other proliferative diseases in which aberrant Ras activation occurs.

This invention also provides a method for inhibiting or treating tumor growth by administering an effective amount of a compound of Formula (I), described herein, to a mammal (e.g., a human) in need of such treatment. In particular, this invention provides a method for inhibiting or treating the growth of tumors expressing an activated Ras oncogene by administration of an effective amount of a compound of Formula (I). Examples of tumors which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma, epidermal carcinoma, breast cancer and prostate cancer.

This invention also provides a method for inhibiting or treating proliferative diseases, both benign and malignant, wherein Ras proteins are aberrantly activated as a result of oncogenic mutation in other genes-i.e., the Ras gene itself is not activated by mutation to an oncogenic form-with said inhibition or treatment being accomplished by the administration of an effective amount of a compound of Formula (I), to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the compounds of Formula (I). Additionally, this invention provides a method of inhibition or treating the abnormal growth of cells, by administration of an effective amount of compounds of Formula (I), of ras-oncogene-dependent tumors, which tumors include cancers of the pancreas, colon, bladder, and thyroid. Without wishing to be bound by theory, these compounds may function through the inhibition of G-protein function, such as ras p21, by blocking G-protein isoprenylation, thus making them useful in the treatment of proliferative diseases such as tumor growth and cancer. Without wishing to be bound by theory, compounds of Formula (I) inhibit Ras farnesyl-protein transferase, and thus antiproliferative activity of ras-transformed cells and other prenyl modifications of proteins.

DETAILED DESCRIPTION OF THE INVENTION

Compounds of this invention may be prepared according to the methods and procedures described in U.S. Pat. Nos. 5,605,918 and 5,574,051, which are hereby incorporated herein by reference; in Wrobel, J., et al., *J. Med. Chem.* 1998, 41 (7), 1084–91 and as outlined in Schemes I through XI described herein.

Following the procedure of Zask et al (J. Med. Chem. 1990, 33, 1418–1423), the oxidation is conveniently performed using excess (2 to 20 equivalents) aqueous hydrogen peroxide in acetic acid at ambient or higher (30° to 80° C.) reaction temperatures for 1 to 10 h.

The 5-arylsulfanylthiazolidine-2,4-dione VII may also be oxidized to afford 5-arylsulfinylthiazolidine-2,4-dione Va by bubbling oxygen in the presence of isobutyraldehyde in a solvent which includes acetonitrile for 18 hours.

The 5-arylsulfonylthiazolidine-2,4-dione V may also be prepared by reacting one or more equivalents of an alkali metal arylsulfinate VIII, where M is an alkali metal with

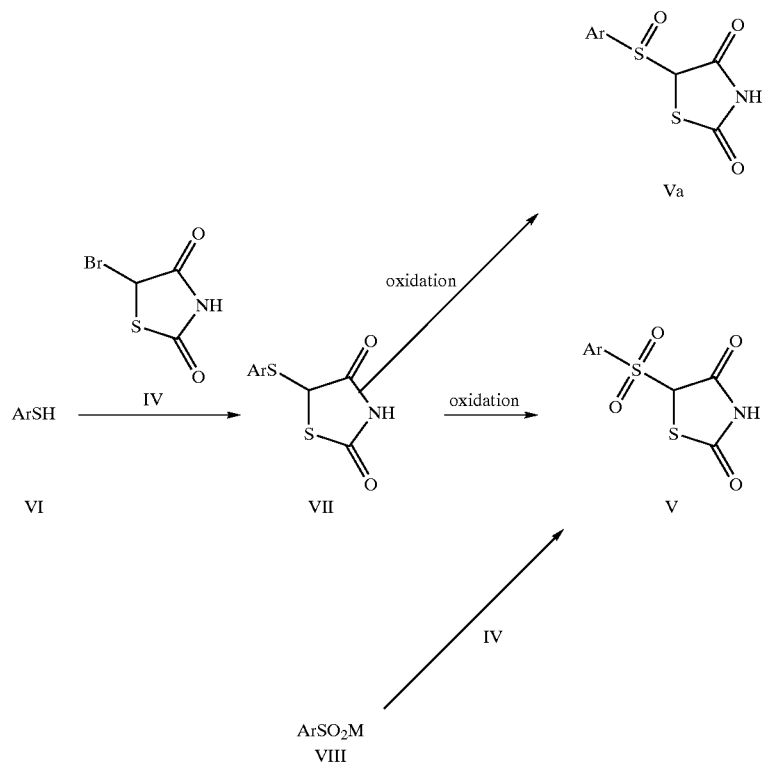

Scheme I

As shown in Scheme I, arylthiol VI where Ar is hereinbefore defined is reacted with 2 or more equivalents of a strong base such as lithium diisopropylamide, lithium bis(trimethylsilylamide), and the like followed by reaction with one or more equivalents of 5-bromothiazolidine-2,4-dione IV(Zask et al, J. Med. Chem. 1990, 33, 1418–1423) to produce a 5-arylsulfanylthiazolidine-2,4-dione VII in an aprotic solvent such as tetrahydrofuran (THF) or hexane at temperatures (e.g. 0° to −78° C.) followed by warming to about ambient temperature for 1 to 10 h.

The 5-arylsulfanylthiazolidine-2,4-dione VII may then be oxidized to afford 5-arylsulfonylthiazolidine-2,4-dione V.

5-bromothiazolidine-2,4-dione IV in suitable solvents which include polar aprotic solvents such as N,N-dimethylformamide (DMF), tetrahydrofuran (THF) or protic solvents such as low molecular weight alcohols (methyl alcohol, ethyl alcohol and isopropanol and the like), or water.

Alternatively, the alkali metal arylsulfinate VIII can also be prepared by reduction of an arylsulfonyl chloride with sodium iodide in acetone (Harwood, Julia, and Thuillier, Tetrahedron, 1980,36, 2483–2487).

Scheme II

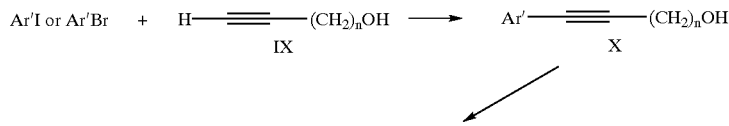

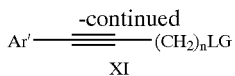

As shown in Scheme II arylalkynes XI, wherein Ar' is as previously defined, and LG is a suitable leaving group which include iodo, bromo and p-toluenesulfonyloxy, can be prepared via a two step process from commercially available aryl iodides or aryl bromides where Ar' is hereinbefore defined or those aryl iodides or aryl bromides described in the the art. In the first step, alcohol X is prepared by the reaction of the appropriate aryl iodide or bromide with one or more equivalents of a terminal alkyne-ol IX, in the presence of a catalytic amount of a palladium(II) reagent such as dichlorobis(triphenylphosphine)palladium(II) and a catalytic amount of a copper(I) reagent such as copper(I) iodide. This reaction is also performed in the presence of one or more equivalents of a secondary or tertiary amine such as diethylamine or triethylamine. The secondary or tertiary amine may be used as solvent, or alternatively a halocarbon solvent such as chloroform may be employed. Temperatures up to 80° C. are commonly used, with reaction times varying from 1 h to 2 days. Alkyne XI wherein Ar' is hereinbefore defined and LG is p-toluenesulfonyloxy is most conveniently prepared from alcohol X by reaction with p-toluenesulfonyl chloride in a solvent such as dichloromethane and in the presence of N,N-dimethylaminopyridine and triethylamine at 0° C. to 30° C., from one hour to 6 hours; or when LG is iodo, alcohol X is reacted with iodine, in the presence of triphenylphosphine and imidazole in a solvent such as ether, or acetonitrile, at a temperature of 0° C. to room temperature for 8 hours to 24 hours; alternatively alkyne XI wherein LG is p-toluenesulfonyloxy is reacted with sodium iodide in acetone at room temperature from 8 hours to 36 hours to give alkyne XI wherein LG is iodo; or when LG is bromo, X is reacted with carbon tetrabromide in the presence of triphenylphosphine in a solvent such as THF at 0° C. to 35° C. for 8 hours to 72 hours to give alkyne XI wherein LG is bromo.

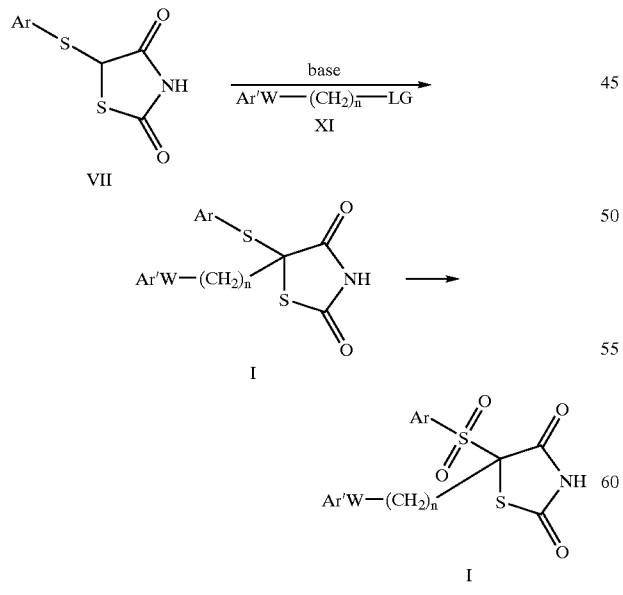

Referring to Scheme III: 5-substituted-5-(arylsulfanyl)thiazolidine-2,4-diones of Formula (I) may be prepared by reaction of the appropriate 5-(arylsulfanyl)thiazolidine-2,4-dione VII with 2 or more equivalents of a base. Two equivalents of base effect deprotonation of both the thiazolidinedione nitrogen atom and at the C-5 position to form a dianion. Common bases to accomplish this deprotonation include alkali metal hydrides such as sodium hydride, alkali metal alkyls such as butyl lithium or alkali metal amide bases such as lithium diisopropylamide or lithium bis(trimethylsilyl)amide. Convenient solvents include THF and DMF. Reaction temperatures may be varied from −78° C. to room temperature. Two minutes to 1 h after the base is introduced, one or more equivalents of the appropriate alkylating agent, alkyne XI is added to the reaction mixture and this is allowed to stir at 0° C. or room temperature for a period of from 1 h to 3 days. Alkylation occurs primarily on the thiazolidindione C-5 carbon atom to afford the 5-substituted-5-(arylsulfanyl)thiazolidine-2,4-dione of Formula (I), m=0 which may then be oxidized to afford 5-arylsulfonylthiazolidine-2,4-dione of Formula (I) wherein m=2 by the procedure of Zask et al (J. Med. Chem. 1990, 33, 1418–1423). The oxidation is conveniently performed using excess (2 to 20 equivalents) aqueous hydrogen peroxide in acetic acid at ambient or higher (30° C. to 80° C.) reaction temperatures for 1 to 10 h.

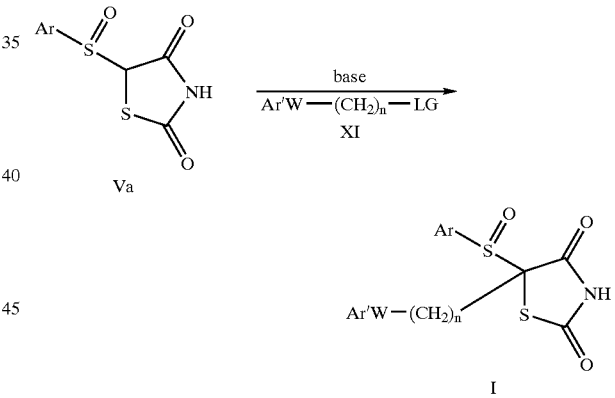

Referring to Scheme IIIa: 5-substituted-5-(arylsulfinyl)thiazolidine-2,4-diones of Formula (I) may be prepared by reaction of the appropriate 5-(arylsulfinyl)thiazolidine-2,4-dione Va in the presence of a base. Common bases include alkali metal hydrides such as sodium hydride, alkali metal alkyls such as butyl lithium or alkali metal amide bases such as lithium diisopropylamide or lithium bis(trimethylsilyl)amide. Convenient solvents include THF and DMF. Reaction temperatures may be varied from −78° C. to room temperature. Two minutes to 1 h after the base is introduced, one or more equivalents of the appropriate alkylating agent, alkyne XI is added to the reaction mixture and this is allowed to stir at 0° C. or room temperature for a period of from 1 h to 3 days. Alkylation occurs primarily on the thiazolidindione C-5 carbon atom to afford the 5-substituted-5-(arylsulfinyl)thiazolidine-2,4-dione of Formula (I), m =1.

Scheme IV

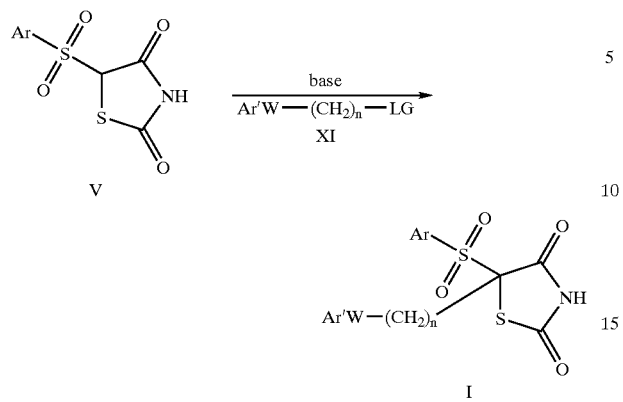

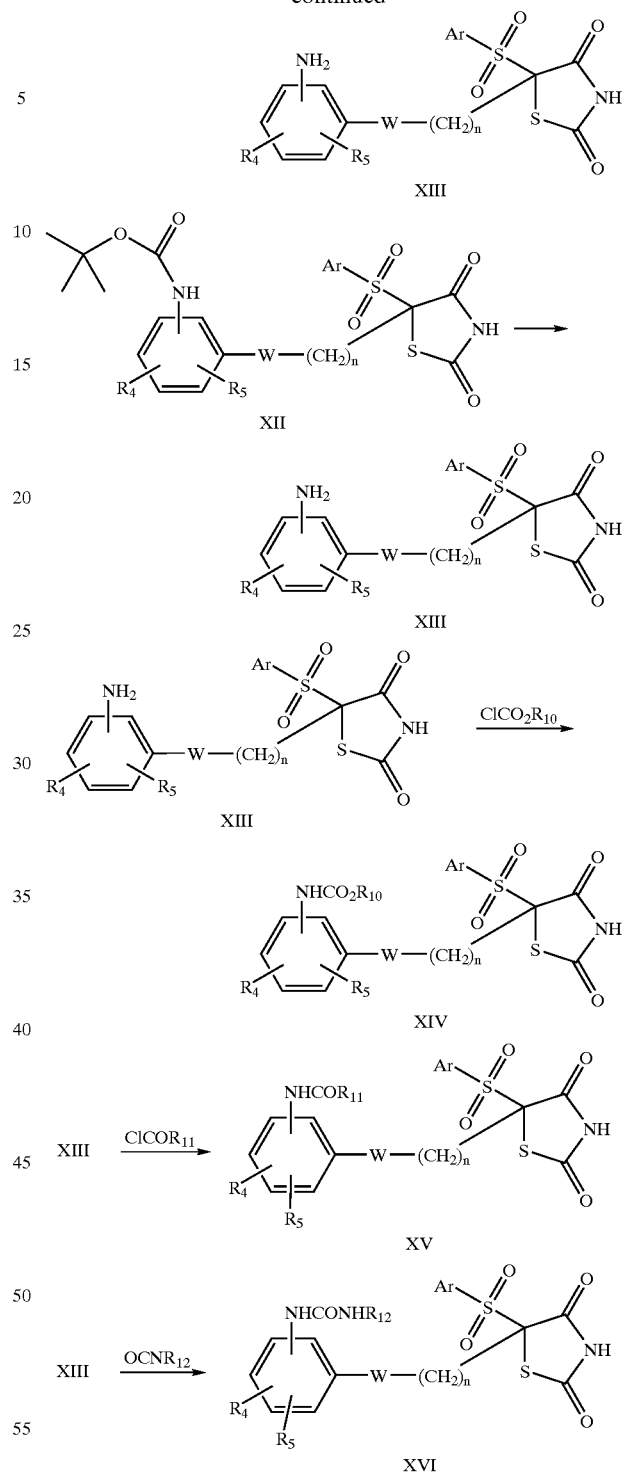

As shown in Scheme IV: 5-substituted-5-(arylsulfonyl)thiazolidine-2,4-diones of Formula (I) may be prepared by reaction of the appropriate 5-(arylsulfonyl)thiazolidine-2,4-dione V with 2 or more equivalents of a base. Two equivalents of base effect deprotonation of both the thiazolidinedione nitrogen atom and at the C-5 position to form a dianion. Common bases to accomplish this deprotonation include alkali metal hydrides such as sodium hydride, alkali metal alkyls such as butyl lithium or alkali metal amide bases such as lithium diisopropylamide or lithium bis(trimethylsilyl)amide. Convenient solvents include THF and DMF. Reaction temperatures vary from $-78°$ C. to room temperature. Two minutes to 1 h after the base is introduced, one or more equivalents of the appropriate alkylating agent, alkyne XI is added to the reaction mixture and the reaction is allowed to stir at $0°$ C. or room temperature for a period of from 1 h to 3 days. Alkylation occurs exclusively on the thiazolidindione C-5 carbon atom to afford the 5-substituted-5-(arylsulfonyl)thiazolidine-2,4-dione of formula (I).

As shown in Scheme V, a compound of Formula (I), wherein at least one of $R_3$, $R_4$, or $R_5$ of the moiety:

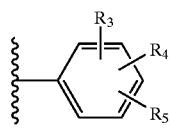

is a nitro group, and as shown in formula I' where $R_3$ is a nitro group, is reacted with a reducing agent, such as iron in acetic acid or tin in hydrochloric acid, or other agents known to effect this reduction to give an amine XIII.

Scheme V

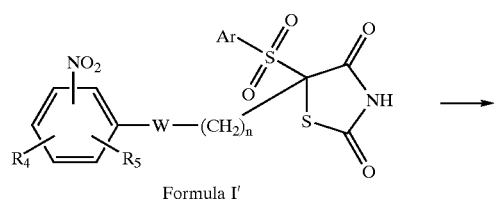

Formula I'

As further shown in Scheme V, compounds of Formula (I), wherein at least one of $R_3$, $R_4$, or $R_5$ is amino, as shown in amine XIII can be prepared by hydrolysis of carbamate XII, wherein at least one of $R_3$, $R_4$, or $R_5$ of Formula (I) is a t-butoxycarbonylamino group, by the use of an acid, such as trifluoroacetic acid, or aqueous hydrochloric acid at $0°$ C. to $60°$ C., from 0.5 h to 4 h.

Substituted amine XIV, wherein at least one of $R_3$, $R_4$, or $R_5$ is $—NHCO_2R_{10}$ wherein $R_{10}$ is selected from alkyl of 1 to 6 carbon atoms, benzyl, nitrobenzyl, chlorophenyl; substituted amine XV, wherein at least one of $R_3$, $R_4$, or $R_5$ is —NHCOR$_{11}$, wherein $R_{11}$ is selected from alkyl of 1 to 6 carbon atoms, benzyl, phenyl, alkyl(1 to 6 carbon atoms) phenyl, alkoxy(1 to 6 carbon atoms)phenyl, biphenyl; substituted amine XVI wherein at least one of $R_3$, $R_4$, or $R_5$ is —NHCONHR$_{12}$ wherein $R_{12}$ is benzyl, alkoxy(1 to 6 carbon atoms)phenyl, halophenyl, alkyl(1 to 6 carbon atoms) phenyl can each be prepared by reaction of the amine XIII, respectively with an appropriate alkoxycarbonyl or aryloxycarbonylchloride; acid chloride, or similarly activated acyl compound; or an isocyanate, in an inert solvent, in the presence of an acid scavenger such as triethylamine, at 0° C. to 40° C., for 0.5 h to 24 h.

Scheme VI

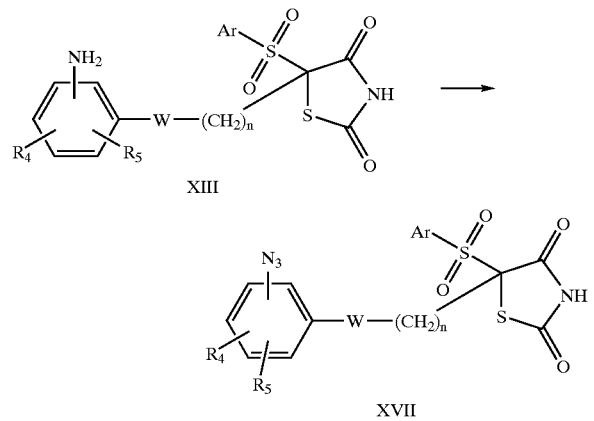

Referring to Scheme VI: compounds of formula (I), wherein at least one of $R_3$, $R_4$, or $R_5$ is the azido group, as in azide XVII may be prepared from amine XIII, by reaction with sodium nitrite in acetic acid at 0° C. to 20° C., for 10 min to 30 min, followed by a metal azide, such as lithium azide for 1 h to 3 h at 10° C. to 25° C.

Scheme VII

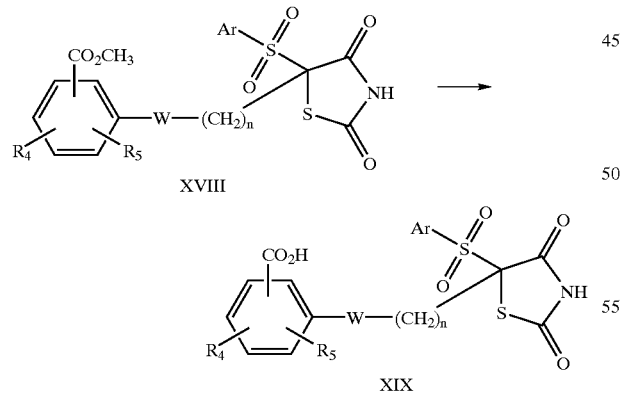

Referring to Scheme VII: compounds of formula (I), wherein at least one of $R_3$, $R_4$, or $R_5$ is a carboxyl group as in carboxylic acid XIX can be prepared from the corresponding ester, such as the methyl ester as in ester XVIII by hydrolysis with a base such as potassium carbonate in a solvent such as methanol, or water, followed by acidification with an acid, such as hydrochloric acid.

Scheme VIII

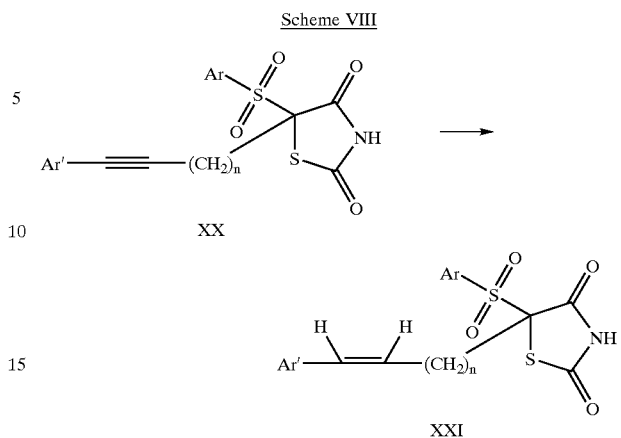

Referring to Scheme VIII: Compounds of Formula (I), wherein Ar' is hereinbefore define and at least one of $R_3$, $R_4$, or $R_5$ are as described above, and W is Z——CH=CH— in alkene XXI may be prepared from the corresponding compounds of formula (I) wherein W is

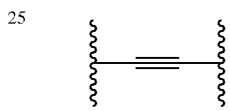

in alkyne XX by reduction with hydrogen and a catalyst, such as platinum or palladium in a solvent such as an alcohol, or THF at 0° to 30° C. for ½ to 8 h;

Scheme IX

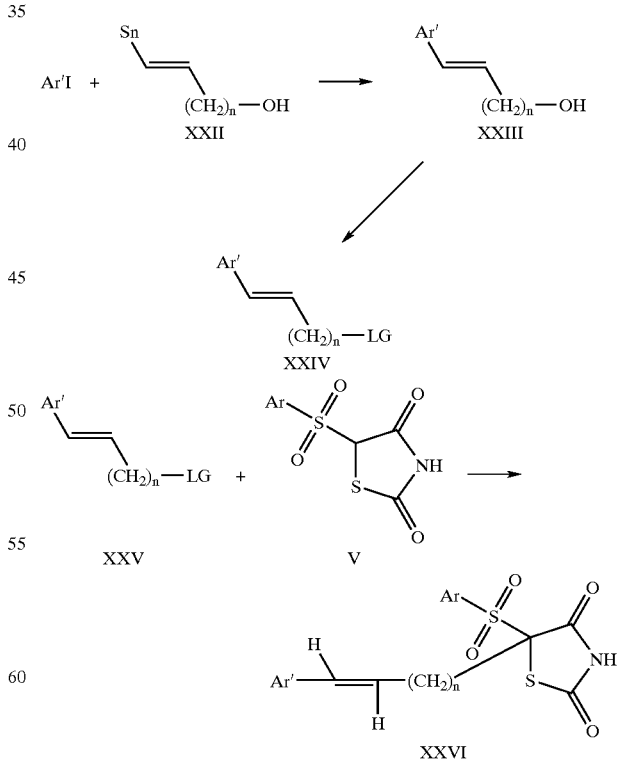

As shown in Scheme IX: compounds of Formula (I) as in alkene XXVI, wherein either $R_3$, $R_4$, and $R_5$ are as previously defined as substituents on Ar', and W is E——CH=CH—, may be prepared by alkylation of 5-arylsulfonylthiazolidine-2,4-dione V with an alkene XXV under conditions as described in Scheme III for the corresponding alkyne. Alkenes XXIV wherein W is E——CH=CH—, can be prepared by coupling an iodophenyl compound where Ar' is hereinbefore defined with an E-stannane XXII in the presence of tetrakistriphenylphosphine palladium(0) and copper(I) iodide in a solvent such as DMF at room temperature for 1 h to 3 days and subsequent conversion to alcohol XXIII to alkene XXIV, wherein LG is iodo, may be accomplished in a manner analogous to that shown in Scheme II. A compound such as XXV, above, wherein LG is a leaving group, such as bromo or iodo is used to alkylate 5-arylsulfonylthiazolidine-2,4-dione V as described herein before in Scheme III.

Scheme X

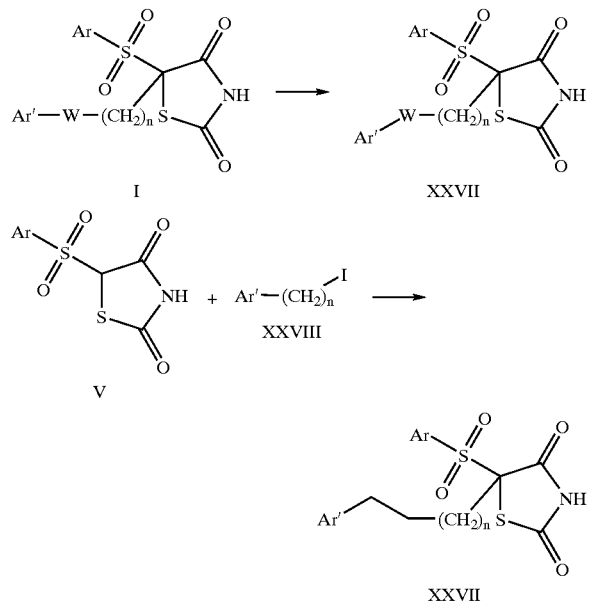

Referring to Scheme X: compounds of formula (I), wherein Ar' is herein before described and W is —CH$_2$—CH$_2$— as in dione XXVII, can be prepared from a compound of formula (I) wherein W is either

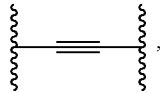

or E— or Z——CH=CH—, by hydrogenation in the presence of palladium or platinum in a solvent such as methanol plus 5% water; alternatively, 5-arylsulfonylthiazolidine-2,4-dione V can be alkylated with XXVIII to give dione XXVII.

Standard Pharmacological Test Procedures

The ability of the compounds of this invention to inhibit FPTase was evaluated in the standard pharmacological in vitro test procedures described below. Data for representative examples is summarized in Table I.

Enzyme test procedure: FPTase inhibition in vitro assay was performed according to James, G. L., Brown, M. S., and Goldstein, J. L., *Methods in Enzymology*, 1995, 255, 38–46; and Garcia, M. A., et al., *J. Biol. Chem.*, 1993, 268, 18415–18420.

Materials—Purified FPTase (Moomaw, J. F. and Casey, P. J., *J. Biol. Chem.*, 1992, 267, 17438–17443), purified His$_6$-Ras, inhibitor compounds at 10 mg/ml or 10 mM in 100% DMSO, $^3$H-FPP (50,000 dpm/pmol) Amersham, TCA/SDS (6%/2%), TCA (6%), Glass fiber filters (0.22–0.45 m), vacuum manifold or 96 well filtration plates.

Methods—1. Dilute FPTase inhibitors from stock solutions to 2.5× in 2.5% DMSO, 10 mM DTT, 0.5% octyl-B-glucoside. 2. Solution #1 is added to FPTase reaction in a volume of 20 ml. 3. Standard reaction mix, 50 ml, contains 50 mM Tris (7.5), 10 mM ZnCl$_2$, 3 mM MgCl$_2$, 20 mM KCl, 5 mM DTT, 0.2% octyl-B-glucoside, 1% DMSO, 40 mM His$_6$-Ras, 10 ng FPTase, and various concentrations of FPTase inhibitors. 4. Incubate for 30–90 min at 250° C. 5. Stop reactions with TCA/SDS (6%/2%), hold at 4° C. for 45–60 min. 6. Filter by manifold or 96 well plate, wash filter 3–5× with TCA (6%). 7. Add scintillant to filters, measure $^3$H-FPP incorporation into Ras protein.

Analysis of Results—Percent inhibition by test compounds is determined by the following:

(cpm from precipitated Ras with test compounds)–(background cpm)×100=% inhibition.

(cpm from precipitated Ras without test compounds)–(background cpm)

Cell-based test procedure: Tumor inhibition in vitro assay was performed according to P. Skehan, R. Storeng, D. Scudiero, A. Monks, J. McMohan, D. Vistica, J. Warren, H. Bokesh, S. Kenney, and M. R. Boyd, *J. Natl. Cancer Instit.*, 1990, 82 (13), 1107–1112; L. V. Rubinstein, R. H. Shoemaker, K. D. Paull, R. M. Simon, S. Tosini, P. Skehan, D. A. Scudiero, A. Monks, and M. R. Boyd, *J. Natl. Cancer Instit.*, 1990, 82 (13), 1113–1118; A. Monks, et al., *J. Natl. Cancer Instit.*, 1991, 83, 757–766; M. R. Boyd and K. D. Paull, *Drug Development Res.*, 1995, 34, 91–109; and S. P. Fricker and R. G. Buckley, *Anticancer Research*, 1996, 16, 3755–3760.

Materials—Cell Lines: Human tumor cell lines LS174T, HTB39, LoVo and CaCo2. Cell Media: RPMI 1640 (or DMEM medium and McCoy's medium) with 10% Fetal Bovine Serum supplemented with L-glutamine and Pennicilin/Streptomycin. Compounds: Supplied usually as a 10 mM stock in 100% DMSO. Normal Saline: 150 mM NaCl Trichloroacetic Acid (TCA): 50% (w/v) in water. Sulforhodamine (SRB): 0.4% (w/v) in 1% Acetic Acid. Tris Base: 10 mM in water.

Methods—Cells are plated at 2000 cells per well, per 200 µl media, and allowed to adhere overnight at 37° C. At 24 h post plating, compounds are added directly at a volume of 0.5 µl. Compound is first diluted in DMSO to generate concentrations of compound or reference standard of: 1, 5, 10 and 25 µM. Dilutions can be made in an identical 96 well plate so that compounds can be added using a multichannel micropipettor set at 0.5 µl. The cells are then incubated for four days after which the media is removed using a 12 well manifold by first tipping the plate forward at a 45 degree angle and then inserting the manifold in an upright orientation to prevent the tips of the manifold from disturbing cells at the bottom of the plate. 200 µl of normal saline is then added to each well using an 8 well multichannel pipettor, followed by the careful addition of 50 µl of 50% TCA. The plates are then incubated for 2 h at 4° C., after which the supernatant is removed using the same technique as above and the plates washed twice with 200 µl water. The plates are then air dried and 50 µl of SRB stock solution is carefully added so that the entire bottom of each well is covered. This again can be used using an 8 well multichannel pipettor. The SRB is incubated with fixed cells for 15 min at room temperature, after which the SRB is removed with the manifold as described above and the plates washed twice with 350 µl of 1% acetic acid per well each time. The plates are then air dried after which the bound SRB is released from protein by the addition of 200 µl of Tris base. Resolubilizing the SRB is aided by placing the plates on a rotator for 15–30 min. The absorbance of each well is determined at 550 or 562 nm using a microtiter plate reader. Analysis of Results—Each compound or dilution thereof is performed in triplicate. Outliers are identified by visual inspection of the data. Each plate should have a control (vehicle only). A standard curve is constructed by plotting the concentration of compound against the average absorbance calculated at that concentration. A curve is plotted and the concentration at which the curve passes through the 50% absorbance mark seen in the control well is the $IC_{50}$ calculated for that compound.

TABLE I in vitro FTase Inhibition Assay

| Ex. No. | $IC_{50}$ H-Ras* µM | $IC_{50}$ K-Ras* µM |
|---|---|---|
| 96 | 0.7 | |
| 97 | 0.075–0.15 | 3.5–5.5 |
| 101 | 0.01–0.03 | 0.11–1.0 |
| 102 | 0.03–0.032 | 1.4 |
| 103 | 0.03–0.05 | 0.9–10 |
| 104 | 0.03–0.054 | 0.23–0.9 |
| 105 | 0.05–0.15 | 1.5–1.7 |
| 106 | 0.23–0.25 | 1.3–1.7 |
| 107 | 0.18–0.2 | 0.62–0.7 |
| 108 | 0.13–0.18 | 9–>10 |
| 109 | 0.065–0.13 | 1.4–2.1 |
| 110 | 0.4 | 7 |
| 111 | 0.11–0.15 | 0.3–0.55 |
| 112 | 0.59–0.60 | 1.4–1.5 |
| 113 | 0.05–0.06 | 0.75–0.8 |
| 114 | 0.013–0.032 | 0.032–0.32 |
| 115 | 0.012–0.32 | 0.16–0.23 |
| 116 | 0.005–0.01 | 0.017–0.04 |
| 117 | 0.02–0.03 | 0.51–1.0 |
| 118 | 0.07 | 1.9 |
| 119 | 0.13–0.14 | 1.3–1.7 |
| 120 | 0.018–0.032 | 0.53–1.0 |
| 121 | 0.12 | 1.6 |
| 122 | 0.03–0.05 | 0.23–1.0 |
| 123 | 0.08–0.082 | 1.0–2.8 |
| 124 | 0.052–0.08 | 0.91–1.3 |
| 125 | 0.03 | 0.4 |
| 126 | 0.09 | 1.7 |
| 127 | 0.12–0.14 | 1.3–1.5 |
| 128 | 0.001–0.032 | 0.02–0.22 |
| 129 | 0.1 | 0.6–0.79 |
| 130 | 0.023–0.056 | 0.32–1.0 |
| 131 | 0.006–0.032 | 0.08–0.31 |
| 132 | 0.041–0.073 | 0.21–1.0 |
| 133 | 0.04–0.2 | 0.054–1.0 |
| 134 | 0.014–0.85 | 0.43–0.68 |
| 135 | 0.02–0.032 | 1.9–2.1 |
| 136 | 0.043–0.05 | 1.0–1.9 |
| 137 | 0.021–0.4 | 0.037–0.8 |
| 138 | 0.023–0.032 | 0.3–0.42 |
| 139 | 0.17–0.14 | 0.6–5.0 |
| 140 | 0.15–0.3 | 1.0–3.6 |
| 141 | 0.021–0.032 | 0.30–0.34 |
| 142 | 0.017–0.03 | 0.04–1.0 |
| 143 | 0.03 | 0.85 |
| 144 | 0.04–0.041 | 0.32–0.55 |
| 145 | 1.2–1.7 | 5.6–10 |
| 147 | 0.0068–0.21 | 0.08–0.1 |
| 148 | 0.0045–0.12 | 0.023–0.031 |
| 149 | 0.45–0.5 | 1.0–4.9 |
| 150 | 0.0074–0.032 | 0.016–0.068 |
| 151 | 0.53–0.7 | 0.21–1.0 |
| 152 | 0.011–0.016 | 0.1–0.23 |
| 153 | 0.17–0.2 | 1.0–6.1 |
| 154 | 0.07–0.15 | 1.0–2.5 |
| 155 | 0.01–0.32 | 0.42–0.44 |
| 157 | 0.27 | 5.0 |
| 158 | 0.15 | 3.8 |
| 159 | 0.65 | >10 |
| 161 | 0.9 | 10 |
| 162 | 1.21 | 4.0 |
| 163 | 1.3 | 10 |
| 164 | 0.15 | >10 |
| 166 | 0.15 | 5.3 |
| 167 | 1.5 | 10 |
| 168 | 0.28 | 10 |
| 169 | 0.1 | 1.8 |
| 170 | 0.38 | 4.7 |
| 171 | 0.2 | 3.3 |
| 175 | 0.01–0.032 | 0.053–0.52 |
| 176 | 0.0032–0.032 | 0.03–0.32 |
| 177 | 0.011–0.032 | 0.086–0.1 |
| 178 | 0.017–0.032 | 0.01 |
| 179 | 0.002–0.032 | 0.005–0.07 |
| 180 | 0.002–0.032 | 0.007–0.09 |
| 181 | 0.01–0.032 | 0.10–0.13 |
| 182 | 0.005–0.01 | 0.032–0.056 |
| 189 | 0.10 | 1.2 |
| 217 | 0.10 | 8.5 |
| 220 | 0.09 | 3.0 |
| 222 | 0.0033 | 0.033 |
| 223 | 0.063 | >1 |
| 226 | 0.03–0.05 | 0.1–3.2 |
| 227 | 0.007–0.01 | 0.21–0.4 |
| 228 | 0.004–0.07 | 0.23–1 |
| 229 | 0.006–0.02 | 0.1–0.7 |
| 230 | 0.003–0.0035 | 0.02–0.5 |
| 231 | 0.01–0.021 | 0.1–1 |
| 232 | 0.005–0.01 | 0.04–0.64 |
| 233 | 2.9 | 10 |

*H-Ras or K-Ras used as substrates for farnesylation

Compounds of this invention were tested in cell-based assays against human tumor cell lines DLD-1 and LoVo and ras-transformed rat fibroblast cell lines, RAT-H-ras and RAT-K-ras, and the parent cell line RAT-2, as described under Assays. The range observed for inhibition of cell growth was $IC_{50}$=7 to 18 µM. The results are displayed in Table I.

Compounds of this invention were tested for in vivo effects in rats against various tumors. For the compound of Example 114, when tested against a K-ras dependent human colon carcinoma (LoVo), the following results were obtained (Table II):

TABLE II

In Vivo Data for the Compound of Example 114

| a<br>Drug<br>Treatment<br>mg/kg<br>per dose | b<br>Day<br>8 | c<br>% T/C | d<br>(p) | b<br>Day<br>15 | c<br>% T/C | d<br>(p) | b<br>Day<br>22 | c<br>% T/C | D<br>(p) | b<br>Day<br>29 | c<br>% T/C | d<br>(p) | b<br>Day<br>36 | c<br>% T/C | d<br>(p) | e<br>S/T |
|---|---|---|---|---|---|---|---|---|---|---|---|---|---|---|---|---|
| 0.5% Methocel 0.4% Tween 80 | 88 | | | 308 | | | 598 | | | 748 | | | 1264 | | | 10/10 |
| Cpd. (100 PO) | 61 | 70 | 0.10 | 238 | 77 | 0.14 | 454 | 76 | 0.08 | 608 | 81 | 0.20 | 934 | 74 | 0.09 | 10/10 |
| Cpd. (75 IP) | 45 | 51 | 0.02 | 110 | 36 | <.01 | 255 | 43 | <.01 | 504 | 67 | 0.09 | 764 | 60 | 0.03 | 8/10 |
| Cpd. (50 IP) | 65 | 74 | 0.15 | 146 | 47 | 0.02 | 258 | 43 | <0.01 | 445 | 59 | 0.07 | 964 | 76 | 0.16 | 5/10 |
| Cpd. (100 IP) | 31 | 35 | <0.01 | 125 | 41 | <.01 | 251 | 42 | <.01 | 341 | 46 | 0.01 | 559 | 44 | 0.01 | 9/10 |
| Vincristine (1 IP) | 14 | 16 | <0.01 | 24 | 8 | <.01 | 84 | 14 | <.01 | 139 | 19 | <0.01 | 194 | 15 | <.01 | 9/10 |
| 2% Tween in D5W | 39 | | | 121 | | | 198 | | | 287 | | | 424 | | | 10/10 |
| Cpd. (75* IP) | 86 | 221 | 0.95 | 182 | 150 | 0.84 | 324 | 163 | 0.92 | 478 | 167 | 0.92 | 666 | 157 | 0.91 | 10/10 |
| 20% BCD in 0.1 N HCl | 62 | | | 146 | | | 339 | | | 499 | | | 813 | | | 10/10 |
| Cpd. (100 PO) | 50 | 81 | 0.22 | 138 | 95 | 0.44 | 299 | 88 | 0.31 | 641 | 128 | 0.77 | 872 | 107 | 0.60 | 9/10 | a) Compound of Example 114(100 IP) administered once a day on days 1 through 20. All other doses of cpd. Were administered on days 1 through 20 BID. Vincristine administered on days 5, 9 and 13. prepared in 2% Tween 80 in D5W.
b) Mean Tumor Weight in mg.
c) % T/C = Mean Tumor Weight of Treated Group × 100 Mean Tumor Weight of Placebo Group
d) Statistical analysis (Student's t-test) of Tumor Weight. A p-value (p ≤ 0.05) indicates a statistical significant reduction in Tumor. Weight of Treated Group, compared to Placebo Control.
e) S/T = No. Survivors/No.Treated on Day +35 post tumor cell implantation Examples 100, and 103, when tested in rats against Rat-2 fibroblasts transformed by oncogenic H-ras for 11 days, i.p., the following results were obtained for day 11 (Table IV):

TABLE III

| Ex. No. | Dose, mg/kg | % T/C |
|---|---|---|
| 100 | 100 | 44 |
| 100 | 30 | 60 |
| 100 | 10 | 100 |
| 103 | 100 | No efficacy at this dose |

$$\% \, TC = \frac{\text{Mean Tumor Weight of Treated Group}}{\text{Mean Tumor Weight of Placebo Group}} \times 100$$

In a similar model when tested in rats against Rat-2 fibroblasts transformed by oncogenic K-ras for 25 days, i.p, the compound of Example 100 showed no efficacy at 100 mg/kg.

Based on the results of these standard pharmacological test procedures, the compounds of this invention are useful as agents for treating, inhibiting or controlling ras-associated diseases by inhibiting farnesyl-protein transferase enzyme, when administered in amounts ranging from about 10 to about 200 mg/kg of body weight per day. A preferred regimen for optimum results would be from about 10 mg to about 100 mg/kg of body weight per day and such dosage units are employed that a total of from about 100 mg to about 1000 mg of the active compound for a subject of about 70 kg of body weight are administered in a 24 hour period.

The dosage regimen for treating mammals may be adjusted to provide the optimum therapeutic response. For example, several divided doses may be administered daily or the dose may be proportionally reduced as indicated by the exigencies of the therapeutic situation. A decidedly practical advantage is that these active compounds may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets or they may be incorporated directly with the food of the diet. For oral therapeutic administration, these active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained. Preferred compositions or preparations according to the present invention are prepared so that an oral dosage unit form contains between 10 and 1000 mg of active compound. The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose, or saccharin may be added or a flavoring agnet such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose, as a sweetening agent, methyl and propylparabens as preservatives, a dye and flavoring such as cherry or orange flavor. Of course, any material used in preparing any dosage unit form should be pharmaceutically pure and substantially non-toxic in the amounts used. In addition, these active compounds may be incorporated into sustained-release preparations and formulations.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures therof in oils. Under ordinary conditions of storage and use, these preparations contain a preservative to prevent the growth or microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and starage and must be prepared against the contaminating action of microorganisms such as bacteria and fungi. The carrier can be a solvent or dispersion medium containing, for example, water, ethanol, polyol (e.g., glycerol, propylene glycol and liquid poly-ethylene glycol), suitable mixtures thereof, and vegetable oils.

The present invention accordingly provides a pharmaceutical composition which comprises a compound of Formula (I) of this invention in combination or association with a pharmaceutically acceptable carrier. In particular, the present invention provides a pharmaceutical composition which comprises an effective amount of a compound of this invention and a pharmaceutically acceptable carrier.

As used in accordance with this invention, the term providing an effective amount of a compound means either directly administering such compound, or administering a prodrug, derivative, or analog which will form an effective amount of the compound within the body.

The present invention provides a method of treatment of ras oncogene-dependent tumors, such as cancers of the pancreas, colon, bladder, and thyroid; a method of controlling metastasis, suppressing angiogenesis, and inducing apoptosis; a method of treating Ras-associated proliferative diseases other than cancer, such as restenosis, neurofibromatosis, endometriosis, and psoriasis. The compounds of the present invention may also inhibit prenylation of proteins other than Ras, and thus provide a method of treatment of diseases associated with other prenyl modifications of proteins.

The invention will be more fully described in conjunction with the following specific examples which are not to be construed as limiting the scope of the invention.

EXAMPLE 1

5-(3-Methoxyphenyl-4-sulfonyl)-thiazolidine-2,4-dione

To a solution of 5-bromothiazolidine-2,4-dione (6.66 g, 34.0 mmol, Zask et al, J. Med. Chem. 1990, 33, 1418–1423) and 3-methoxybenzenethiol (5.00 g,35.7 mmol)in dry THF (150 mL) at −78° C. was added sodium bis(trimethylsilyl) amide (1.0M in THF, 56 mL, 56 mmol) dropwise. After 30 min. the reaction mixture was warmed to room temperature. After an additional hour, 2N HCl was added to pH=1. The layers were separated and the aqueous phase was extracted with ethyl acetate.

The combined organic phase was dried (MgSO4), concentrated and flash chromatographed (3:1 hexanes:ethyl acetate) to provide 5-(3-methoxyphenyl-4-sulfanyl) thiazolidine-2,4-dione, as a white solid (4.86 g, 56%); a sample of 5-(3-methoxyphenyl-4-sulfanyl)-thiazolidine-2,4-dione (4.70 g, 18.4 mmol) was oxidized with 9.4 ml of 30% hydrogen peroxide in 50 ml of acetic acid at 45° C. for 3 hours to give 3.4 g (64%) of the title compound as a glass; NMR(CDCl$_3$)δ3.9 (s,3H), 5.53 (s,1 H), 7.3 (m,1 H), 7.42 (s,1 H), 7.53 (m,2H); MS m/Z 285.9 (M−H) (calcd. For $C_{10}H_9NO_5S_2$)

EXAMPLE 2

5-(4-Fluorophenyl-4-sulfonyl)-thiazolidine-2,4-dione

In the manner of Example 1 above 4-fluorobenzenethiol and bromothiazolidinedione gave 5-(4-fluorophenyl-4-sulfanyl)-thiazolidine-2,4-dione, which on oxidation gave the title compound [U.S. Pat. No. 5,605,918; February 1997; Wrobel, et al.].

EXAMPLE 3

5-(4-Iodophenyl-4-sulfonyl)-thiazolidine-2,4-dione

To a solution of 5-bromothiazolidinedione (5.94 g, 30.3 mmol) in 100 ml of absolute ethanol was added sodium 4-iodophenylsulfinate (9.67 g, 33.3 mmol)and this slurry was stirred for about 18 hours at room temperature. Solvent was removed and the residue was combined with water and was acidified with 2N hydrochloric acid. The organic portion was chromatographed on silica gel with hexanes-ethyl acetate (3:1) to give 5.8 g (50%) of the title compound, mp 190–193° C.

In a like manner to the procedure of Example 3 above, the following aryl sulfinate salts which are either commercially available, or are prepared by the reduction of the corresponding sulfonyl chloride with sodium iodide in acetone (Harwood, Julia, and Thuillier, Tetrahedron, 1980,36, 2483–2487), were reacted with 5-bromothiazolidinedione to give the indicated product, 5-arylsulfonylthiazolidinediones of Examples 4–17:

| EX. No. | SULFINATE SALT | PRODUCT | MELTING POINT ° C. |
|---|---|---|---|
| 4 | Sodium 4-Trifluoro-methoxybenzenesulfinate | 5-(4-Trifluoromethoxy-benzenesulfonyl)thiazol-idine-2,4-dione | 108–110 |
| 5 | Sodium 3-Nitrobenzene sulfinate | 5-(3-Nitrobenzenesulfonyl)-thiazolidine-2,4-dione | 139–140 |

-continued

| EX. No. | SULFINATE SALT | PRODUCT | MELTING POINT ° C. |
|---|---|---|---|
| 6 | Sodium 4-Nitrobenzene sulfinate | 5-(4-Nitrobenzenesulfonyl)-thiazolidine-2,4-dione | 182–183 |
| 7 | Sodium 4-(Pyridin-4-yloxy)benzenesulfinate | 5-[4-(Pyridin-4-yloxy)-benzenesulfonyl]-thiazolidine-2,4-dione | 160 with decomp. |
| 8 | Sodium 4-Phenoxy-benzene-sulfinate | 5-(4-Phenoxybenzene sulfonyl)-thiazolidine-2,4-dione | 160–162 |
| 9 | Sodium 4-Benzyloxy-benzenesulfinate | 5-(4-Benzyloxybenzene-sulfonyl)-thiazolidine-2,4-dione | 190–200 decomp. |
| 10 | Sodium 3,4-Dimethoxy-benzene sulfinate | 5-(3,4-Dimethoxybenzene-sulfonyl)-thiazolidine-2,4-dione | 220–222 |
| 11 | Sodium N-Acetyl-3-amino-4-methoxyphenyl-sulfinate | N-[5-(2,4-Dioxothiazolidine-5-sulfonyl)-2-methoxy-phenyl]-acetamide | 217–219 |
| 12 | Sodium 5-Chloro-thiophene-2-sulfinate | 5-(5-Chloro-thiophene-2-sulfonyl)-thiazolidine-2,4-dione | 133–135 |
| 13 | Sodium Thiophene-2-sulfinate | 5-(Thiophene-2-sulfonyl)-thiazolidine-2,4-dione | 176–177 |
| 14 | Sodium 5-Pyridin-2-yl-thiophene-2-sulfinate | 5-(5-Pyridin-2-yl-thiophene-2-sulfonyl)-thiazolidine-2,4-dione | 168–170 |
| 15 | Sodium 4-Butoxybenzene sulfinate | 5-(4-Butoxybenzenesulfonyl)-thiazolidine-2,4-dione | 120–121 |
| 16 | Sodium 1-Naphthalenyl) sulfinate | 5-[(1-Naphthalenyl)sulfonyl]-2,4-thiazolidinedione | 187–188 |
| 17 | Sodium (8-Quinolinyl) sulfinate | 5-[(8-Quinolinyl)sulfonyl]-2,4-thiazolidinedione | amorphous solid |

EXAMPLE 18

5-(2,5-Dichlorophenyl)pent-4-yn-1-ol

A solution of 1,4-dichloro-2-iodobenzene (20.0 g, 73.3 mmol), 4-pentyn-1-ol (6.17 g, 73.3 mmol), bistriphenylphosphine(Pd II) chloride (1.03 g, 1.47 mmol), and copper(I) iodide (0.14 g, 0.733 mmol) in 400 ml of diethylamine was stirred under nitrogen for three days. This was diluted with dichloromethane and the oily layer was adsorbed onto silica gel and eluted with hexanes-ethyl acetate (5:1) to give 5-(2,5-dichloro-phenyl)pent-4-yn-1-ol, 13.7 g (82%); NMR (CDCl3) δ1.9 (m,2H), 2.6 (t,2H), 3.85 (t,2H), 7.2 (dd,1 H), 7.28 (m,1 H), 7.4 (d,2H).

EXAMPLE 19

5-(4-Methanesulfonylphenyl)pent-4-yn-1-ol

Preparation of the title compound with 4-bromophenyl methyl sulphone (5.87 g, 25 mmol) and 4-pentyn-1-ol (2.1 g, 25 mmol) according to the procedure in example 18 yielded 5.12 g (87%) of yellow oil which was characterized as 5-(4-Methanesulfonylphenyl)pent-4-yn-1-ol: NMR (CDCl$_3$) δ 1.88–1.93 (m,2H), 2.56–2.60 (t, J=6.99, 2H), 3.04 (s,3H), 3.80–3.84 (t, J=6.15,2H), 7.56 (d, J=5.1,2H), 7.85 (d,J=4.8,2H). MS m/Z 239 (M+H cald. for $C_{12}H_{14}O_3S$ 238.3)

In a manner described in Example 19 immediately above the following acetylenic alcohols of Examples 20–48 were prepared from the corresponding iodobenzene or bromobenzene and 4-pentyn-1-ol (structures were confirmed as above by NMR):

| EX. No. | PRODUCT | Mass Spectrum M+ |
|---|---|---|
| 20 | 5-(2-Methyl-5-nitrophenyl)pent-4-yn-1-ol | 220 (M + H) |
| 21 | 5-(2-Methoxy-5-nitrophenyl)pent-4-yn-1-ol | 235.0 |
| 22 | 5-(2-Methoxy-4-nitrophenyl)pent-4-yn-1-ol | 235.0 |
| 23 | 5-(4-Nitro-2-trifluoromethylphenyl)pent-4-yn-1-ol | 273.0 |
| 24 | 5-(3-Fluoro-5-nitrophenyl)pent-4-yn-1-ol | 223.0 |
| 25 | 5-(3-Fluoro-4-methoxy-5-nitrophenyl)pent-4-yn-1-ol | 254.2 (M + H) |
| 26 | 5-(4-Methoxy-2-nitrophenyl)pent-4-yn-1-ol | 234.2 (M + H) |
| 27 | [3-Chloro-4-(5-hydroxypent-1-ynyl)phenyl]-carbamic Acid tert-Butyl Ester | |
| 28 | 5-(4-Pyrrol-1-ylphenyl)pent-4-yn-1-ol | 226.2 (M + H) |
| 29 | 5-(2,5-Dimethylphenyl)pent-4-yn-1-ol | 189.1 (M + H) |
| 30 | 5-(5-Chloro-2-methylphenyl)pent-4-yn-1-ol | 208.8 (M + H) |
| 31 | 5-(4-Chloro-2-methylphenyl)pent-4-yn-1-ol | 208.0 |
| 32 | 5-(2,4-Dimethylphenyl)pent-4-yn-1-ol | 188.1 |
| 33 | 5-(2-Methyl-4-nitrophenyl)pent-4-yn-1-ol | 219.0 |
| 34 | 5-(4-Bromo-2-methylphenyl)pent-4-yn-1-ol | 253.0 |
| 35 | 3-(5-Hydroxypent-1-ynyl)-4-methylbenzoic Acid Methyl Ester | 232.1 |
| 36 | 4-(5-Hydroxypent-1-ynyl)-3-methylbenzoic Acid Methyl Ester | 232.1 |
| 37 | 5-(4-tert-Butylphenyl)pent-4-yn-1-ol | |
| 38 | [4-Methyl-3-(5-hydroxypent-1-ynyl)phenyl] carbamic Acid tert-Butyl Ester | |

-continued

| EX. No. | PRODUCT | Mass Spectrum M+ |
|---|---|---|
| 39 | 5-(2-Chlorophenyl)pent-4-yn-1-ol | |
| 40 | 5-(2,4-Dichlorophenyl)pent-4-yn-1-ol | |
| 41 | 4-(5-Hydroxypent-1-ynyl)trifluoromethyl benzene | |
| 42 | 4-(5-Hydroxypent-1-ynyl)trifluoromethoxy-benzene | |
| 43 | [3-Methyl-4-(5-hydroxypent-1-ynyl)phenyl] carbamic Acid tert-Butyl Ester | |
| 44 | N-tert-Butyl-3-(5-hydroxypent-1-ynyl)-4-methylbenzamide | |
| 45 | 4-(5-Hydroxypent-1-ynyl)phenylcarbamic Acid tert-Butyl Ester | |
| 46 | 3-(5-Hydroxypent-1-ynyl)-4-methylbenzoic Acid Methyl Ester | |
| 47 | 5-(4-Chlorophenyl)pent-4-yn-1-ol | |
| 48 | 5-(3-Chlorophenyl)pent-4-yn-1-ol | |

EXAMPLE 49

6-(4-Chlorophenyl)hex-5-yn-1-ol

In a manner described in Example 18 above, 5-hexyn-1-ol was reacted with 1-chloro-4-iodobenzene to give the title compound, MS m/Z exact mass 209.724 (M+H)(calcd. For $C_{12}H_{13}OCl$ 209.70).

EXAMPLE 50

11-(4-Chlorophenyl)undec-10-yn-1-ol

In a manner described in Example 18 above, 10-undecene-1-ol was reacted with 1-chloro-4-iodobenzene to give the title compound; NMR (CDCl$_3$) δ1.21–1.50 (m, 10H), 1.50–1.65 (m, 4H), 2.36–2.41 (m,2H), 3.61–3.66(m, 2H), 7.16–7.31 (m, 4H).

EXAMPLE 51

3-(4-Phenoxyphenyl)prop-2-yn-1-ol

Preparation of the title compound with commercial available 4-bromo-diphenyl ether (5.93 g, 23.8 mmol) according to the procedure in example 18 yielded 440 mg (8.2%) of brown oil which was characterized as 3-(4-phenoxyphenyl) prop-2-yn-1-ol: NMR (CDCl$_3$) δ4.50 (d, J=6), 6.91 (d, J=2.01, 1H), 6.93 (d, J=2.01, 1H), 7.01 (d, J=0.63, 1H),7.04 (d, J=1.17, 1H), 7.11–7.16 (m, 1H),7.36 (d, J=0.6, 1H), 7.38 (d, J=2.52, 2H), 7.41 (d, J=1.92, 1H). MS m/z 224.08 (M+calcd. for $C_{15}H_{12}O_2$=224.08).

EXAMPLE 52

3-Biphenyl-4-yl-prop-2-yn-1-ol

In a manner described in Example 18 above, propargyl alcohol was reacted with 4-bromobiphenyl to give the title compound as white crystals: NMR (CDCl$_3$) δ 4.53 (d, J=4.74, 2H), 7.38 (d, J=7.17, 1H), 7.42–7.60 (m, 8H). MS m/z 208 (M+ calcd. for $C_{15}H_{12}O$=208.3).

EXAMPLE 53

3-Thiophene-2-yl-prop-2-yn-1-ol

In a manner described in Example 18 above, propargyl alcohol was reacted with 2-bromothiophene to give the title compound as a brown oil which was used in the next step without further purification.

EXAMPLE 54

1-Chloro-4-(5-iodopent-1-ynyl)benzene 5-(4-Chlorophenyl)pent-4-yn-1-ol (35.7 g, 182 mmol), 4-dimetylamino-pyridine (8.9 g, 73 mmol), p-toluenesulfonyl chloride (34.7 g, 182 mmol), and 62 ml of triethylamine were combined in 330 ml of dichloromethane at 0° C. The mixture was stirred for 30 min. at 0° then 18 hours at room temperature. Dilution with 200 ml of dichloromethane followed by washing with brine, drying over magnesium sulfate, filtration through silica gel with hexane-ethyl acetate, 8:1, gave a yellow solid on evaporation. Crystallization from ether gave 5-(4-Chlorophenyl)pent-4-yn-1-ol p-toluenesulfonate as colorless crystals (31.7 g, 49% yield). This was converted to the title compound by reaction with sodium iodide in acetone, and was used in subsequent reactions with no further purification; MS m/z 303.9 (M+ calcd. for $C_{11}H_{10}ClI$=304.6).

EXAMPLE 55

1-(5-Iodo-pent-1-ynyl)-4-methanesulfonylbenzene

Preparation of the title compound with tosylated alcohol of example 19, 5-(4-methanesulfonylphenyl)pent-4-yn-1-ol (3.14 g, 8.35 mmol), NaI (6.26 g, 41.76 mmol) following the procedure of Example 54 yielded 2.8 g (96%) of the title compound as a red oil: NMR (CDCl$_3$) δ 2.06–2.15 (m, 2H), 2.58–2.63 (t, J=6.78, 2H), 3.04 (s, 3H), 3.33–3.37 (t, J=6.69, 2H), 7.57 (d, J=1.77, 2H), 7.85 (d, J=4.95, 2H), MS m/z 348.9 (M+H cald. for $C_{12}H_{13}IO_2S$ 348=349.2).

EXAMPLE 56

1,4-Dichloro-2-(5-iodopent-1-ynyl)benzene 5-(2,5-Dichlorophenyl)pent-4-yn-1-ol (13.7 g, 59.8 mmol), triphenylphosphine (20.4 g, 77.8 mmol), and imidazole (5.71 g, 83.8 mmol) in a mixed solvent (100 ml acetonitrile-150 ml ether) was stirred under nitrogen at 0° C., and to this was slowly added iodine (21.3 g, 83.8 mmol). The solution was allowed to warm to room temperature and stirring was continued for 18 hours. This was chromatographed on silica gel with hexane to give the title compound (14.7 g,72%), MS m/z 337.9 (M–H calcd. for $C_{11}H_9Cl_2I$= 338.0).

In the manner described in Example 55, above, the following alcohols were converted to the corresponding iodides of Examples 56–88, and structures were confirmed as above by NMR:

| EX. No. | ALCOHOL | PRODUCT | MASS SPECTRUM |
|---|---|---|---|
| 56 | 5-(2,4-Dichlorophenyl)-pent-4-yn-1-ol | 1,5-Dichloro-2-(5-iodo-pent-1-ynyl)benzene | 337.9 |
| 57 | 5-(2-Methyl-5-nitro-phenyl)pent-4-yn-1-ol | 2-(5-Iodopent-1-ynyl)-1-methyl-4-nitro-benzene | 330 |
| 58 | 5-(2-Methoxy-5-nitro-phenyl)pent-4-yn-1-ol | 2-(5-Iodopent-1-ynyl)-1-methoxy-4-nitro-benzene | 345.1 |
| 59 | 5-(2-Methoxy-4-nitro-phenyl)pent-4-yn-1-ol | 1-(5-Iodopent-1-ynyl)-2-methoxy-4-nitro-benzene | 345.0 |
| 60 | 5-(4-Nitro-2-trifluoro-methyl-phenyl)pent-4-yn-1-ol | 1-(5-Iodopent-1-ynyl)-4-nitro-2-trifluoro-methylbenzene | 383.0 |
| 61 | 5-(3-Fluoro-5-nitro-phenyl)pent-4-yn-1-ol | 1-Fluoro-3-(5-iodopent-1-ynyl)-5-nitrobenzene | 334 |
| 62 | 5-(3-Fluoro-4-methoxy-5-nitrophenyl)pent-4-yn-1-ol | 1-Fluoro-5-(5-iodopent-1-ynyl)-2-methoxy-3-nitrobenzene | |
| 63 | 5-(4-Methoxy-2-nitro-phenyl)pent-4-yn-1-ol | 1-(5-Iodopent-1-ynyl)-4-methoxy-2-nitro-benzene | |
| 64 | [3-Chloro-4-(5-hydroxy-pent-1-ynyl)-phenyl]-carbamic acid tert-butyl ester | [3-Chloro-4-(5-iodo-pent-1-ynyl)phenyl]-carbamic acid tert-butyl ester | [mp 104–106° C.] |
| 65 | 5-(4-Pyrrol-1-yl-phenyl)-pent-4-yn-1-ol | 1-[4-(5-Iodopent-1-ynyl)-phenyl]-1H-pyrrole | 335.7 |
| 66 | 5-(2,5-Dimethylphenyl)-pent-4-yn-1-ol | 1-(5-Iodopent-1-ynyl)-2,5-dimethyl-benzene | 298.0 |
| 67 | 5-(5-Chloro-2-methyl-phenyl)-pent-4-yn-1-ol | 4-Chloro-2-(5-iodopent-1-ynyl)-1-methyl-benzene | 317.9 |
| 68 | 5-(4-Chloro-2-methyl-phenyl)pent-4-yn-1-ol | 4-Chloro-1-(5-iodopent-1-ynyl)-2-methyl-benzene | 317.9 |
| 69 | 5-(2,4-Dimethyl-phenyl)pent-4-yn-1-ol | 1-(5-Iodopent-1-ynyl)-2,4-dimethyl-benzene | 298.0 |
| 70 | 5-(2-Methyl-4-nitro-phenyl)-pent-4-yn-1-ol | 1-(Iodopent-1-ynyl)-2-methyl-4-nitrobenzene | 328.9 |
| 71 | 5-(4-Bromo-2-methyl-phenyl)pent-4-yn-1-ol | 4-Bromo-1-(5-iodopent-1-ynyl)-2-methyl-benzene | 361.9 |
| 72 | 3-(5-Hydroxypent-1-ynyl)-4-methylbenzoic acid methyl ester | 3-(5-Iodopent-1-ynyl)-4-methylbenzoic acid methyl ester | 341.9 |
| 73 | 4-(5-Hydroxy-pent-1-ynyl)-3-methylbenzoic acid methyl ester | 3-(5-Iodopent-1-ynyl)-4-methylbenzoic Acid Methyl Ester | 341.9 |
| 74 | [4-Methyl-3-(5-hydroxypent-1-ynyl)phenyl]carbamic acid tert-butyl ester | [3-(5-Iodopent-1-ynyl)-4-methylphenyl]carbamic acid tert-butyl ester | 399.9 |
| 75 | 5-(2-Chlorophenyl)-pent-4-yn-1-ol | 1-Chloro-2-(5-iodopent-1-ynyl)benzene | 304.0 |
| 76 | 5-(2,4-Dichlorophenyl)pent-4-yn-1-ol | 2,4-Dichloro-1-(5-iodo-pent-1-ynyl)benzene | 337.9 |
| 77 | 4-(5-Hydroxypent-1-ynyl)trifluoromethyl-benzene | 1-(5-Iodopent-1-ynyl)-4-trifluoromethylbenzene | 337.9 |
| 78 | 4-(5-Hydroxypent-1-ynyl)trifluoromethoxy-benzene | 1-(5-Iodopent-1-ynyl)-4-trifluoromethoxy-benzene | |
| 79 | [3-Methyl-4-(5-hydroxypent-1-ynyl)-phenyl]carbamic Acid tert-Butyl Ester | [4-(5-Iodopent-1-ynyl)-3-methylphenyl]carbamic Acid tert-Butyl Ester | 399.9 |
| 80 | N-tert-Butyl-3-(5-hydroxypent-1-ynyl)-4-methylbenzamide | N-tert-Butyl-3-(5-iodo-pent-1-ynyl)-4-methyl-benzamide | 383.8 |
| 81 | 4-(5-hydroxypent-1-ynyl)phenylcarbamic Acid tert-Butyl Ester | [4-(5-Iodopent-1-ynyl)-phenyl]carbamic Acid tert-Butyl Ester | 385.9 |
| 82 | 3-(5-Hydroxypent-1-ynyl)-4-methylbenzoic Acid Methyl Ester | 3-(5-Iodopent-1-ynyl)-4-methylbenzoic Acid Methyl Ester | |
| 83 | 5-(3-Nitrophenyl)pent-4-yn-1-ol | 1-(5-Iodopent-1-ynyl)-3-nitrobenzene | 315.8 |
| 84 | 5-(4-Nitrophenyl)pent-4-yn-1-ol | 1-(5-Iodopent-1-ynyl)-4-nitrobenzene | 315.9 |
| 85 | 5-(4-tert-Butylphenyl) pent-4-yn-1-ol | 1-tert-Butyl-4-(5-iodo-pent-1-ynyl)benzene | 326.0 |
| 86 | 5-(3-Chlorophenyl) pent-4-yn-1-ol | 1-Chloro-3-(5-iodopent-1-ynyl)benzene | 304.0 |
| 87 | 6-(4-Chlorophenyl)hex-5-yn-1-ol | 1-(4-Chlorophenyl)-6-iodo-1-hexyne | |

| EX. No. | ALCOHOL | PRODUCT | MASS SPECTRUM |
|---|---|---|---|
| 88 | 11-(4-Chlorophenyl)-undec-10-yn-1-ol | 1-(4-Chlorophenyl)-11-iodo-1-undecyne | |

EXAMPLE 89

1-(3-Bromo-1-propynyl)-4-phenoxybenzene

A solution of 3-(4-phenoxyphenyl)prop-2-yn-1-ol of Example 51 (415 mg, 1.85 mmol), triphenylphosphine (514 mg, 1.96 mmol), carbon tetrabromide (650 mg, 1.96 mmol) in THF (3 ml) was stirred at room temperature for 3 days. Evaporation of the solution, and chromatography of the residue gave the title compound as a brown oil: NMR (CDCl$_3$) δ 4.16 (s, 2H), 6.91 (d, J=2.1, 1H), 6.93 (d, J=2.1, 1H), 7.01 (d, J=0.93, 1H), 7.04 (d, J=1.14, 1H), 7.12–7.17 (m, 1H), 7.36 (d, J=0.75, 1H), 7.39 (d, J=1.98, 2H), 7.42 (d, J=2.64, 1H). MS m/z 288 (M+1 calcd. for C$_{15}$H$_{11}$BrO 287.155).

In the manner described in Example 89, above, the following alcohols were converted to the corresponding bromides of Examples 90–91:

| EX. No. | ALCOHOL | PRODUCT | Mass spectrum |
|---|---|---|---|
| 90 | 3-Thiophene-2-ylprop-2-yn-1-ol | 2-(3-Bromoprop-1-ynyl)-thiophene | 201.9 (M + H) |
| 91 | 3-Biphenyl-4-ylprop-2-yn-1-ol | 4-(3-Bromoprop-1-ynyl)-biphenyl | 270 (M − H) |

EXAMPLE 92

5-[5-(4-Chlorophenyl)pent-4-ynyl]-5-(4-methoxyphenylsulfanyl)- thiazolidine-2,4-dione To a solution of 5-(4-methoxyphenyl-4-sulfanyl) thiazolidine-2,4-dione [U.S. Pat. No. 5,605,918; February 1997; Wrobel, et al.](1.00 g, 3.92 mmol)in THF (40 ml) was added NaH (0.34 g, 8.62 mmol)at 0° C. and stirring was continued for 30 minutes. To this was added a solution of 1-(4-chlorophenyl)-5-iodo-1-pentyne (1.25 g, 4.12 mmol)in 3 ml of THF. This was then stirred at room temperature for 18 hours, and then quenched in water. The resultant oil was chromatographed on silica gel using hexane:ethyl acetate (4:1) to give the title compound as a pale yellow solid, m.p. 106–109° C.

In the manner described in Example 92 immediately above, the appropriate substituted alkyl iodide was reacted with a substitutedphenyl thiazolidinedione to give the following compounds of Examples 93–96:

EXAMPLE 93

5-[6-(4-Chlorophenyl)hex-5-ynyl]-5-(4-methoxyphenylsulfanyl)-thiazolidine-2,4-dione MS m/z 444.2 (calcd for C$_{22}$H$_{20}$ClNO$_3$S$_2$ 445.99).

EXAMPLE 94

5-[11-(4-Chlorophenyl)undec-10-ynyl]-5-(4-methoxy-phenylsulfanyl)-thiazolidine-2,4-dione mp 54–56° C., MS m/z 514.0 (calcd. for C$_{27}$H$_{30}$ClNO$_3$S 516.1).

EXAMPLE 95

5-(4-Methoxyphenylsulfanyl)-5-(5-thiophen-2-yl-pent-4-ynyl)-thiazolidine-2,4-dione This was used in the next step without further purification.

EXAMPLE 96

5-[5-(4-Chlorophenyl)pent-4-ynyl]-5-(4-fluorophenylsulfanyl)-thiazolidine-2,4-dione This was used in the next step without further purification.

EXAMPLE 97

5-[5-(4-Chlorophenyl)pent-4-ynyl]-5-(4-methoxyphenylsulfonyl)-thiazolidine-2,4-dione To a solution of 5-[5-(4-Chlorphenyl)pent-4-ynyl]-5-(4-methoxyphenylsulfanyl)-thiazolidine-2,4-dione of Example 92 above,(0.87 g, 2.0 mMol) in glacial acetic acid (30 ml)at 60° C was added 30% hydrogen peroxide (0.82 ml, 8.0 mmol). After 30 minutes the reaction mixture was evaporated and the residue was subjected to chromatography to give the title compound, MS (M–H) m/z 462.0 (calcd. For C$_{21}$H$_{18}$ClNO$_5$S$_2$463.96).

EXAMPLE 98

5-[6-(4-Chlorophenyl)hex-5-ynyl]-5-(4-methoxyphenylsulfonyl)-thiazolidine-2,4-dione 5-[6-(4-Chlorophenyl)hex-5-ynyl]-5-(4-methoxyphenylsulfanyl)-thiazolidine-2,4-dione (0.30 g, 0.81 mmol) and isobutyraldehyde (0.37 ml, 4.04 mmol) were dissolved in acetonitrile (40 ml). Oxygen was bubbled through this solution for 18 hours, and then the solution was evaporated and the residue was subjected to chromatography on silica gel (hexane-ethyl acetate, 1:1) to give 0.108 g, 28% yield of the title compound, mp 145–148° C., MS m/z 476.0.

EXAMPLE 99

5-[11-(4-Chlorophenyl)undec-10-ynyl]-5-(4-methoxyphenylsulfonyl)-thiazolidine-2,4-dione 5-[11-(4-Chlorophenyl)undec-10-ynyl]-5-(4-methoxyphenylsulfanyl)-thiazolidine-2,4-dione was converted to the title compound using the procedure of Example 98 immediately above, mp 114–121° C.

EXAMPLE 100

5-[5-(4-Chlorophenyl)pent-4-ynyl]-5-(4-methoxyphenylsulfonyl)- thiazolidine-2,4-dione To a solution of 5-(4-methoxyphenylsulfonyl)-thiazolidine-2,4-dione [U.S. Pat. No. 5,605,918; February 1997; Wrobel, et al.]((2.74 g, 9.5 mMol) in DMF (50 ml) was added sodium hexamethyldisilazane (1.0 M solution in THF-19.0 ml, 19.0 mmol) at room temperature, under nitrogen, and this was stirred for 15 minutes. To this was added 1-(4-chlorophenyl)-5-iodo-1-pentyne (2.70 g, 9.5 mmol) over 5 minutes, and this solution was stirred overnight at room temperature. The reaction mixture was quenched in water, and the solid that was obtained was recrystallized from methanol to give 1.59 g of the title compound as colorless crystals, m.p. 172–174°; NMR (CDCl$_3$) δ1.59 (m, 1H); 2.0(m, 1H); 2.36 (dq (doublet of quartets?), 1H); 2.5 (t, 2H); 2.67 (dq, 1H); 3.88 (s, 3H); 7.0 (d, 2H); 7.26 (s, 4H) 7.86 (d, 2H) In a manner essentially that of Example 100, the following products of Examples 101–171 were obtained by alkylation of an arylthiazolidine-2,4-dione with the appropriate iodo or bromo compound. All structures were verified by NMR and gave spectra consistent with that shown in Example 100:

| Ex. No. | Product | melting point ° C. | mass spectrum m/z (M − H) |
|---|---|---|---|
| 101 | 5-[5-(2-Chlorophenyl)pent-4-ynyl]-5-(4-methoxybenzenesulfonyl)-thiazolidine-2,4-dione | 133–135 | 463.0 |
| 102 | 5-[5-(3-Chlorophenyl)pent-4-ynyl]-5-(4-methoxybenzenesulfonyl)-thiazolidine-2,4-dione | 134–136 | 463.0 |
| 103 | 5-[5-(4-Chlorophenyl)pent-4-ynyl]-5-(p-tolylsulfonyl)-thiazolidine-2,4-dione | 176–177 | 447.0 |
| 104 | 5-[5-(4-Chlorophenyl)pent-4-ynyl]-5-(4-iodobenzenesulfonyl)-thiazolidine-2,4-dione | 157–159 | 558.8 |
| 105 | 5-[5-(4-Chlorophenyl)pent-4-ynyl]-5-(4-fluorobenzenesulfonyl)-thiazolidine-2,4-dione | | 450.9 |
| 106 | 5-[5-(4-Chlorophenyl)pent-4-ynyl]-5-(4-phenoxybenzenesulfonyl)-thiazolidine-2,4-dione | 193–194 | 525.0 |
| 107 | 5-[5-(4-Chlorophenyl)pent-4-ynyl]-5-(naphthalene-2-sulfonyl)-thiazolidine-2,4-dione | 150–153 | 483.0 |
| 108 | N-(4-{5-[5-(4-Chlorophenyl)pent-4-ynyl]-2,4-dioxothiazolidine-5-sulfonyl}phenyl)acetamide | 232 decomp. | 490.0 |
| 109 | 5-[5-(4-Chlorophenyl)pent-4-ynyl]-5-(quinoline-8-sulfonyl)-thiazolidine-2,4-dione | pale yellow solid | 484.0 |
| 110 | 5-[5-(4-Chlorophenyl)pent-4-ynyl]-5-(4-nitrobenzenesulfonyl)-thiazolidine-2,4-dione | Tan solid | 477.9 |
| 111 | 5-(4-Benzyloxybenzenesulfonyl)-5-[5-(4-chlorophenyl)pent-4-ynyl]-thiazolidine-2,4-dione | 181–184 | 539.0 |
| 112 | 5-(4-Butoxybenzenesulfonyl)-5-[5-(4-chlorophenyl)-pent-4-ynyl]-thiazolidine-2,4-dione | 116–118 | 505.0 |
| 113 | 5-[5-(4-Chlorophenyl)pent-4-ynyl]-5-(naphthalene-1-sulfonyl)-thiazolidine-2,4-dione | 172–174 | 483.0 |
| 114 | 5-[5-(2,5-Dichloro-phenyl)pent-4-ynyl]-5-(4-methoxy-benzenesulfonyl)-thiazolidine-2,4-dione | 124–126 | 497.4 |
| 115 | 5-[5-(2,5-Dichloro-phenyl)pent-4-ynyl]-5-(4-iodobenzenesulfonyl)-thiazolidine-2,4-dione | yellow amorphous solid | 593.3 |
| 116 | 5-[5-(2,5-Dichlorophenyl)pent-4-ynyl]-5-[4-(pyridin-4-yloxy)benzenesulfonyl]-thiazolidine-2,4-dione | 179–180 decomp. | 560.5 |
| 117 | 5-[5-(2,4-Dichlorophenyl)pent-4-ynyl]-5-(4-methoxybenzenesulfonyl)-thiazolidine-2,4-dione | 129–133 | 497.4 |
| 118 | 5-(4-Methoxybenzenesulfonyl)-5-[5-(3-nitrophenyl)pent-4-ynyl]-thiazolidine-2,4-dione | 126–130 | 473.5 |
| 119 | 5-[5-(3-Nitrophenyl)pent-4-ynyl]-5-(4-phenoxybenzenesulfonyl)-thiazolidine-2,4-dione | 190–191 | 535.6 |
| 120 | 5-(4-Iodobenzenesulfonyl)-5-[5-(4-nitrophenyl)pent-4-ynyl]-thiazolidine-2,4-dione | 205–207 | 569.4 |
| 121 | 5-(4-Methoxybenzene sulfonyl)-5-[5-(4-nitrophenyl)pent-4-ynyl]-thiazolidine-2,4-dione | 156–158 | 473.5 |

-continued

| Ex. No. | Product | melting point °C. | mass spectrum m/z (M − H) |
|---|---|---|---|
| 122 | 5-(4-Methoxybenzene sulfonyl)-5-[5-(2-methyl-5-nitrophenyl)pent-4-ynyl]-thiazolidine-2,4-dione | yellow oil | 487.5 |
| 123 | 5-(4-Methoxybenzenesulfonyl)-5-[5-(2-methoxy-5-nitrophenyl)pent-4-ynyl]-thiazolidine-2,4-dione | orange solid | 503.5 |
| 124 | 5-[5-(2-Methyl-5-nitrophenyl)pent-4-ynyl]-5-(4-phenoxybenzenesulfonyl-thiazolidine-2,4-dione | 203–204 | 549.6 |
| 125 | 5-(4-Iodobenzenesulfonyl)-5-[5-(2-methyl-5-nitrophenyl)pent-4-ynyl]-thiazolidine-2,4-dione | 188–190 | 583.4 |
| 126 | 5-[5-(2-Methyl-5-nitrophenyl)-pent-4-ynyl]-5-(naphthalene-1-sulfonyl)-thiazolidine-2,4-dione | 168–172 | 507.6 |
| 127 | 5-[5-(2-Methyl-5-nitrophenyl)pent-4-ynyl]-5-(naphthalene-2-sulfonyl)-thiazolidine-2,4-dione | 197–200 | 507.6 |
| 128 | 5-[5-(2-Methyl-4-nitrophenyl)pent-4-ynyl]-5-[4-(pyridin-4-yloxy)-benzenesulfonyl]-thiazolidine-2,4-dione | 199 decomp. | 572.6 |
| 129 | 5-[5-(2-Methyl-4-nitrophenyl)pent-4-ynyl]-5-(4-phenoxybenzenesulfonyl)-thiazolidine-2,4-dione | 210–212 | 549.6 |
| 130 | 5-(4-Methoxybenzenesulfonyl)-5-[5-(2-methyl-4-nitrophenyl)-pent-4-ynyl]-thiazolidine-2,4-dione | yellow glass | 487.5 |
| 131 | 5-(4-Iodobenzenesulfonyl)-5-[5-(2-methyl-4-nitrophenyl)pent-4-ynyl]-thiazolidine-2,4-dione | 150–152 | 657.5 |
| 132 | 5-(4-Methoxybenzenesulfonyl)-5-[5-(2-methoxy-4-nitrophenyl)pent-4-ynyl]-thiazolidine-2,4-dione | yellow gum | 503.5 |
| 133 | 5-[5-(3-Fluoro-5-nitrophenyl)pent-4-ynyl]-5-(4-methoxybenzene-sulfonyl)-thiazolidine-2,4-dione | white solid | 491.5 |
| 134 | 5-[5-(2,5-Dimethylphenyl)pent-4-ynyl]-5-(4-iodobenzenesulfonyl)-thiazolidine-2,4-dione | 129–130 | 552.4 |
| 135 | 5-[5-(2,5-Dimethylphenyl)pent-4-ynyl]-5-(4-methoxybenzenesulfonyl)-thiazolidine-2,4-dione | 149–150 | 456.6 |
| 136 | 5-[5-(2,4-Dimethylphenyl)pent-4-ynyl]-5-(4-methoxybenzenesulfonyl)-thiazolidine-2,4-dione | 155–156 | 456.6 |
| 137 | 5-[5-(2,4-Dimethylphenyl)pent-4-ynyl]-5-(4-iodobenzenesulfonyl)-thiazolidine-2,4-dione | 153–154 | 552.4 |
| 138 | 5-[5-(5-Chloro-2-methylphenyl)pent-4-ynyl]-5-(4-methoxybenzene-sulfonyl)thiazolidine-2,4-dione | 121–122 | 477.0 |
| 139 | 5-[5-(5-Chloro-2-methylphenyl)pent-4-ynyl]-5-(4-trifluoromethoxybenzene-sulfonyl)thiazolidine-2,4-dione | 196 decomp. | 549.0 |
| 140 | 5-[5-(4-Chloro-2-methylphenyl)pent-4-ynyl]-5-(4-trifluoromethoxy-benzenesulfonyl)thiazolidine-2,4-dione | 197 decomp. | 559.9 |
| 141 | 5-[5-(4-Chloro-2-methylphenyl)-pent-4-ynyl]-5-(4-iodobenzene-sulfonyl)-thiazolidine-2,4-dione | 93–99 | 591.4 |
| 142 | 5-[5-(4-Chloro-2-methylphenyl) pent-4-ynyl]-5-(4-methoxybenzene-sulfonyl)-thiazolidine-2,4-dione | yellow foam | 477.0 |
| 143 | 5-[5-(4-Bromo-2-methy-phenyl)pent-4-ynyl]-5-(4-methoxybenzene-sulfonyl)-thiazolidine-2,4-dione | white foam | 540.0 |
| 144 | 5-[5-(4-Bromo-2-methylphenyl)pent-4-ynyl]-5-(4-iodobenzenesulfonyl)-thiazolidine-2,4-dione | 146–147 | 617.3 |
| 145 | (4-{5-[5-(4-Methoxybenzensulfonyl)-2,4-dioxothiazolidin-5-yl]pent-1-ynyl}phenyl)carbamic Acid tert-Butyl Ester | yellow solid | 543.7 |
| 146 | (3-Chloro-4-{5-[5-(4-methoxybenzene sulfonyl)-2,4-dioxothiazolidin-5-yl]pent-1-ynyl}phenyl)carbamic Acid tert-Butyl Ester | yellow oil | 578.1 |

-continued

| Ex. No. | Product | melting point °C. | mass spectrum m/z (M − H) |
|---|---|---|---|
| 147 | N-tert-Butyl-3-{5-[5-(4-iodo-benzenesulfonyl)-2,4-dioxothiazol-idin-5-yl]-pent-1-ynyl}-4-methylbenzamide | white powder | 637.5 |
| 148 | (3-{5-[5-(4-Iodobenzenesulfonyl)-2,4-dioxothiazolidin-5-yl]-pent-1-ynyl}-4-methylphenyl)carbamic Acid tert-Butyl Ester | 172–175 | 653.5 |
| 149 | (4-{5-[5-(4-Methoxybenzenesulfonyl)-2,4-dioxo-thiazolidin-5-yl]pent-1-ynyl}-3-methylphenyl)carbamic Acid tert-Butyl Ester | yellow solid | 557.7 |
| 150 | (3-{5-[5-(4-Methoxybenzenesulfonyl)-2,4-dioxothiazolidin-5-yl]pent-1-ynyl}-4-methylphenyl)carbamic Acid tert-Butyl Ester | 116–118 | 557.7 |
| 151 | (4-{5-[5-(4-Methoxybenzenesulfonyl)-2,4-dioxothiazolidin-5-yl]pent-1-ynyl}-3-trifluoromethylphenyl)-carbamic Acid tert-Butyl Ester | tan solid | 611.6 |
| 152 | N-tert-Butyl-3-{5-[5-(4-methoxy-benzenesulfonyl)-2,4-dioxothiazol-idin-5-yl]pent-1-ynyl}-4-methyl-benzamide | 205–208 | 541.7 |
| 153 | 5-(4-Methoxybenzenesulfonyl)-5-[5-(4-trifluoromethylphenyl)pent-4-ynyl]-thiazolidine-2,4-dione | 160–163 | 496.5 |
| 154 | 5-(4-Methoxybenzenesulfonyl)-5-[5-(4-trifluoromethoxyphenyl)pent-4-ynyl]-thiazolidine-2,4-dione | 120–123 | 512.5 |
| 155 | 3-{5-[5-(4-Methoxybenzenesulfonyl)-2,4-dioxo-thiazolidin-5-yl]-pent-1-ynyl}-4-methylbenzoic Acid Methyl Ester | 119–121 | 500.6 |
| 156 | 5-[5-(4-tert-Butylphenyl)pent-4-ynyl]-5-(4-methoxybenzenesulfonyl)-thiazolidine-2,4-dione | yellow oil | 484.6 |
| 157 | 5-[5-(4-tert-Butylphenyl)pent-4-ynyl]-5-(toluene-4-sulfonyl)-thiazolidine-2,4-dione | 134–138 | 468.6 |
| 158 | 4-{5-[5-(4-Methoxybenzenesulfonyl)-2,4-dioxo-thiazolidin-5-yl]pent-1-ynyl}benzonitrile | 174–178 | 453.5 |
| 159 | 5-[5-(4-Methanesulfonylphenyl)-pent-4-ynyl]-5-(toluene-4-sulfonyl)-thiazolidine-2,4-dione | 190–193 | 490.6 |
| 160 | 4-{5-[5-(4-Methoxybenzenesulfonyl)-2,4-dioxothiazolidin-5-yl]pent-1-ynyl}-3-methylbenzoic Acid Methyl Ester | 128–130 | 500.6 |
| 161 | 5-(4-Methoxybenzenesulfonyl)-5-[5-(4-pyrrol-1-yl-phenyl)pent-4-ynyl]-thiazolidine-2,4-dione | 206–207 | 493.6 |
| 162 | 5-(4-Iodo-benzenesulfonyl)-5-[5-(4-pyrrol-1-yl-phenyl)pent-4-ynyl]-thiazolidine-2,4-dione | 194–195 | 589.5 |
| 163 | 5-[5-(4-Pyrrol-1-ylphenyl)pent-4-ynyl]-5-(4-trifluoromethoxybenzenesulfonyl)-thiazolidine-2,4-dione | 204–206 | 547.6 |
| 164 | 5-(3-Methoxybenzenesulfonyl)-5-(5-thiophen-2-yl-pent-4-ynyl)-thiazolidine-2,4-dione | 133–135 | 434.5 |
| 165 | 5-(4-Methylphenylsulfonyl)-5-(5-thiophen-2-yl-pent-4-ynyl)-thiazolidine-2,4-dione | brown gum | 390.5 |
| 166 | 5-(4-Methoxybenzenesulfonyl)-5-(5-thiophen-2-yl-pent-4-ynyl)-thiazolidine-2,4-dione | 60–66 | 434.5 |
| 167 | 5-(4-Methoxybenzenesulfonyl)-5-(3-pyridin-3-ylprop-2-ynyl)-thiazolidine-2,4-dione | tan solid | 403.0 |
| 168 | 5-(3-Thiophen-2-yl-prop-2-ynyl)-5-(toluene-4-sulfonyl)-thiazolidine-2,4-dione | brown solid | 392.1 |
| 169 | 5-(3-Biphenyl-4-yl-prop-2-ynyl)-5-(toluene-4-sulfonyl)-thiazolidine-2,4-dione | 179–180 | 462 |
| 170 | 5-[3-(4-Phenoxyphenyl)prop-2-ynyl]-5-(toluene-4-sulfonyl)-thiazolidine-2,4-dione | 64–66 | 478.1 |
| 171 | 5-(3-Biphenyl-4-yl-prop-2-ynyl)-5-(4-methoxybenzenesulfonyl)-thiazolidine-2,4-dione | orange oil | |

EXAMPLE 172

5-Pent-4-ynyl-5-(toluene-4-sulfonyl)-thiazolidine-2,4-dione

In the manner of Example 100 above, 5-iodo-1-pentyne is created with 5-(toluene-4-sulfonyl)-thiazolidine-2,4-dione to give the title compound, mp 226° C., THEORY: C,53.4, H, 4.48, N, 4.15 FOUND: C, 53.3, H, 4.58, N, 4.13.

EXAMPLE 173

5-Pyridin-3-yl-pent-4-ynyl)-5-(toluene-4-sulfonyl)-thiazolidine-2,4-dione

A solution of 5-pent-4-ynyl)-5-(toluene-4-sulfonyl)-thiazolidine-2,4-dione(1.0 mmol), 4-pentyn-1-ol (1.0 mmol), bistriphenylphosphine(Pd II) chloride (0.20 mmol), and copper(I) iodide (0.10 mmol), in 50 ml of diethylamine was stirred under nitrogen for three days. This was diluted with dichloromethane and the product was purified by chromatography to give the title compound as a light beige solid, mp 173–176° C., THEORY: C, 57.95, H, 4.38 N, 6.76. FOUND: C, 57.68, H, 4.35, N, 6.70.

EXAMPLE 174

5-[5-(5-Amino-2-methylphenyl)pent-4-ynyl]-5-(4-methoxybenzenesulfonyl)-thiazolidine-2,4-dione (3-{5-[5-(4-Methoxybenzenesulfonyl)-2,4-dioxo-thiazolidin-5-yl]pent-1-ynyl}-4-methylphenyl)carbamic acid, tert-butyl ester was subjected to acid hydrolysis which gave the title compound as a brown solid, MS m/Z 458.9 (calcd. For $C_{22}H_{22}N_2O_5S_2$ 458.56).

EXAMPLE 175 to 194

The following general procedure was used to prepare the compounds of Examples 175 to 194. A solution of 1.15 g (2.5 mmol)of compound of Example 174, above, in a total of 50 mL of dichloromethane was divided equally in ten-20 mL scintillation vials. To each vessel was added 0.13 mL (3 eq), of diisopropylethylamine, the appropriate acylating agent (1.2 eq, 0.3 mmol) and the mixture was allowed to react in an orbital shaker overnight. Crude reaction mixtures were checked by Mass Spec for product. Once product formation was confirmed, the solutions were evaporated to dryness under reduced pressure, taken up in 1 mL of dichloromethane and purified via preparative HPLC. Each product fraction was then evaporated to dryness in the vacuum apparatus, characterized via mas spectrometry.

| Ex. No. | Product | Mass Spectrum (M − H) |
|---|---|---|
| 175 | (3-{5-[5-(4-Methoxybenzenesulfonyl)-2,4-dioxothiazolidin-5-yl]pent-1-ynyl}-4-methylphenyl)carbamic Acid Benzyl Ester | 591.1 |
| 176 | (3-{5-[5-(4-Methoxybenzenesulfonyl)-2,4-dioxothiazolidin-5-yl]pent-1-ynyl}-4-methylphenyl)carbamic Acid 4-Nitro-Benzyl Ester | 636.1 |
| 177 | (3-{5-[5-(4-Methoxybenzenesulfonyl)-2,4-dioxothiazolidin-5-yl]pent-1-ynyl}-4-methylphenyl)carbamic Acid 4-Chloro-phenyl Ester | 611.0 |
| 178 | (3-{5-[5-(4-Methoxybenzenesulfonyl)-2,4-dioxothiazolidin-5-yl]pent-1-ynyl}-4-methylphenyl)carbamic Acid Methyl Ester | 515.0 |
| 179 | (3-{5-[5-(4-Methoxybenzenesulfonyl)-2,4-dioxothiazolidin-5-yl]pent-1-ynyl}-4-methylphenyl)carbamic Acid Isopropyl Ester | 543.1 |
| 180 | (3-{5-[5-(4-Methoxybenzenesulfonyl)-2,4-dioxothiazolidin-5-yl]pent-1-ynyl}-4-methylphenyl)carbamic Acid Neopentyl Ester | 571.1 |
| 181 | (3-{5-[5-(4-Methoxybenzenesulfonyl)-2,4-dioxothiazolidin-5-yl]pent-1-ynyl}-4-methylphenyl)carbamic Acid Butyl Ester | 557.1 |
| 182 | (3-{5-[5-(4-Methoxybenzenesulfonyl)-2,4-dioxothiazolidin-5-yl]pent-1-ynyl}-4-methylphenyl)carbamic Acid Isobutyl | 557.1 |
| 183 | N-[3-(5-{5-[(4-Methoxyphenyl)sulfonyl]-2,4-dioxo-1,3-thiazolidin-5-yl}-1-pentynyl)-4-methylphenyl]-2-methylpropanamide | 526.9 |
| 184 | N-[3-(5-{5-[(4-Methoxyphenyl)sulfonyl]-2,4-dioxo-1,3-thiazolidin-5-yl}-1-pentynyl)-4-methylphenyl]-3,3-dimethylbutanamide | 555.0 |
| 185 | N-[3-(5-{5-[(4-Methoxyphenyl)sulfonyl]-2,4-dioxo-1,3-thiazolidin-5-yl}-1-pentynyl)-4-methylphenyl]-2,2-dimethylpropanamide | 541.0 |
| 186 | N-[3-(5-{5-[(4-Methoxyphenyl)sulfonyl]-2,4-dioxo-1,3-thiazolidin-5-yl}-1-pentynyl)-4-methylphenyl]-2-phenylacetamide | 574.9 |
| 187 | N-Benzyl-N'-[3-(5-{5-[(4-methoxyphenyl)-sulfonyl]-2,4-dioxo-1,3-thiazolidin-5-yl}-1-pentynyl)-4-methylphenyl]urea | 589.9 |
| 188 | N-(4-Methoxyphenyl)-N'-[3-(5-{5-[(4-methoxyphenyl)sulfonyl]-2,4-dioxo-1,3-thiazolidin-5-yl}-1-pentynyl)-4-methylphenyl]urea | 606.0 |
| 189 | N-(4-Chlorophenyl)-N'-[3-(5-{5-[(4-methoxy-phenyl)sulfonyl]-2,4-dioxo-1,3-thiazolidin-5-yl}-1-pentynyl)-4-methylphenyl]urea | 609.9 |
| 190 | N-[3-(5-{5-[(4-Methoxyphenyl)sulfonyl]-2,4-dioxo-1,3-thiazolidin-5-yl}-1-pentynyl)-methylphenyl]-N'-(4-methylphenyl)urea | 590.0 |

-continued

| Ex. No. | Product | Mass Spectrum (M − H) |
|---|---|---|
| 191 | 4-Chloro-N-[3-(5-{5-[(4-methoxyphenyl)-sulfonyl]-2,4-dioxo-1,3-thiazolidin-5-yl}-1-pentynyl)-4-methylphenyl]benzamide | 596.0 |
| 192 | 4-Methoxy-N-[3-(5-{5-[(4-methoxyphenyl)-sulfonyl]-2,4-dioxo-1,3-thiazolidin-5-yl}-1-pentynyl)-4-methylphenyl]benzamide | 590.9 |
| 193 | N-[3-(5-{5-[(4-Methoxyphenyl)sulfonyl]-2,4-dioxo-1,3-thiazolidin-5-yl}-1-pentynyl)-4-methylphenyl][1,1'-biphenyl]-4-carboxamide | 636.9 |
| 194 | 4-(tert-Butyl)-N-[3-(5-{5-[(4-methoxyphenyl)-sulfonyl]-2,4-dioxo-1,3-thiazolidin-5-yl}-1-pentynyl)-4-methylphenyl]benzamide | 617.0 |

EXAMPLES 195 TO 213

The following general procedure was used to prepare the compounds of Examples 195 to 213. A solution of 800 mg of each sulfone in 20 mL anhydrous DMF was distributed evenly among 4 vials (0.57–0.75 mmol each). To each was added 2.1 eq 1.0M NaHMDS under a stream of N2 and reacted in an orbital shaker for 45 min. 1.05 equivalents of the appropriate alkylating agent was dissolved in 2 mL DMF and added under N2 to the above vials. The reactions were allowed to shake overnight at room temp.

Each vial was diluted with 5 ml $H_2O$, acidified with 2NHCl, then extracted with ethyl acetate. Crude extracts were evaporated to dryness under reduced pressure in a vacuum apparatus, dissolved in 1 mL of dichloromethane, then purified via preparative HPLC. The product fractions were collected, and evaporated to dryness under reduced pressure and analyzed via MS and NMR.

| Ex. No. | Product | Mass Spectrum (M − H) |
|---|---|---|
| 195 | 5-[5-(4-Chlorophenyl)-4-pentynyl]-5-[(5-chloro-2-thienyl)sulfonyl]-1,3-thiazolidine-2,4-dione | 473.8 |
| 196 | 5-[5-(4-Chlorophenyl)-4-pentynyl]-5-(2-thienylsulfonyl)-1,3-thiazolidine-2,4-dione | 439.9 |
| 197 | 5-[5-(4-Chlorophenyl)-4-pentynyl]-5-[(3,4-dimethoxyphenyl)sulfonyl]-1,3-thiazolidine-2,4-dione | 494.0 |
| 198 | 5-[5-(4-Chlorophenyl)-4-pentynyl]-5-{[4-(4-pyridinyloxy)phenyl]sulfonyl}-1,3-thiazolidine-2,4-dione | 527.0 |
| 199 | 5-[5-(4-Chlorophenyl)-4-pentynyl]-5-{[5-(2-pyridinyl)-2-thienyl]sulfonyl}-1,3-thiazolidine-2,4-dione | 516.9 |
| 200 | 5-[(5-Chloro-2-thienyl)sulfonyl]-5-[5-(2,5-dichlorophenyl)-4-pentynyl]-1,3-thiazolidine-2,4-dione | 509.8 |
| 201 | 5-[5-(2,5-Dichlorophenyl)-4-pentynyl]-5-(2-thienylsulfonyl)-1,3-thiazolidine-2,4-dione | 473.8 |
| 202 | 5-[5-(2,5-Dichlorophenyl)-4-pentynyl]-5-[(3,4-dimethoxyphenyl)sulfonyl]-1,3-thiazolidine-2,4-dione | 527.9 |
| 203 | 5-[5-(2,5-Dichlorophenyl)-4-pentynyl]-5-{[4-(4-pyridinyloxy)phenyl]sulfonyl}-1,3-thiazolidine-2,4-dione | 560.9 |
| 204 | 5-[5-(2,5-Dichlorophenyl)-4-pentynyl]-5-{[5-(2-pyridinyl)-2-thienyl]sulfonyl}-1,3-thiazolidine-2,4-dione | 550.9 |
| 205 | tert-Butyl 3-(5-{5-[(5-chloro-2-thienyl)-sulfonyl]-2,4-dioxo-1,3-thiazolidin-5-yl}-1-pentynyl)-4-methylphenylcarbamate | 569.0 |
| 206 | tert-Butyl 3-{5-[2,4-dioxo-5-(2-thienyl-sulfonyl)-1,3-thiazolidin-5-yl]-1-pentyn-yl}-4-methylphenylcarbamate | 533.0 |
| 207 | tert-Butyl 3-(5-{5-[(3,4-dimethoxy-phenyl)sulfonyl]-2,4-dioxo-1,3-thiazol-idin-5-yl}-1-pentynyl)-4-methylphenylcarbamate | 587.1 |
| 208 | tert-Butyl 3-[5-(2,4-dioxo-5-{[4-(4-pyridinyloxy)phenyl]sulfonyl}-1,3-thiazol-idin-5-yl)-1-pentynyl]-4-methylphenylcarbamate | 620.1 |
| 209 | tert-Butyl 3-[5-(2,4-dioxo-5-{[5-(2-pyrid-inyl)-2-thienyl]sulfonyl}-1,3-thiazol-idin-5-yl)-1-pentynyl]-4-methylphenylcarbamate | 610.0 |
| 210 | N-(tert-Butyl)-3-(5-{5-[(5-chloro-2-thienyl)sulfonyl]-2,4-dioxo-1,3-thiazolidin-5-yl}-1-pentynyl)-4-methylbenzamide | 553.0 |
| 211 | N-(tert-Butyl)-3-{5-[2,4-dioxo-5-(2-thienylsulfonyl)-1,3-thiazolidin-5-yl]-1-pentynyl}-4-methylbenzamide | 517.1 |
| 212 | N-(tert-Butyl)-3-(5-{5-[(3,4-dimethoxyphenyl)sulfonyl]-2,4-dioxo-1,3-thiazolidin-5-yl}-1-pentynyl)-4-methylbenzamide | 571.1 |
| 213 | N-(tert-Butyl)-3-[5-(2,4-dioxo-5-{[5-(2-pyridinyl)-2-thienyl]sulfonyl}-1,3-thiazolidin-5-yl)-1-pentynyl]-4-methylbenzamide | 594.0 |

EXAMPLE 214

4-{5-[5-(4-Methoxybenzenesulfonyl)-2,4-dioxothiazolidin-5-yl]pent-1-ynyl}-3-methylbenzoic Acid To a solution of 4-{5-[5-(4-methoxybenzenesulfonyl)-2,4-dioxo-thiazolidin-5-yl]pent-1-ynyl}-3-methylbenzoic acid methyl ester (Example 160)(0.29 g, 0.536 mmol) in THF (30 ml plus sufficient methanol to dissolve the substrate) was added lithium hydroxide (0.75 ml of 1.0M in water), and this solution was stirred at room temperature for 3 days. Dilution with water and acidification gave a solid which was crystallized from hexane-ethyl acetate to give the title compound as a light yellow solid mp 182–184° C. THEORY: C, 56.66, H, 4.34, N, 2.87. FOUND: C, 56.39, H, 4.60, N, 2.80.

EXAMPLE 215

N-(4-Chlorobenzyl)-3-[5-(4-methoxybenzenesulfonyl)-2,4-dioxo-thiazolidin-4-yl]propionamide To a solution of 5-(4-methoxybenzenesulfonyl)-thiazolidine-2,4-dione [U.S. Pat. No. 5,605,918; February 1997; Wrobel, et al.](5.0 g, 17.4 mmol) in 150 ml of DMF was added sodium bistrimethylsilylamide (36.6 ml of 1.0 M solution in THF) and this solution was stirred for 15 minutes. To this was added methyl 3-iodopropionate (17.4 mmol) and this solution was stirred for three hours and then was subjected to an aqueous workup. The product was chromatographed (silica gel, hexane-ethyl acetate-dichloromethane, 1:1:1) to give methyl 3-[5-(4-methoxybenzenesulfonyl)-2,4-dioxothiazolidin-4-yl]propionate, 4.48 g. This was hydrolyzed with lithium hydroxide, THF, methanol to give 3-[5-(4-methoxybenzenesulfonyl)-2,4-dioxothiazolidin-4-yl]propionic acid which was used without further purification in the following procedure:

To a solution of the above acid (0.4 g, 1.1 mmol) in 15 ml of dichloromethane plus 2 ml of DMF was added 4-chlorobenzylamine (0.2 ml, 1.67 mmol) and 1-(3-dimethylaminopropyl)-3-ethylcarbodiimide hydrochloride (0.255 g, 1.33 mmol), and this was stirred at room temperature for 18 hours. Aqueous workup, and chromatography (silica gel, chloroform-methanol-5%) gave the title compound as a colorless solid, mp 90° C. and decomposes over wide range.

EXAMPLE 216

N-[2-(4-Chlorophenyl)ethyl]-3-[5-(4-methoxybenzenesulfonyl)-2,4-dioxo-thiazolidin-5-yl]propionamide In a like procedure to Example 215, above, 4-chlorophenethylamine gave the title compound as a white powder, mp 189° C. with decomposition.

EXAMPLE 217

5-[(4Z)-5-(4-Chloro-phenyl)pent-4-enyl]-5-(toluene-4-sulfonyl)-thiazolidine-2,4-dione A sample of 5-[5-(4-chlorophenyl)pent-4-ynyl]-5-(p-tolylsulfonyl)-thiazolidine-2,4-dione (Example 103) was hydrogenated in the presence of Lindlars catalyst in ethanol to give the title compound as a white solid, NMR (CDCl$_3$) δ 2.47 (s, 3H), 5.57 (apparent d of triplets, J=7.3, 11.6 Hz, 1H), 6.42 (br d, J=11.6 Hz, 1H) MS m/Z 499.0495 (M$^+$ calcd. for C$_{21}$H$_{20}$ClNO$_4$S$_2$ 499.0523).

EXAMPLE 218

5-[(4E)-5-(4-Chlorophenyl)pent-4-enyl]-5-(4-methoxybenzenesulfonyl)-thiazolidine-2,4-dione A mixture of 4-pentyn-1-ol, 1.05 eq tri-n-butyltinhydride and a catalytic amount of 1,1'-azobis(cyclohexanecarbonitrile), was heated to 55° C. overnight. The mixture was cooled, then purified on silica gel using 6:1 hex: EtOAc to 4:1 as eluent to give 86% yield of tri-n-butyl (4-pentenol)-5-ylstannane as a clear liquid which contained both cis and trans isomers. Then, 4-chloroiodobenzene (1.0 equiv.) was dissolved in anhydrous DMF under a nitrogen atmosphere. Tri-n-butyl(4-pentenol)-5-ylstannane(1.0 equiv.) was added, followed by tetrakis-triphenylphosphinePd(0)(0.1 equiv.) and CuI (0.75 equiv.). The reaction was stirred at room temperature overnight. The reaction was diluted with ether, filtered through a small pad of celite and an excess of saturated aqueous NH$_4$Cl was added, and this was stirred for 1 h. Combined organics were washed with brine, and dried over MgSO$_4$ to afford a tan semi-solid. This was purified using silica and 4:1 Hex: MeOtBu to 1:1. Obtained three cuts: 20% pure 'Z' isomer, 26% mix, 19.6% 'E' isomer (desired trans isomer) which was a light tan low melting solid.

A solution of imidazole (1.3 equiv.) and triphenylphosphine (1.3 equiv.) in acetonitrile-ether was cooled to 0° C. Iodine (1.4 equiv.) was added in three portions, and the solution was then allowed to warm to room temp overnight. The mixture was dissolved in methylene chloride, and directly preadsorbed onto silica gel and purified using 25:1 Hexanes: EtOAc as eluent to give the iodo-compound as a clear liquid. In an oven-dried round bottom flask under nitrogen was dissolved the sulfone in anhydrous DMF. Sodium hexamethyldisilazane (1.0 M solution in THF-2.1 equiv.) was added dropwise at room temperature and allowed to react at room temp for one hour. The iodide (1.1 equiv.) was dissolved in DMF, then added in one portion to the above solution., and allowed to react overnight.

The reaction was diluted with water, acidified to approx. pH 2 using 2N HCl, extracted with ethyl acetate (3×), combined organics, washed with brine, dried over MgSO$_4$ and concentrated to afford an oil which was purified on silica gel using 1:2:1 CH$_2$Cl$_2$: hex: EtOAc to afford the title compound, 36% as an off-white solid, mp 182–184° C., E-double bond—NMR (CDCl$_3$) δ6.18 (td, 1H, J=22.5 Hz), 6.31 (d, 1H, J=22.5 Hz).

EXAMPLE 219

5-[3-(4-Chlorophenyl)propyl]-5-(4-methoxybenzenesulfonyl)-thiazolidine-2,4-dione A sample of 5-[3-(4-Chlorophenyl)prop-2-ynyl]-5-(4-methoxy-benzenesulfonyl)thiazolidine-2,4-dione (U.S. Pat. No. 5,605,918; February 1997; Wrobel, et al.) was hydrogenated in the presence of palladium on charcoal (10%) in methanol plus 2% water to give the title compound as a colorless glass, NMR (CDCl$_3$) δ1.57 (m, 1H); 1.97(m, 1H); 2.20 (triplet of doublet), 1H); 2.45 (m, 1H); 2.61 (q, 2H); 3.92 (s, 3H); 7.0 (dd, 4H); 7.26 (d, 2H) 7.98 (d, 2H).

EXAMPLE 220

5-[5-(3-Aminophenyl)pent-4-ynyl]-5-(4-methoxybenzenesulfonyl)-thiazolidine-2,4-dione A sample of 5-(4-methoxybenzenesulfonyl)-5-[5-(3-nitrophenyl)pent-4-ynyl]-thiazolidine-2,4-dione of Example 118 was reduced with iron in acetic acid to give the title compound as crystals, m.p. 135–138° C.

EXAMPLE 221

5-(3-Phenylallyl)-5-(toluene-4-sulfonyl)-thiazolidine-2,4-dione

Alkylation with cinnamyl bromide (222 mg, 1.13 mmol) of 5-(4-methylphenylsulfonyl)-thiazolidine-2,4-dione (271 mg, 1.00 mmol) following the procedure in example 3 yield 32 mg (8%) of light yellow oil which was identified as 5-(3-Phenylallyl)-5-(toluene-4-sulfonyl)-thiazolidine-2,4-dione: NMR (CDCl$_3$) δ 2.49 (s, 3H), 3.06–3.13 (m, 1H), 3.34–3.42 (m, 1H), 6.01–6.11 (m, 1H), 6.60 (d, J=15.69, 1H), 7.26–7.31 (m, 5H), 7.42 (d, J=8.13, 2H), 7.85 (d, J=8.34, 2H) MS m/z 388.1 (M+H cald. for C$_{19}$H$_{17}$NO$_4$S$_2$ 387.48)

EXAMPLE 222

Enantiomer of(3-{5-[5-(4-Methoxybenzene sulfonyl)-2,4-dioxothiazolidin-5-yl]pent-1-ynyl}-4-methylphenyl)carbamic Acid tert-Butyl Ester (less polar)

The compound of Example 150 was chromatographed on a chiral column with hexane-ethanol 4:1 to give a less polar enantiomer, retention time 14.5–16 min.

EXAMPLE 223

Enantiomer of(3-{5-[5-(4-Methoxybenzene sulfonyl)-2,4-dioxothiazolidin-5-yl]pent-1-ynyl}-4-methylphenyl)carbamic Acid tert-Butyl Ester (more polar)

Continued chromatography of the compounds in Example 223 gave a more polar enantiomer, retention time 19–21 min.

EXAMPLE 224

5-(4-methoxyphenyl-4-sulfinyl)-thiazolidine-2,4-dione 5-(4-methoxyphenyl-4-sulfanyl)-thiazolidine-2,4-dione [U.S. Pat. No. 5,605,918; February 1997; Wrobel, et al.] was oxidized as described for Example 98 to give the title compound: NMR (CDCl$_3$) δ3.80 (S, 3H), 5.77 (S, 1H), 7.04 (d, 2H), 7.62 (d, 2H).

EXAMPLE 225

5-[5-(4-Chlorophenyl)pent-4-ynyl]-5-(4-methoxyphenylsulfinyl)-thiazolidine-2,4-dione By the method of Example 92, the compound of Example 224, above, is converted to the title compound.

EXAMPLES 226–233

In the isolation of products of Examples 175 to 194 the N-3-acylated products of Examples 227 to 234 were isolated and the structures were verified by mass spectrometry and NMR:

| Ex. No. | Compound |
| --- | --- |
| 226 | Benzyl 5-[5-(5-{[(benzyloxy)carbonyl]-amino}-2-methylphenyl)pent-4-ynyl]-5-[(4-methoxyphenyl)sulfonyl]-2,4-dioxo-1,3-thiazolidine-3-carboxylate |
| 227 | 4-Nitrobenzyl 5-[(4-methoxyphenyl)sulfonyl]-5-{5-[2-methyl-5-({[(4-nitro benzyl)oxy]carbonyl}amino)phenyl]pent-4-ynyl}-2,4-dioxo-1,3-thiazolidine-3-carboxylate |
| 228 | Methyl 5-(5-{5-[(methoxycarbonyl)amino]-2-methylphenyl}pent-4-ynyl)-5-[(4-methoxyphenyl)sulfonyl]-2,4-dioxo-1,3-thiazolidine-3-carboxylate |
| 229 | Isopropyl 5-(5-{5-[(isopropoxycarbonyl)-amino]-2-methylphenyl}pent-4-ynyl)-5-[(4-methoxyphenyl)sulfonyl]-2,4-dioxo-1,3-thiazolidine-3-carboxylate |
| 230 | Neopentyl 5-[(4-methoxyphenyl)sulfonyl]-5-[5-(2-methyl-5-{[(neopentyloxy)carbonyl]-amino}phenyl)pent-4-ynyl]-2,4-dioxo-1,3-thiazolidine-3-carboxylate |
| 231 | Butyl 5-(5-{5-[(butoxycarbonyl)amino]-2-methylphenyl}pent-4-ynyl)-5-[(4-methoxyphenyl)sulfonyl]-2,4-dioxo-1,3-thiazolidine-3-carboxylate |
| 232 | Isobutyl 5-(5-{5-[(isobutoxycarbonyl)-amino]-2-methylphenyl}pent-4-ynyl)-5-[(4-methoxyphenyl)sulfonyl]-2,4-dioxo-1,3-thiazolidine-3-carboxylate |

EXAMPLE 233

5-[5-(4-Chlorophenyl)pent-4-ynyl]-3-(3-imidazol-1-yl-propyl)-5-(4-methoxybenzenesulfonyl)-thiazolidine-2,4-dione The compound of Example 97 is reacted with 1,3-dibromopropane and potassium carbonate in DMF to give 5-[5-(4-chlorophenyl)pent-4-ynyl]-3-(3-bromopropyl)-5-(4-methoxybenzenesulfonyl)thiazolidine-2,4-dione, and this is reacted with imidazole, sodium salt in DMF, and in the presence of a catalytic amount of potassium iodide to give the title compound as a light tan solid, mp 111–113° C.

EXAMPLE 234

5-[5-(4-Chlorophenyl)pent-4-ynyl]-5-(4-methoxybenzenesulfonyl)-3-methyl-thiazolidine-2,4-dione 5-[5-(4-Chlorophenyl)pent-4-ynyl]-5-(4-methoxybenzenesulfonyl)-thiazolidine-2,4-dione (Example 100) is reated with sodium hydride in DMF, followed by methyl iodide to give the title compound as colorless crystals, mp 113–11 5° C.

EXAMPLE 235

3-(2,4-diethoxybenzyl)-5-(toluene-4-sulfonyl)-thiazolidine-2,4-dione 5-(Toluene-4-sulfonyl)-thiazolidine-2,4-dione[U.S. Pat No. 5,605,918; February 1997; Wrobel, et al.] was reacted with 2,4-diethoxybenzyl alcohol in the presence of triphenylphosphine and diethyl diazodicarboxylate to give the title compound as colorless crystals, mp 121–123° C.

EXAMPLE 236

5-[5-(4-Chlorophenyl)pent-4-ynyl]-3-(2,4-diethoxybenzyl)-5-(toluene-4-sulfonyl)-thiazolidine-2,4-dione The product of Example 237 is reacted with sodium hexamethyldisilazane in DMF, followed by the addition of 1-chloro-4-(5-iodopent-1-ynyl)-benzene to give the title compound as colorless crystals, mp 151–153° C.

EXAMPLE 237

5-[5-(4-Chlorophenyl)pent-4-ynyl]-5-(4-iodobenzenesulfonyl)-3-(4-nitrobenzyl)-thiazolidine-2,4-dione 5-[5-(4-Chlorophenyl)pent-4-ynyl]-5-(4-iodobenzenesulfonyl)-thiazolidine-2,4-dione is reacted with 4-nitrobenzyl bromide and potassium carbonate in DMF to give the title compound as a light tan solid, mp 172–175° C.

EXAMPLE 238

5-[5-(2,5-Dichlorophenyl)pent-4-ynyl]-5-(4-methoxybenzenesulfonyl)-2,4-dioxothiazolidine-3-carboxylic acid 2-methoxy ethyl ester 5-[5-(2,5-Dichlorophenyl)pent-4-ynyl]-5-(4-methoxybenzenesulfonyl)-thiazolidine-2,4-dione is reacted with (2-methoxyethoxy)chloroformate and diisopropylethylamine in methylene chloride to give the title compound as a solid, MS m/z 599.8 (calcd. for $C_{25}H_{23}Cl_2NO_8S_2$ 600.5).

What is claimed is:

1. A compound of Formula (I) represented by the structure:

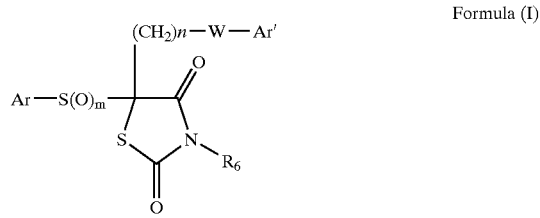

Formula (I)

wherein:
Ar is 1-naphthyl, 2-naphthyl, 8-quinolinyl, 2-thienyl, 5-chloro-2-thienyl, 5-(2-pyridyl)-2-thienyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-benzo-[b]-thienyl or a moiety of the formula:

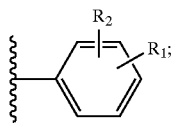

R₁ is hydrogen, fluoro, bromo, chloro, iodo, alkyl of 1 to 6 carbon atoms, alkoxy of 1 to 6 carbon atoms, 4-pyridyloxy, azido, nitro, acetamido, trifluoromethoxy, phenoxy, or benzyloxy;

R₂ is hydrogen, fluoro, bromo, chloro, iodo, alkyl of 1 to 6 carbon atoms, alkoxy of 1 to 6 carbon atoms, trifluoromethoxy, phenoxy, or benzyloxy;

m is 0, 1 or 2;

R₆ is hydrogen, alkyl of 1 to 6 carbon atoms, benzyl, substituted benzyl, imidazolylpropyl, or —CO₂Y;

Y is 2-methoxyethyl, alkyl is 1 to 6 carbon atoms, benzyl, or substituted benzyl;

W is

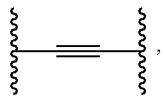

E— and Z——CH=CH—, —CONH—, —CONHCH₂—, CONHCH₂CH₂— or —CH₂—CH₂—;

n is an integer of 1 to 9;

Ar' is thienyl, pyridinyl or a moiety of the formula:

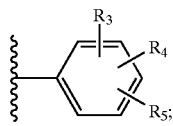

R₃, R₄, R₅, are independently selected from hydrogen, alkoxy of 1 to 6 carbon atoms, alkyl of 1 to 6 carbon atoms, fluoro, bromo, chloro, iodo, nitro, amino, hydroxy, azido, cyano, phenyl, phenoxy, trifluoromethyl, trifluoromethoxy, methanesulphonyl, 1-pyrrolyl, —CO₂R₇, —CONHR₈, —CH₂CONHR₉, —NHCO₂R₁₀, —NHCOR₁₁, and —NHCONHR₁₂;

R₇ is selected from H, and alkyl of 1 to 6 carbon atoms,

R₈ is selected from H, and alkyl of 1 to 6 carbon atoms;

R₉ is selected from H, and alkyl of 1 to 6 carbon atoms;

R₁₀ is selected from alkyl of 1 to 6 carbon atoms, benzyl, nitrobenzyl, and chlorophenyl;

R₁₁ is selected from alkyl of 1 to 6 carbon atoms, benzyl, phenyl, halophenyl, alkyl(1 to 6 carbon atoms)phenyl, alkoxy(1 to 6 carbon atoms)phenyl, and biphenyl;

R₁₂ is benzyl, alkyl of 1 to 6 carbon atoms, alkoxy(1 to 6 carbon atoms)phenyl, halophenyl, and alkyl(1 to 6 carbon atoms)phenyl;

provided when W is

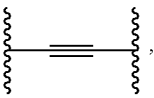

then n is other than 2;

further provided that when n is 1, m is 0 or 2, R₆ is H and W is

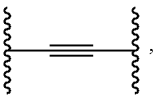

then:

Ar is not phenyl, 2-naphthyl, alkyl substituted phenyl, alkoxy substituted phenyl, halogen substituted phenyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, or 2-benzo-[b]-thienyl; and Ar' is not phenyl, alkyl substituted phenyl, perfluoroalkyl (mono or di)substituted phenyl, halogen substituted phenyl, alkoxy substituted phenyl, perfluoroalkoxy substituted phenyl or alkylthio substituted phenyl;

or pharmaceutically acceptable salts thereof.

2. A compound according to claim 1 wherein R₆ is hydrogen, n is 3, m is 2, W is

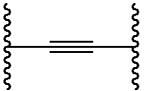

or a pharmaceutically acceptable salt thereof.

3. A compound according to claim 1 wherein R₆ is hydrogen, n is 3, m is 2, W is

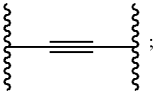

Ar is a moiety of the formula:

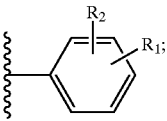

or a pharmaceutically acceptable salt thereof.

4. A compound according to claim 1 wherein R₆ is hydrogen, n is 3, m is 2, W is

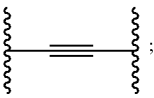

Ar is a moiety of the formula:

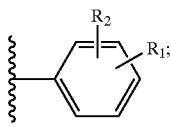

Ar' is a moiety of the formula:

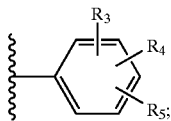

or a pharmaceutically acceptable salt thereof.

5. A compound according to claim 1 wherein $R_6$ is hydrogen, n is 3, m is 2, W is

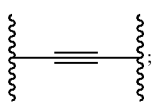

Ar is a moiety of the formula:

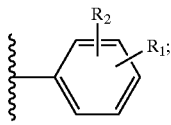

Ar' is thienyl or pyridinyl or a pharmaceutically acceptable salt thereof.

6. A compound according to claim 1 wherein $R_6$ is hydrogen, n is 3–6, m is 2, W is

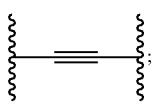

or a pharmaceutically acceptable salt thereof.

7. A compound according to claim 1 wherein $R_6$ is hydrogen, n is 3–6, m is 2, W is

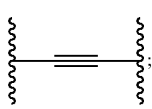

Ar is a moiety of the formula:

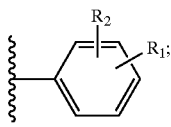

or a pharmaceutically acceptable salt thereof.

8. A compound according to claim 1 wherein $R_6$ is hydrogen, n is 3–6, m is 2, W is

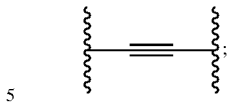

Ar is a moiety of the formula:

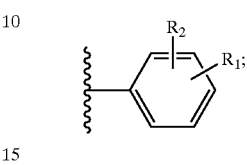

Ar' is a moiety of the formula:

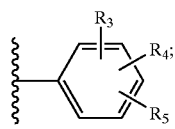

or a pharmaceutically acceptable salt thereof.

9. A compound according to claim 1 wherein $R_6$ is hydrogen, n is 3–6, m is 2, W is

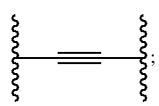

Ar is a moiety of the formula:

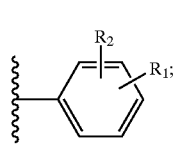

Ar' is thienyl or pyridinyl or a pharmaceutically acceptable salt thereof.

10. A compound according to claim 1 wherein $R_6$ is hydrogen, n is 1, m is 2, W is

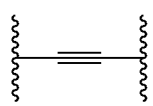

or a pharmaceutically acceptable salt thereof.

11. A compound according to claim 1 wherein $R_6$ is hydrogen, n is 1, m is 2, W is

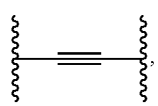

Ar is a moiety of the formula:

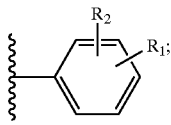

or a pharmaceutically acceptable salt thereof.

12. A compound according to claim 1 wherein $R_6$ is hydrogen, n is 1, m is 2, W is

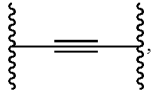

Ar is a moiety of the formula:

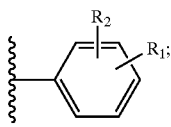

Ar' is a moiety of the formula:

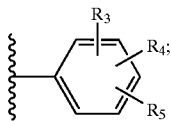

or a pharmaceutically acceptable salt thereof.

13. A compound according to claim 1 wherein $R_6$ is hydrogen, n is 1, m is 2, W is

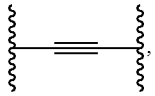

Ar is a moiety of the formula:

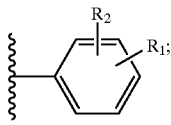

Ar' is thienyl or pyridinyl or a pharmaceutically acceptable salt thereof.

14. A compound according to claim 1 wherein m is 2, Ar is phenyl substituted in the 4-position by iodo, methoxy, trifluoromethoxy, 4-pyridyloxy; Ar' is phenyl substituted in the 2-position by chloro or methyl, and in the 5-position by amino, chloro, a carbamic acid ester, a substituted carboxamide group, or in the 4-position by nitro or a carbamic acid ester; W is an acetylenic group, and n is the integer 3 or a pharmaceutically acceptable salt thereof.

15. The compound of claim 1 selected from the group consisting of:

5-[5-(4-Chlorophenyl)pent-4-ynyl]-5-(4-methoxyphenylsulfanyl)-thiazolidine-2,4-dione, 5-[6-(4-Chlorophenyl)hex-5-ynyl]-5-(4-methoxyphenylsulfanyl)-thiazolidine-2,4-dione, 5-[11-(4-Chlorophenyl)undec-10-ynyl]-5-(4-methoxyphenylsulfanyl)-thiazolidine-2,4-dione, 5-(4-Methoxyphenylsulfanyl)-5-(5-thiophen-2-yl-pent-4-ynyl)-thiazolidine-2,4-dione, 5-[5-(4-Chlorophenyl)pent-4-ynyl]-5-(4-fluorophenylsulfanyl)-thiazolidine-2,4-dione, 5-[5-(4-Chlorophenyl)pent-4-ynyl]-5-(4-methoxyphenylsulfonyl)thiazolidine-2,4-dione, 5-[6-(4-Chlorophenyl)hex-5-ynyl]-5-(4-methoxyphenylsulfonyl) thiazolidine-2,4-dione, 5-[11-(4-Chlorophenyl)undec-10-ynyl]-5-(4-methoxyphenylsulfonyl)thiazolidine-2,4-dione, 5-[5-(4-Chlorophenyl)pent-4-ynyl]-5-(4-methoxyphenylsulfonyl)thiazolidine-2,4-dione, 5-[5-(2-Chlorophenyl)pent-4-ynyl]-5-(4-methoxybenzenesulfonyl)thiazolidine-2,4-dione, 5-[5-(3-Chlorophenyl)pent-4-ynyl]-5-(4-methoxybenzenesulfonyl)thiazolidine-2,4-dione, 5-[5-(4-Chlorophenyl)pent-4-ynyl]-5-(p-tolylsulfonyl) thiazolidine-2,4-dione, 5-[5-(4-Chlorophenyl)pent-4-ynyl]-5-(4-iodobenzenesulfonyl)thiazolidine-2,4-dione, 5-[5-(4-Chlorophenyl)pent-4-ynyl]-5-(4-fluorobenzenesulfonyl)thiazolidine-2,4-dione, 5-[5-(4-Chlorophenyl)pent-4-ynyl]-5-(4-phenoxybenzenesulfonyl)thiazolidine-2,4-dione, 5-[5-(4-Chlorophenyl)pent-4-ynyl]-5-(naphthalene-2-sulfonyl)thiazolidine-2,4-dione, N-(4-{5-[5-(4-Chlorophenyl)pent-4-ynyl]-2,4-dioxothiazolidine-5-sulfonyl}phenyl)acetamide, 5-[5-(4-Chlorophenyl)pent-4-ynyl]-5-(quinoline-8-sulfonyl)thiazolidine-2,4-dione, 5-[5-(4-Chlorophenyl)pent-4-ynyl]-5-(4-nitrobenzenesulfonyl)thiazolidine-2,4-dione, 5-(4-Benzyloxybenzenesulfonyl)-5-[5-(4-chlorophenyl)pent-4-ynyl]thiazolidine-2,4-dione, 5-(4-Butoxybenzenesulfonyl)-5-[5-(4-chlorophenyl)-pent-4-ynyl]thiazolidine -2,4-dione, 5-[5-(4-Chlorophenyl)pent-4-ynyl]-5-(naphthalene-1-sulfonyl)thiazolidine-2,4-dione, 5-[5-(2,5-Dichloro-phenyl)pent-4-ynyl]-5-(4-methoxy-benzenesulfonyl)thiazolidine-2,4-dione, 5-[5-(2,5-Dichloro-phenyl)pent-4-ynyl]-5-(4-iodobenzenesulfonyl)thiazolidine-2,4-dione, 5-[5-(2,5-Dichlorophenyl)pent-4-ynyl]-5-[4-(pyridin-4-yloxy)benzenesulfonyl]thiazolidine-2,4-dione, 5-[5-(2,4-Dichlorophenyl)pent-4-ynyl]-5-(4-methoxybenzenesulfonyl)thiazolidine-2,4-dione, 5-(4-Methoxybenzenesulfonyl)-5-[5-(3-nitrophenyl)pent-4-ynyl]thiazolidine-2,4-dione, 5-[5-(3-Nitrophenyl)pent-4-ynyl]-5-(4-phenoxybenzenesulfonyl)thiazolidine-2,4-dione, 5-(4-Iodobenzenesulfonyl)-5-[5-(4-nitrophenyl)pent-4-ynyl]thiazolidine-2,4-dione, 5-(4-Methoxybenzene sulfonyl)-5-[5-(4-nitrophenyl)pent-4-ynyl]thiazolidine-2,4-dione, 5-(4-Methoxybenzene sulfonyl)-5-[5-(2-methyl-5-nitrophenyl)pent-4-ynyl]thiazolidine-2,4-dione, 5-(4-Methoxybenzenesulfonyl)-5-[5-(2-methoxy-5-nitrophenyl)pent-4-ynyl]thiazolidine-2,4-dione, 5-[5-(2-Methyl-5-nitrophenyl)pent-4-ynyl]-5-(4-phenoxybenzenesulfonyl)thiazolidine-2,4-dione, 5-(4-Iodobenzenesulfonyl)-5-[5-(2-methyl-5-nitrophenyl)pent-4-ynyl]thiazolidine-2,4-dione, 5-[5-(2-Methyl-5-nitrophenyl)-pent-4-ynyl]-5-(naphthalene-1-sulfonyl)thiazolidine-2,4-dione, 5-[5-(2-Methyl-5-nitrophenyl)pent-4-ynyl]-5-(naphthalene-2-sulfonyl)thiazolidine-2,4-dione, 5-[5-(2-Methyl-4-nitrophenyl)pent-4-ynyl]-5-[4-(pyridin-4-yloxy)benzenesulfonyl]-thiazolidine-2,4-dione, 5-[5-(2-Methyl-4-nitrophenyl)pent-4-ynyl]-5-(4-phenoxybenzenesulfonyl)thiazolidine-2,4-dione, 5-(4-Methoxybenzenesulfonyl)-5-[5-(2-methyl-4-nitrophenyl)-pent-4-ynyl]thiazolidine-2,4-dione, 5-(4-Iodobenzenesulfonyl)-5-[5-(2-methyl-4-nitrophenyl)pent-4-ynyl]thiazolidine-2,4-dione, 5-(4-Methoxybenzenesulfonyl)-5-[5-(2-methoxy-4-nitrophenyl)pent-4-ynyl]thiazolidine-2,4-dione, 5-[5-(3-Fluoro-5-nitrophenyl)pent-4-ynyl]-5-(4-methoxybenzene-sulfonyl)thiazolidine-2,4-dione, 5-[5-(2,5-Dimethylphenyl)pent-4-ynyl]-5-(4-iodobenzenesulfonyl)thiazolidine-2,4-dione, 5-[5-(2,5-Dimethylphenyl)pent-4-ynyl]-5-(4-methoxybenzenesulfonyl)thiazolidine-2,4-dione, 5-[5-(2,4-Dimethylphenyl)pent-4-ynyl]-5-(4-methoxybenzenesulfonyl)thiazolidine-2,4-dione, 5-[5-(2,4-Dimethylphenyl)pent-4-ynyl]-5-(4-iodobenzenesulfonyl)thiazolidine-2,4-dione, 5-[5-(5-Chloro-2-methylphenyl)pent-4-ynyl]-5-(4-methoxybenzenesulfonyl)thiazolidine-2,4-dione, 5-[5-(5-Chloro-2-methylphenyl)pent-4-ynyl]-5-(4-trifluoromethoxybenzenesulfonyl)thiazolidine-2,4-dione, 5-[5-(4-Chloro-2-methylphenyl)pent-4-ynyl]-5-(4-trifluoromethoxybenzenesulfonyl)thiazolidine-2,4-dione, 5-[5-(4-Chloro-2-methylphenyl)-pent-4-ynyl]-5-(4-iodobenzenesulfonyl)thiazolidine-2,4-dione, 5-[5-(4-Chloro-2-methylphenyl) pent-4-ynyl]-5-(4-methoxybenzenesulfonyl)thiazolidine-2,4-dione, 5-[5-(4-Bromo-2-methy-phenyl)pent-4-ynyl]-5-(4-methoxybenzenesulfonyl)thiazolidine-2,4-dione, 5-[5-(4-Bromo-2-methylphenyl)pent-4-ynyl]-5-(4-iodobenzenesulfonyl)thiazolidine-2,4-dione, (4-{5-[5-(4-Methoxybenzensulfonyl)-2,4-dioxothiazolidin-5-yl]pent-1-ynyl}phenyl)carbamic Acid tert-Butyl Ester, (3-Chloro-4-{5-[5-(4-methoxybenzene sulfonyl)-2,4-dioxothiazolidin-5-yl]pent-1-ynyl}phenyl)carbamic Acid tert-Butyl Ester, N-tert-Butyl-3-{5-[5-(4-iodo-benzenesulfonyl)-2,4-dioxothiazolidin-5-yl]-pent-1-ynyl}-4-methylbenzamide, (3-{5-[5-(4-Iodobenzenesulfonyl)-2,4-dioxothiazolidin-5-yl]-pent-1-ynyl}-4-methylphenyl)carbamic Acid tert-Butyl Ester, (4-{5-[5-(4-Methoxybenzenesulfonyl)-2,4-dioxothiazolidin-5-yl]pent-1-ynyl}-3-methylphenyl) carbamic Acid tert-Butyl Ester, (3-{5-[5-(4-Methoxybenzenesulfonyl)-2,4-dioxothiazolidin-5-yl]pent-1-ynyl}-4-methylphenyl) carbamic Acid tert-Butyl Ester, (4-{5-[5-(4-Methoxybenzenesulfonyl)-2,4-dioxothiazolidin-5-yl]pent-1-ynyl}-3-trifluoromethylphenyl)-carbamic Acid tert-Butyl Ester, N-tert-Butyl-3-{5-[5-(4-methoxy-benzenesulfonyl)-2,4-dioxothiazolidin-5-yl]pent-1-ynyl}-4-methylbenzamide, 5-(4-Methoxybenzenesulfonyl)-5-[5-(4-trifluoromethylphenyl)pent-4-ynyl]thiazolidine-2,4-dione, 5-(4-Methoxybenzenesulfonyl)-5-[5-(4-trifluoromethoxyphenyl)pent-4-ynyl]thiazolidine-2,4-dione, 3-{5-[5-(4-Methoxybenzenesulfonyl)-2,4-dioxothiazolidin-5-yl]-pent-1-ynyl}-4-methylbenzoic Acid Methyl Ester, 5-[5-(4-tert-Butylphenyl)pent-4-ynyl]-5-(4-methoxybenzenesulfonyl)thiazolidine-2,4-dione, 5-[5-(4-tert-Butylphenyl)pent-4-ynyl]-5-(toluene-4-sulfonyl)thiazolidine-2,4-dione, 4-{5-[5-(4-Methoxybenzenesulfonyl)-2,4-dioxothiazolidin-5-yl]pent-1-ynyl}benzonitrile, 5-[5-(4-Methanesulfonylphenyl)-pent-4-ynyl]-5-(toluene-4-sulfonyl)thiazolidine-2,4-dione, 4-(5-[5-(4-Methoxybenzenesulfonyl)-2,4-dioxothiazolidin-5-yl]pent-1-ynyl)-3-methylbenzoic Acid Methyl Ester, 5-(4-Methoxybenzenesulfonyl)-5-[5-(4-pyrrol-1-ylphenyl)pent-4-ynyl]thiazolidine-2,4-dione, 5-(4-Iodo-benzenesulfonyl)-5-[5-(4-pyrrol-1-yl-phenyl)pent-4-ynyl]thiazolidine-2,4-dione, 5-[5-(4-Pyrrol-1-ylphenyl)pent-4-ynyl]-5-(4-trifluoromethoxybenzenesulfonyl)thiazolidine-2,4-dione, 5-(3-Methoxybenzenesulfonyl)-5-(5-thiophen-2-yl-pent-4-ynyl)thiazolidine-2,4-dione, 5-(4-Methylphenylsulfonyl)-5-(5-thiophen-2-yl-pent-4-ynyl)thiazolidine-2,4-dione, 5-(4-Methoxybenzenesulfonyl)-5-(5-thiophen-2-yl-pent-4-ynyl)thiazolidine-2,4-dione, 5-(4-Methoxybenzenesulfonyl)-5-(3-pyridin-3-ylprop-2-ynyl)thiazolidine-2,4-dione, 5-(3-Thiophen-2-yl-prop-2-ynyl)-5-(toluene-4-sulfonyl)thiazolidine-2,4-dione, 5-(3-Biphenyl-4-yl-prop-2-ynyl)-5-(toluene-4-sulfonyl)thiazolidine-2,4-dione, 5-[3-(4-Phenoxyphenyl)prop-2-ynyl]-5-(toluene-4-sulfonyl)thiazolidine-2,4-dione, 5-(3-Biphenyl-4-yl-prop-2-ynyl)-5-(4-methoxybenzenesulfonyl)thiazolidine-2,4-dione, 5-(5-Pyridin-3-yl-pent-4-ynyl)-5-(toluene-4-sulfonyl)thiazolidine-2,4-dione, 5-[5-(5-Amino-2-methylphenyl)pent-4-ynyl]-5-(4-methoxybenzenesulfonyl)thiazolidine-2,4-dione, (3-{5-[5-(4-Methoxybenzenesulfonyl)-2,4-dioxothiazolidin-5-yl]pent-1-ynyl}-4-methylphenyl) carbamic Acid Benzyl Ester, (3-{5-[5-(4-Methoxybenzenesulfonyl)-2,4-dioxothiazolidin-5-yl]pent-1-ynyl}-4-methylphenyl) carbamic Acid 4-Nitro-Benzyl Ester, (3-{5-[5-(4-Methoxybenzenesulfonyl)-2,4-dioxothiazolidin-5-yl]pent-1-ynyl}-4-methylphenyl) carbamic Acid 4-Chloro-phenyl Ester, (3-{5-[5-(4-Methoxybenzenesulfonyl)-2,4-dioxothiazolidin-5-yl]pent-1-ynyl}-4-methylphenyl) carbamic Acid Methyl Ester, (3-{5-[5-(4-Methoxybenzenesulfonyl)-2,4-dioxothiazolidin-5-yl]pent-1-ynyl}-4-methylphenyl) carbamic Acid Isopropyl Ester, (3-{5-[5-(4-Methoxybenzenesulfonyl)-2,4-dioxothiazolidin-5-yl]pent-1-ynyl}-4-methylphenyl) carbamic Acid Neopentyl Ester, (3-{5-[5-(4-Methoxybenzenesulfonyl)-2,4-dioxothiazolidin-5-yl]pent-1-ynyl}-4-methylphenyl) carbamic Acid Butyl Ester, (3-{5-[5-(4-Methoxybenzenesulfonyl)-2,4-dioxothiazolidin-5-yl]pent-1-ynyl}-4-methylphenyl) carbamic Acid Isobutyl, N-[3-(5-{5-[(4-Methoxyphenyl)sulfonyl]-2,4-dioxo-1,3-thiazolidin-5-yl}-1-pentynyl)-4-methylphenyl]-2-methylpropanamide, N-[3-(5-{5-[(4-Methoxyphenyl)sulfonyl]-2,4-dioxo-1,3-thiazolidin-5-yl}-1-pentynyl)-4-methylphenyl]-3,3-dimethylbutanamide, N-[3-(5-{5-[(4-Methoxyphenyl)sulfonyl]-2,4-dioxo-1,3-thiazolidin-5-yl}-1-pentynyl)-4-methylphenyl]-2,2-dimethylpropanamide, N-[3-(5-{5-[(4-Methoxyphenyl)sulfonyl]-2,4-dioxo-1,3-thiazolidin-5-yl}-1-pentynyl)-4-methylphenyl]-2-phenylacetamide, N-Benzyl-N'-[3-(5-{5-[(4-methoxyphenyl)-sulfonyl]-2,4-dioxo-1,3-thiazolidin-5-yl}-1-pentynyl)-4-methylphenyl]urea, N-(4-Methoxyphenyl)-N'-[3-(5-{5-[(4-methoxy phenyl)sulfonyl]-2,4-dioxo-1,3-thiazolidin-5-yl}-1-pentynyl)-4-methylphenyl]urea, N-(4-Chlorophenyl)-N'-[3-(5-{5-[(4-methoxy-phenyl)sulfonyl]-2,4-dioxo-1,3-thiazolidin-5-yl}-1-pentynyl)-4-methylphenyl]urea, N-[3-(5-{5-[(4-Methoxyphenyl)sulfonyl-2,4-dioxo-1,3-thiazolidin-5-yl}-1-pentynyl)-methylphenyl]-N'-(4-methylphenyl)urea, 4-Chloro-N-[3-(5-{5-[(4-methoxyphenyl)-sulfonyl]-2,4-dioxo-1,3-thiazolidin-5-yl}-1-pentynyl)-4-methylphenyl]benzamide, 4-Methoxy-N-[3-(5-{5-[(4-methoxyphenyl)-sulfonyl]-2,4-dioxo-1,3-thiazolidin-5-yl}-1-pentynyl)-4-methylphenyl]benzamide, N-[3-(5-{5-[(4-Methoxyphenyl)sulfonyl]-2,4-dioxo-1,3-thiazolidin-5-yl}-1-pentynyl)-4-methylphenyl][1,1'-biphenyl]-4-carboxamide, tert-Butyl 3-{5-[2,4-dioxo-5-(2-thienyl-sulfonyl)-1,3-thiazolidin-5-yl]-1-pentyn-yl}-4-methylphenylcarbamate, tert-Butyl 3-(5-{5-[(3,4-dimethoxy-phenyl)sulfonyl]-2,4-dioxo-1,3-thiazolidin-5-yl}-1-pentynyl)-4-methylphenylcarbamate, tert-Butyl 3-[5-(2,4-dioxo-5-{[4-(4-pyridinyloxy)phenyl]sulfonyl}-1,3-thiazolidin-5-yl)-1-pentynyl]-4-methylphenylcarbamate, tert-Butyl 3-[5-(2,4-dioxo-5-{[5-(2-pyridinyl)-2-thienyl]sulfonyl}-1,3-thiazolidin-1-pentynyl]-4-methylphenylcarbamate, N-(tert-Butyl)-3-(5-{5-[(5-chloro-2-thienyl)sulfonyl]-2,4-dioxo-1,3-thiazolidin-5-yl}-1-pentynyl)-4-methylbenzamide, N-(tert-Butyl)-3-{5-[2,4-dioxo-5-(2-thienylsulfonyl)-1,3-thiazolidin-5-yl]-1-pentynyl}-4-methylbenzamide, N-(tert-Butyl)-3-(5-{5-[(3,4-dimethoxyphenyl)sulfonyl]-2,4-dioxo-1,3-thiazolidin-5-yl}-1-pentynyl)-4-methylbenzamide, N-(tert-Butyl)-3-[5-(2,4-dioxo-5-{[5-(2-pyridinyl)-2-thienyl]sulfonyl}-1,3-thiazolidin-5-yl)-1-pentynyl]-4-methylbenzamide, 4-{5-[5-(4-Methoxybenzenesulfonyl)-2,4-dioxothiazolidin-5-yl]pent-1-ynyl}-3-methylbenzoic Acid, N-(4-Chlorobenzyl)-3-[5-(4-methoxybenzenesulfonyl)-2,4-dioxo-thiazolidin-4-yl]propionamide, N-[2-(4-Chlorophenyl)ethyl]-3-[5-(4-methoxybenzenesulfonyl)-2,4-dioxo-thiazolidin-5-yl] propionamide, 4-(tert-Butyl)-N-[3-(5-{5-[(4-methoxyphenyl)-sulfonyl]-2,4-dioxo-1,3-thiazolidin-5-yl}-1-pentynyl)-4-methylphenyl]benzamide, 5-[5-(4-Chlorophenyl)-4-pentynyl]-5-[(5-chloro-2-thienyl)sulfonyl]-1,3-thiazolidine-2,4-dione, 5-[5-(4-Chlorophenyl)-4-pentynyl]-5-(2-thienylsulfonyl)-1,3-thiazolidine-2,4-dione, 5-[5-(4-Chlorophenyl)-4-pentynyl]-5-[(3,4-dimethoxyphenyl)sulfonyl]-1,3-thiazolidine-2,4-dione, 5-[5-(4-Chlorophenyl)-4-pentynyl]-5-{[4-(4-pyridinyloxy)phenyl]sulfonyl}-1,3-thiazolidine-2,4-dione, 5-[5-(4-Chlorophenyl)-4-pentynyl]-5-{[5-(2-pyridinyl)-2-thienyl]sulfonyl}-1,3-thiazolidine-2,4-dione, 5-[(5-Chloro-2-thienyl)sulfonyl]-5-[5-(2,5-dichlorophenyl)-4-pentynyl]-1,3-thiazolidine-2,4-dione, 5-[5-(2,5-Dichlorophenyl)-4-pentynyl]-5-(2-thienylsulfonyl)-1,3-thiazolidine-2,4-dione, 5-[5-(2,5-Dichlorophenyl)-4-pentynyl]-5-[(3,4-dimethoxyphenyl)sulfonyl]-1,3-thiazolidine-2,4-dione, 5-[5-(2,5-Dichlorophenyl)-4-pentynyl]-5-{[4-(4-pyridinyloxy)phenyl]sulfonyl}-3-thiazolidine-2,4-dione, 5-[5-(2,5-Dichlorophenyl)-4-pentynyl]-5-{[5-(2-pyridinyl)-2-thienyl]sulfonyl}-1,3-thiazolidine-2,4-dione, tert-Butyl 3-(5-{5-[(5-chloro-2-thienyl)-sulfonyl]-2,4-dioxo-1,3-thiazolidin-5-yl}-1-pentynyl)-4-methylphenylcarbamate, 5-[(4Z)-5-(4-Chloro-phenyl)pent-4-enyl]-5-(toluene-4-sulfonyl)thiazolidine-2,4-dione, 5-[(4E)-5-(4-Chlorophenyl)pent-4-enyl]-5-(4-methoxybenzene sulfonyl)thiazolidine-2,4-dione, 5-[3-(4-Chlorophenyl)propyl]-5-(4-methoxybenzenesulfonyl) thiazolidine-2,4-dione, 5-[5-(3-Aminophenyl)pent-4-ynyl]-5-(4-methoxybenzenesulfonyl)thiazolidine-2,4-dione, 5-(3-Phenylallyl)-5-(toluene-4-sulfonyl)thiazolidine-2,4-dione, Enantiomer of(3-{5-[5-(4-Methoxybenzene sulfonyl)-2,4-dioxothiazolidin-5-yl]pent-1-ynyl}-4-methylphenyl) carbamic Acid tert-Butyl Ester (less polar), Enantiomer of(3-{5-[5-(4-Methoxybenzene sulfonyl)-2,4-dioxothiazolidin-5-yl]pent-1-ynyl}-4-methylphenyl) carbamic Acid tert-Butyl Ester (more polar), 5-[5-(4-Chlorophenyl)pent-4-ynyl]-5-(4-methoxyphenylsulfinyl)thiazolidine-2,4-dione, Benzyl 5-[5-(5-{[(benzyloxy)carbonyl]-amino}-2-methylphenyl)pent-4-ynyl]-5-[(4-methoxyphenyl)sulfonyl]-2,4-dioxo-1,3-thiazolidine-3-carboxylate, 4-Nitrobenzyl 5-[(4-methoxyphenyl) sulfonyl]-5-{5-[2-methyl-5-({[(4-nitro benzyl)oxy]carbonyl}amino)phenyl]pent-4-ynyl}-2,4-dioxo-1,3-thiazolidine-3-carboxylate, Methyl 5-(5-{5-[(methoxycarbonyl)amino]-2-methylphenyl}pent-4-ynyl)-5-[(4-methoxyphenyl)sulfonyl]-2,4-dioxo-1,3-thiazolidine-3-carboxylate, Isopropyl 5-(5-{5-[(isopropoxycarbonyl)-amino]-2-methylphenyl}pent-4-ynyl)-5-[(4-methoxyphenyl)sulfonyl]-2,4-dioxo-1,3-thiazolidine-3-carboxylate, Neopentyl 5-[(4-methoxyphenyl)sulfonyl]-5-[5-(2-methyl-5-{[(neopentyloxy)carbonyl]-amino}phenyl)pent-4-ynyl]-2,4-dioxo-1,3-thiazolidine-3-carboxylate, Butyl 5-(5-{5-[(butoxycarbonyl)amino]-2-methylphenyl}pent-4-ynyl)-5-[(4-methoxy-phenyl)sulfonyl]-2,4-dioxo-1,3-thiazolidine-3-carboxylate, Isobutyl 5-(5-{5-[(isobutoxycarbonyl)-amino]-2-methylphenyl}pent-4-ynyl)-5-[(4-methoxyphenyl)sulfonyl]-2,4-dioxo-1,3-thiazolidine-3-carboxylate, 5-[5-(4-Chlorophenyl)pent-4-ynyl]-3-(3-imidazol-1-yl-propyl)-5-(4-methoxybenzenesulfonyl)thiazolidine-2,4-dione, 5-[5-(4-Chlorophenyl)pent-4-ynyl]-5-(4-methoxybenzenesulfonyl)-3-methyl-thiazolidine-2,4-dione, 5-[5-(4-Chlorophenyl)pent-4-ynyl]-3-(2,4-diethoxybenzyl)-5-(toluene-4-sulfonyl)thiazolidine-2,4-dione, 5-[5-(4-Chlorophenyl)pent-4-ynyl]-5-(4-iodobenzenesulfonyl)-3-(4-nitrobenzyl)thiazolidine-2,4-dione, and 5-[5-(2,5-Dichlorophenyl)pent-4-ynyl]-5-(4-methoxybenzenesulfonyl)-2,4-dioxothiazolidine-3-carboxylic acid 2-methoxy ethyl ester.

16. A pharmaceutical composition comprising an effective amount of a compound of claim 1 in combination with one or more pharmaceutically acceptable carriers.

17. A pharmaceutical composition according to claim 16 wherein $R_6$ is hydrogen, n is 3, m is 2, W is

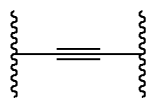

or a pharmaceutically acceptable salt thereof.

18. A pharmaceutical composition according to claim 16 wherein $R_6$ is hydrogen, n is 3, m is 2, W is

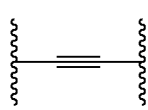

Ar is a moiety of the formula:

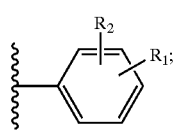

or a pharmaceutically acceptable salt thereof.

19. A pharmaceutical composition according to claim 16 wherein $R_6$ is hydrogen, n is 3, m is 2, W is

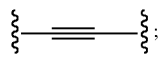

Ar is a moiety of the formula:

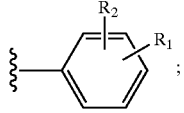

Ar' is a moiety of the formula:

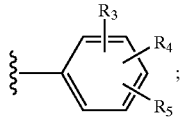

or a pharmaceutically acceptable salt thereof.

20. A pharmaceutical composition according to claim 16 wherein $R_6$ is hydrogen, n is 3, m is 2, W is

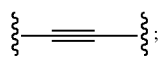

Ar is a moiety of the formula:

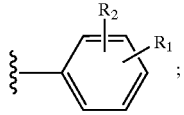

Ar' is thienyl or pyridinyl or a pharmaceutically acceptable salt thereof.

21. A pharmaceutical composition according to claim 16 wherein $R_6$ is hydrogen, n is 3–6, m is 2, W is

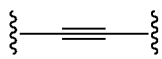

or a pharmaceutically acceptable salt thereof.

22. A pharmaceutical composition according to claim 16 wherein $R_6$ is hydrogen, n is 3–6, m is 2, W is

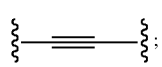

Ar is a moiety of the formula:

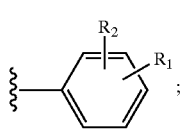

or a pharmaceutically acceptable salt thereof.

23. A pharmaceutical composition according to claim 16 wherein $R_6$ is hydrogen, n is 3–6, m is 2, W is

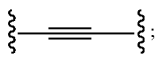

Ar is a moiety of the formula:

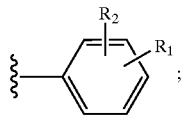

Ar' is a moiety of the formula:

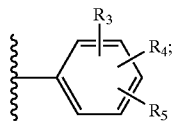

or a pharmaceutically acceptable salt thereof.

24. A pharmaceutical composition according to claim 16 wherein $R_6$ is hydrogen, n is 3–6, m is 2, W is

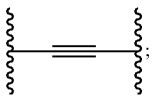

Ar is a moiety of the formula:

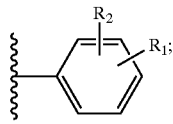

Ar' is thienyl or pyridinyl or a pharmaceutically acceptable salt thereof.

25. A pharmaceutical composition according to claim 16 wherein $R_6$ is hydrogen, n is 1, m is 2, W is

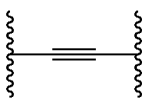

or a pharmaceutically acceptable salt thereof.

26. A pharmaceutical composition according to claim 16 wherein $R_6$ is hydrogen, n is 1, m is 2, W is

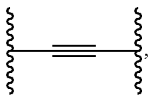

Ar is a moiety of the formula:

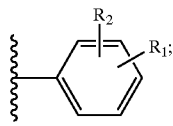

or a pharmaceutically acceptable salt thereof.

27. A pharmaceutical composition according to claim 16 wherein $R_6$ is hydrogen, n is 1, m is 2, W is

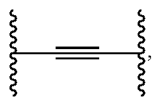

Ar is a moiety of the formula:

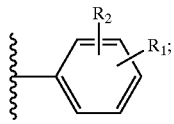

Ar' is a moiety of the formula:

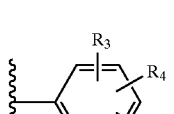

or a pharmaceutically acceptable salt thereof.

28. A pharmaceutical composition according to claim 16 wherein $R_6$ is hydrogen, n is 1, m is 2, W is

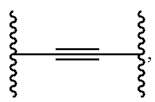

Ar is a moiety of the formula:

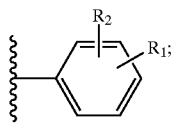

Ar' is thienyl or pyridinyl or a pharmaceutically acceptable salt thereof.

29. A pharmaceutical composition according to claim 16 wherein m is 2, Ar is phenyl substituted in the 4-position by iodo, methoxy, trifluoromethoxy, 4-pyridyloxy; Ar' is phenyl substituted in the 2-position by chloro or methyl, and in the 5-position by amino, chloro, a carbamic acid ester, a substituted carboxamide group, or in the 4-position by nitro or a carbamic acid ester; W is an acetylenic group, and n is the integer 3 or a pharmaceutically acceptable salt thereof.

30. A pharmaceutical composition according to claim 16 wherein the compound is selected from the group consisting of:

5-[5-(4-Chlorophenyl)pent-4-ynyl]-5-(4-methoxyphenylsulfanyl)thiazolidine-2,4-dione, 5-[6-(4-Chlorophenyl)hex-5-ynyl]-5-(4-methoxyphenylsulfanyl)thiazolidine-2,4-dione, 5-[11-(4-Chlorophenyl)undec-10-ynyl]-5-(4-methoxyphenylsulfanyl)thiazolidine-2,4-dione, 5-(4-Methoxyphenylsulfanyl)-5-(5-thiophen-2-yl-pent-4-ynyl) thiazolidine-2,4-dione, 5-[5-(4-Chlorophenyl)pent-4-ynyl]-5-(4-fluorophenylsulfanyl) thiazolidine-2,4-dione, 5-[5-(4-Chlorophenyl)pent-4-ynyl]-5-(4-methoxyphenylsulfonyl)thiazolidine-2,4-dione, 5-[6-(4-Chlorophenyl)hex-5-ynyl]-5-(4-methoxyphenylsulfonyl) thiazolidine-2,4-dione, 5-[11-(4-Chlorophenyl)undec-10-ynyl]-5-(4-methoxyphenylsulfonyl)thiazolidine-2,4-dione,
5-[5-(4-Chlorophenyl)pent-4-ynyl]-5-(4-methoxyphenylsulfonyl)thiazolidine-2,4-dione,
5-[5-(2-Chlorophenyl)pent-4-ynyl]-5-(4-methoxybenzenesulfonyl)thiazolidine-2,4-dione,
5-[5-(3-Chlorophenyl)pent-4-ynyl]-5-(4-methoxybenzenesulfonyl)thiazolidine-2,4-dione,
5-[5-(4-Chlorophenyl)pent-4-ynyl]-5-(p-tolylsulfonyl)thiazolidine-2,4-dione,
5-[5-(4-Chlorophenyl)pent-4-ynyl]-5-(4-iodobenzenesulfonyl)thiazolidine-2,4-dione,
5-[5-(4-Chlorophenyl)pent-4-ynyl]-5-(4-fluorobenzenesulfonyl)thiazolidine-2,4-dione,
5-[5-(4-Chlorophenyl)pent-4-ynyl]-5-(4-phenoxybenzenesulfonyl)thiazolidine-2,4-dione,
5-[5-(4-Chlorophenyl)pent-4-ynyl]-5-(naphthalene-2-sulfonyl)thiazolidine-2,4-dione,
N-(4-{5-[5-(4-Chlorophenyl)pent-4-ynyl]-2,4-dioxothiazolidine-5-sulfonyl}phenyl)acetamide,
5-[5-(4-Chlorophenyl)pent-4-ynyl]-5-(quinoline-8-sulfonyl)thiazolidine-2,4-dione,
5-[5-(4-Chlorophenyl)pent-4-ynyl]-5-(4-nitrobenzenesulfonyl)thiazolidine-2,4-dione,
5-(4-Benzyloxybenzenesulfonyl)-5-[5-(4-chlorophenyl)pent-4-ynyl]thiazolidine-2,4-dione,
5-(4-Butoxybenzenesulfonyl)-5-[5-(4-chlorophenyl)-pent-4-ynyl]thiazolidine-2,4-dione,
5-[5-(4-Chlorophenyl)pent-4-ynyl]-5-(naphthalene-1-sulfonyl)thiazolidine-2,4-dione,
5-[5-(2,5-Dichloro-phenyl)pent-4-ynyl]-5-(4-methoxy-benzenesulfonyl)thiazolidine-2,4-dione,
5-[5-(2,5-Dichloro-phenyl)pent-4-ynyl]-5-(4-iodobenzenesulfonyl)thiazolidine-2,4-dione,
5-[5-(2,5-Dichlorophenyl)pent-4-ynyl]-5-[4-(pyridin-4-yloxy)benzenesulfonyl]thiazolidine-2,4-dione,
5-[5-(2,4-Dichlorophenyl)pent-4-ynyl]-5-(4-methoxybenzenesulfonyl)thiazolidine-2,4-dione,
5-(4-Methoxybenzenesulfonyl)-5-[5-(3-nitrophenyl)pent-4-ynyl]thiazolidine-2,4-dione,
5-[5-(3-Nitrophenyl)pent-4-ynyl]-5-(4-phenoxybenzenesulfonyl)thiazolidine-2,4-dione,
5-(4-Iodobenzenesulfonyl)-5-[5-(4-nitrophenyl)pent-4-ynyl]thiazolidine-2,4-dione,
5-(4-Methoxybenzene sulfonyl)-5-[5-(4-nitrophenyl)pent-4-ynyl]thiazolidine-2,4-dione,
5-(4-Methoxybenzene sulfonyl)-5-[5-(2-methyl-5-nitrophenyl)pent-4-ynyl]thiazolidine-2,4-dione,
5-(4-Methoxybenzenesulfonyl)-5-[5-(2-methoxy-5-nitrophenyl)pent-4-ynyl]thiazolidine-2,4-dione,
5-[5-(2-Methyl-5-nitrophenyl)pent-4-ynyl]-5-(4-phenoxybenzenesulfonyl)thiazolidine-2,4-dione,
5-(4-Iodobenzenesulfonyl)-5-[5-(2-methyl-5-nitrophenyl)pent-4-ynyl]thiazolidine-2,4-dione,
5-(5-(2-Methyl-5-nitrophenyl)-pent-4-ynyl]-5-(naphthalene-1-sulfonyl)thiazolidine-2,4-dione,
5-[5-(2-Methyl-5-nitrophenyl)pent-4-ynyl]-5-(naphthalene-2-sulfonyl)thiazolidine-2,4-dione,
5-[5-(2-Methyl-4-nitrophenyl)pent-4-ynyl]-5-[4-(pyridin-4-yloxy)-benzenesulfonyl]thiazolidine-2,4-dione,
5-[5-(2-Methyl-4-nitrophenyl)pent-4-ynyl]-5-(4-phenoxybenzenesulfonyl)thiazolidine-2,4-dione,
5-(4-Methoxybenzenesulfonyl)-5-[5-(2-methyl-4-nitrophenyl)-pent-4-ynyl]thiazolidine-2,4-dione,
5-(4-Iodobenzenesulfonyl)-5-[5-(2-methyl-4-nitrophenyl)pent-4-ynyl]thiazolidine-2,4-dione,
5-(4-Methoxybenzenesulfonyl)-5-[5-(2-methoxy-4-nitrophenyl)pent-4-ynyl]thiazolidine-2,4-dione,
5-[5-(3-Fluoro-5-nitrophenyl)pent-4-ynyl]-5-(4-methoxybenzene-sulfonyl)thiazolidine-2,4-dione,
5-[5-(2,5-Dimethylphenyl)pent-4-ynyl]-5-(4-iodobenzenesulfonyl)thiazolidine-2,4-dione,
5-[5-(2,5-Dimethylphenyl)pent-4-ynyl]-5-(4-methoxybenzenesulfonyl)thiazolidine-2,4-dione,
5-[5-(2,4-Dimethylphenyl)pent-4-ynyl]-5-(4-methoxybenzenesulfonyl)thiazolidine-2,4-dione,
5-[5-(2,4-Dimethylphenyl)pent-4-ynyl]-5-(4-iodobenzenesulfonyl)thiazolidine-2,4-dione,
5-[5-(5-Chloro-2-methylphenyl)pent-4-ynyl]-5-(4-methoxybenzenesulfonyl)thiazolidine-2,4-dione,
5-[5-(5-Chloro-2-methylphenyl)pent-4-ynyl]-5-(4-trifluoromethoxybenzenesulfonyl)thiazolidine-2,4-dione,
5-[5-(4-Chloro-2-methylphenyl)pent-4-ynyl]-5-(4-trifluoromethoxy-benzenesulfonyl)thiazolidine-2,4-dione,
5-[5-(4-Chloro-2-methylphenyl)pent-4-ynyl]-5-(4-iodobenzenesulfonyl)thiazolidine-2,4-dione,
5-[5-(4-Chloro-2-methylphenyl)pent-4-ynyl]-5-(4-methoxybenzenesulfonyl)thiazolidine-2,4-dione,
5-[5-(4-Bromo-2-methy-phenyl)pent-4-ynyl]-5-(4-methoxybenzenesulfonyl)thiazolidine-2,4-dione,
5-[5-(4-Bromo-2-methylphenyl)pent-4-ynyl]-5-(4-iodobenzenesulfonyl)thiazolidine-2,4-dione,
(4-{5-[5-(4-Methoxybenzensulfonyl)-2,4-dioxothiazolidin-5-yl]pent-1-ynyl}phenyl)carbamic Acid tert-Butyl Ester,
(3-Chloro-4-{5-[5-(4-methoxybenzene sulfonyl)-2,4-dioxothiazolidin-5-yl]pent-1-ynyl}phenyl)carbamic Acid tert-Butyl Ester,
N-tert-Butyl-3-{5-[5-(4-iodo-benzenesulfonyl)-2,4-dioxothiazol-idin-5-yl]-pent-1-ynyl}-4-methyl-benzamide,
(3-{5-[5-(4-Iodobenzenesulfonyl)-2,4-dioxothiazolidin-5-yl]pent-1-ynyl}-4-methylphenyl)carbamic Acid tert-Butyl Ester,
(4-{5-[5-(4-Methoxybenzenesulfonyl)-2,4-dioxo-thiazolidin-5-yl]pent-1-ynyl}-3-methylphenyl)carbamic Acid tert-Butyl Ester,
(3-{5-[5-(4-Methoxybenzenesulfonyl)-2,4-dioxothiazolidin-5-yl]pent-1-ynyl}-4-methylphenyl)carbamic Acid tert-Butyl Ester,
(4-{5-[5-(4-Methoxybenzenesulfonyl)-2,4-dioxothiazolidin-5-yl]pent-1-ynyl}-3-trifluoromethylphenyl)-carbamic Acid tert-Butyl Ester,
N-tert-Butyl-3-{5-[5-(4-methoxy-benzenesulfonyl)-2,4-dioxothiazolidin-5-yl]pent-1-ynyl}-4-methyl-benzamide,
5-(4-Methoxybenzenesulfonyl)-5-[5-(4-trifluoromethylphenyl)pent-4-ynyl]thiazolidine-2,4-dione,
5-(4-Methoxybenzenesulfonyl)-5-[5-(4-trifluoromethoxyphenyl)pent-4-ynyl]thiazolidine-2,4-dione,
3-{5-[5-(4-Methoxybenzenesulfonyl)-2,4-dioxothiazolidin-5-yl]pent-1-ynyl}-4-methylbenzoic Acid Methyl Ester, 5-[5-(4-tert-Butylphenyl)pent-4-ynyl]-5-(4-methoxybenzenesulfonyl)thiazolidine-2,4-dione, 5-[5-(4-tert-Butylphenyl)pent-4-ynyl]-5-(toluene-4-sulfonyl)thiazolidine-2,4-dione, 4-{5-[(4-Methoxybenzenesulfonyl)-2,4-dioxo-thiazolidin-5-yl]pent-1-ynyl}benzonitrile, 5-[5-(4-Methanesulfonylphenyl)-pent-4-ynyl]-5-(toluene-4-sulfonyl)thiazolidine-2,4-dione, 4-{5-[5-(4-Methoxybenzenesulfonyl)-2,4-dioxothiazolidin-5-yl]pent-1-ynyl}-3-methylbenzoic Acid Methyl Ester, 5-(4-Methoxybenzenesulfonyl)-5-[5-(4-pyrrol-1-yl-phenyl)pent-4-ynyl]thiazolidine-2,4-dione, 5-(4-Iodo-benzenesulfonyl)-5-[5-(4-pyrrol-1-yl-phenyl)pent-4-ynyl]thiazolidine-2,4-dione, 5-[5-(4-Pyrrol-1-ylphenyl)pent-4-ynyl]-5-(4-trifluoromethoxybenzenesulfonyl)thiazolidine-2,4-dione, 5-(3-Methoxybenzenesulfonyl)-5-(5-thiophen-2-yl-pent-4-ynyl)thiazolidine-2,4-dione, 5-(4-Methylphenylsulfonyl)-5-(5-thiophen-2-yl-pent-4-ynyl)thiazolidine-2,4-dione, 5-(4-Methoxybenzenesulfonyl)-5-(5-thiophen-2-yl-pent-4-ynyl)thiazolidine-2,4-dione, 5-(4-Methoxybenzenesulfonyl)-5-(3-pyridin-3-ylprop-2-ynyl)thiazolidine-2,4-dione, 5-(3-Thiophen-2-yl-prop-2-ynyl)-5-(toluene-4-sulfonyl)thiazolidine-2,4-dione, 5-(3-Biphenyl-4-yl-prop-2-ynyl)-5-(toluene-4-sulfonyl)thiazolidine-2,4-dione, 5-[3-(4-Phenoxyphenyl)prop-2-ynyl]-5-(toluene-4-sulfonyl)thiazolidine-2,4-dione, 5-(3-Biphenyl-4-yl-prop-2-ynyl)-5-(4-methoxybenzenesulfonyl)thiazolidine-2,4-dione, 5-(5-Pyridin-3-yl-pent-4-ynyl)-5-(toluene-4-sulfonyl)thiazolidine-2,4-dione, 5-[5-(5-Amino-2-methylphenyl)pent-4-ynyl]-5-(4-methoxybenzenesulfonyl)thiazolidine-2,4-dione, (3-{5-[5-(4-Methoxybenzenesulfonyl)-2,4-dioxothiazolidin-5-yl]pent-1-ynyl}-4-methylphenyl) carbamic Acid Benzyl Ester, (3-{5-[5-(4-Methoxybenzenesulfonyl)-2,4-dioxothiazolidin-5-yl]pent-1-ynyl}-4-methylphenyl) carbamic Acid 4-Nitro-Benzyl Ester, (3-{5-[5-(4-Methoxybenzenesulfonyl)-2,4-dioxothiazolidin-5-yl]pent-1-ynyl}-4-methylphenyl) carbamic Acid 4-Chloro-phenyl Ester, (3-{5-[5-(4-Methoxybenzenesulfonyl)-2,4-dioxothiazolidin-5-yl]pent-1-ynyl}-4-methylphenyl) carbamic Acid Methyl Ester, (3-{5-[5-(4-Methoxybenzenesulfonyl)-2,4-dioxothiazolidin-5-yl]pent-1-ynyl}-4-methylphenyl) carbamic Acid Isopropyl Ester, (3-{5-[5-(4-Methoxybenzenesulfonyl)-2,4-dioxothiazolidin-5-yl]pent-1-ynyl}-4-methylphenyl) carbamic Acid Neopentyl Ester, (3-{5-[5-(4-Methoxybenzenesulfonyl)-2,4-dioxothiazolidin-5-yl]pent-1-ynyl}-4-methylphenyl) carbamic Acid Butyl Ester, (3-{5-[5-(4-Methoxybenzenesulfonyl)-2,4-dioxothiazolidin-5-yl]pent-1-ynyl}-4-methylphenyl) carbamic Acid Isobutyl, N-[3-(5-{5-[(4-Methoxyphenyl)sulfonyl]-2,4-dioxo-1,3-thiazolidin-5-yl}-1-pentynyl)-4-methylphenyl]-2-methylpropanamide, N-[3-(5-{5-[(4-Methoxyphenyl)sulfonyl]-2,4-dioxo-1,3-thiazolidin-5-yl}-1-pentynyl)-4-methylphenyl]-3,3-dimethylbutanamide, N-[3-(5-{5-[(4-Methoxyphenyl)sulfonyl]-2,4-dioxo-1,3-thiazolidin-5-yl}-1-pentynyl)-4-methylphenyl]-2,2-dimethylpropanamide, N-[3-(5-{5-[(4-Methoxyphenyl)sulfonyl]-2,4-dioxo-1,3-thiazolidin-5-yl}-1-pentynyl)-4-methylphenyl]-2-phenylacetamide, N-Benzyl-N'-[3-(5-{5-[(4-methoxyphenyl)-sulfonyl]-2,4-dioxo-1,3-thiazolidin-5-yl}-1-pentynyl)-4-methylphenyl]urea, N-(4-Methoxyphenyl)-N'-[3-(5-{5-[(4-methoxy phenyl)sulfonyl]-2,4-dioxo-1,3-thiazolidin-5-yl}-1-pentynyl)-4-methylphenyl]urea, N-(4-Chlorophenyl)-N'-[3-(5-{5-[(4-methoxy-phenyl)sulfonyl]-2,4-dioxo-1,3-thiazolidin-5-yl}-1-pentynyl)-4-methylphenyl]urea, N-[3-(5-{5-[(4-Methoxyphenyl)sulfonyl]-2,4-dioxo-1,3-thiazolidin-5-yl}-1-pentynyl)-methylphenyl]-N'-(4-methylphenyl)urea, 4-Chloro-N-[3-(5-{5-[(4-methoxyphenyl)-sulfonyl]-2,4-dioxo-1,3-thiazolidin-5-yl}-1-pentynyl)-4-methylphenyl]benzamide, 4-Methoxy-N-[3-(5-{5-[(4-methoxyphenyl)-sulfonyl]-2,4-dioxo-1,3-thiazolidin-5-yl}-1-pentynyl)-4-methylphenyl]benzamide, N-[3-(5-{5-[(4-Methoxyphenyl)sulfonyl]-2,4-dioxo-1,3-thiazolidin-5-yl}-1-pentynyl)-4-methylphenyl][1,1'-biphenyl]-4-carboxamide, 4-(tert-Butyl)-N-[3-(5-{5-[(4-methoxyphenyl)-sulfonyl]-2,4-dioxo-1,3-thiazolidin-5-yl}-1-pentynyl)-4-methylphenyl]benzamide, 5-[5-(4-Chlorophenyl)-4-pentynyl]-5-[(5-chloro-2-thienyl)sulfonyl]-1,3-thiazolidine-2,4-dione, 5-[5-(4-Chlorophenyl)-4-pentynyl]-5-(2-thienylsulfonyl)-1,3-thiazolidine-2,4-dione, 5-[5-(4-Chlorophenyl)-4-pentynyl]-5-[(3,4-dimethoxyphenyl)sulfonyl]-1,3-thiazolidine-2,4-dione, 5-[5-(4-Chlorophenyl)-4-pentynyl]-5-{[4-(4-pyridinyloxy)phenyl]sulfonyl}-1,3-thiazolidine-2,4-dione, 5-[5-(4-Chlorophenyl)-4-pentynyl]-5-{[5-(2-pyridinyl)-2-thienyl]sulfonyl}-1,3-thiazolidine-2,4-dione, 5-[(5-Chloro-2-thienyl)sulfonyl]-5-[5-(2,5-dichlorophenyl)-4-pentynyl]-1,3-thiazolidine-2,4-dione, 5-[5-(2,5-Dichlorophenyl)-4-pentynyl]-5-(2-thienylsulfonyl)-1,3-thiazolidine-2,4-dione, 5-[5-(2,5-Dichlorophenyl)-4-pentynyl]-5-[(3,4-dimethoxyphenyl)sulfonyl]-1,3-thiazolidine-2,4-dione, 5-[5-(2,5-Dichlorophenyl)-4-pentynyl]-5-{[4-(4-pyridinyloxy)phenyl]sulfonyl}1,3-thiazolidine-2,4-dione, 5-[5-(2,5-Dichlorophenyl)-4-pentynyl]-5-{[5-(2-pyridinyl)-2-thienyl]sulfonyl}-1,3-thiazolidine-2,4-dione, tert-Butyl 3-(5-{5-[(5-chloro-2-thienyl)-sulfonyl]-2,4-dioxo-1,3-thiazolidin-5-yl}-1-pentynyl)-4-methylphenylcarbamate, tert-Butyl 3-{5-[2,4-dioxo-5-(2-thienyl-sulfonyl)-1,3-thiazolidin-5-yl]-1-pentyn-yl}-4-methylphenylcarbamate, tert-Butyl 3-(5-{5-[(3,4-dimethoxy-phenyl)sulfonyl]-2,4-dioxo-1,3-thiazolidin-5-yl}-1-pentynyl)-4-methylphenyl-carbamate, tert-Butyl 3-[5-(2,4-dioxo-5-{[4-(4-pyridinyloxy)phenyl]sulfonyl}-1,3-thiazolidin-5yl)-1-pentynyl]-4-methylphenyl-carbamate, tert-Butyl 3-[5-(2,4-dioxo-5-{[5-(2-pyrid-inyl)-2-thienyl]sulfonyl}-1,3-thiazolidine-5-yl)-1-pentynyl]-4-methylphenyl-carbamate, N-(tert-Butyl)-3-(5-{5-[(5-chloro-2-thienyl)sulfonyl]-2,4-dioxo-1,3-thiazolidin-5-yl}-1-pentynyl)-4-methylbenzamide, N-(tert-Butyl)-3-{5-[2,4-dioxo-5-(2-thienylsulfonyl)-1,3-thiazolidin-5-yl]-1-pentynyl}-4-methylbenzamide, N-(tert-Butyl)-3-(5-{5-[(3,4-dimethoxyphenyl)sulfonyl]-2,4-dioxo-1,3-thiazolidin-5-yl}-1-pentynyl)-4-methylbenzamide, N-(tert-Butyl)-3-[5-(2,4-dioxo-5-{[5-(2-pyridinyl)-2-thienyl]sulfonyl}-1,3-thiazolidin-5-yl)-1-pentynyl]-4-methylbenzamide, 4-{5-[5-(4-Methoxybenzenesulfonyl)-2,4-dioxothiazolidin-5-yl]pent-1-ynyl}-3-methylbenzoic Acid, N-(4-Chlorobenzyl)-3-[5-(4-methoxybenzenesulfonyl)-2,4-dioxo-thiazolidin-4-yl]propionamide, N-[2-(4-Chlorophenyl)ethyl]-3-[5-(4-methoxybenzenesulfonyl)-2,4-dioxo-thiazolidin-5-yl]propionamide, 5-[(4Z)-5-(4-Chloro-phenyl)pent-4-enyl]-5-(toluene-4-sulfonyl)thiazolidine-2,4-dione, 5-[(4E)-5-(4-Chlorophenyl)pent-4-enyl]-5-(4-methoxybenzenesulfonyl)thiazolidine-2,4-dione, 5-[3-(4-Chlorophenyl)propyl]-5-(4-methoxybenzenesulfonyl) thiazolidine-2,4-dione, 5-[5-(3-Aminophenyl)pent-4-ynyl]-5-(4-methoxybenzenesulfonyl)thiazolidine-2,4-dione, 5-(3-Phenylallyl)-5-(toluene-4-sulfonyl)thiazolidine-2,4-dione, Enantiomer of(3-{5-[5-(4-Methoxybenzene sulfonyl)-2,4-dioxothiazolidin-5-yl]pent-1-ynyl}-4-methylphenyl) carbamic Acid tert-Butyl Ester (less polar), Enantiomer of (3-{5-[5-(4-Methoxybenzene sulfonyl)-2,4-dioxothiazolidin-5-yl]pent-1-ynyl}-4-methylphenyl) carbamic Acid tert-Butyl Ester (more polar), 5-[5-(4-Chlorophenyl)pent-4-ynyl]-5-(4-methoxyphenylsulfinyl)-thiazolidine-2,4-dione, Benzyl 5-[5-(5-{[(benzyloxy)carbonyl]-amino}-2-methylphenyl)pent-4-ynyl]-5-[(4-methoxyphenyl)sulfonyl]-2,4-dioxo-1,3-thiazolidine-3-carboxylate, 4-Nitrobenzyl 5-[(4-methoxyphenyl) sulfonyl]-5-{5-[2-methyl-5-({[(4-nitro benzyl)oxy]carbonyl}amino)phenyl]pent-4-ynyl}-2,4-dioxo-1,3-thiazolidine-3-carboxylate, Methyl 5-(5-{5-[(methoxycarbonyl)amino]-2-methylphenyl}pent-4-ynyl)-5-[(4-methoxyphenyl) sulfonyl]-2,4-dioxo-1,3-thiazolidine-3-carboxylate, Isopropyl 5-(5-{5-[(isopropoxycarbonyl)-amino]-2-methylphenyl}pent-4-ynyl)-5-[(4-methoxyphenyl) sulfonyl]-2,4-dioxo-1,3-thiazolidine-3-carboxylate, Neopentyl 5-[(4-methoxyphenyl)sulfonyl]-5-[5-(2-methyl-5-{[(neopentyloxy)carbonyl]-amino}phenyl)pent-4-ynyl]-2,4-dioxo-1,3-thiazolidine-3-carboxylate, Butyl 5-(5-{5-[(butoxycarbonyl)amino]-2-methylphenyl}pent-4-ynyl)-5-[(4-methoxy -phenyl) sulfonyl]-2,4-dioxo-1,3-thiazolidine-3-carboxylate, Isobutyl 5-(5-{5-[(isobutoxycarbonyl)-amino]-2-methylphenyl}pent-4-ynyl)-5-[(4-methoxyphenyl) sulfonyl]-2,4-dioxo-1,3-thiazolidine-3-carboxylate, 5-[5-(4-Chlorophenyl)pent-4-ynyl]-3-(3-imidazol-1-yl-propyl)-5-(4-methoxybenzenesulfonyl)thiazolidine-2,4-dione, 5-[5-(4-Chlorophenyl)pent-4-ynyl]-5-(4-methoxybenzenesulfonyl)-3-methyl -thiazolidine-2,4-dione, 5-[5-(4-Chlorophenyl)pent-4-ynyl]-3-(2,4-diethoxybenzyl)-5-(toluene-4-sulfonyl)thiazolidine-2,4-dione, 5-[5-(4-Chlorophenyl)pent-4-ynyl]-5-(4-iodobenzenesulfonyl)-3-(4-nitrobenzyl)thiazolidine-2,4-dione, and 5-[5-(2,5-Dichlorophenyl)pent-4-ynyl]-5-(4-methoxybenzenesulfonyl)-2,4-dioxothiazolidine-3-carboxylic acid 2-methoxy ethyl ester.

31. A process for the preparation of a compound of Formula (I):

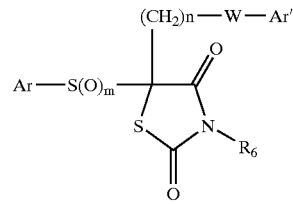

wherein:

Ar is 1-naphthyl, 2-naphthyl, 8-quinolinyl, 2-thienyl, 5-chloro-2-thienyl, 5-(2-pyridyl)-2-thienyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-benzo-[b]-thienyl or a moiety of the formula:

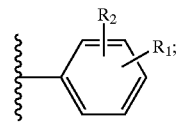

$R_1$ is hydrogen, fluoro, bromo, chloro, iodo, alkyl of 1 to 6 carbon atoms, alkoxy of 1 to 6 carbon atoms, 4-pyridyloxy, azido, nitro, acetamido, trifluoromethoxy, phenoxy, or benzyloxy;

$R_2$ is hydrogen, fluoro, bromo, chloro, iodo, alkyl of 1 to 6 carbon atoms, alkoxy of 1 to 6 carbon atoms, trifluoromethoxy, phenoxy, or benzyloxy;

m is 0, 1 or 2;

$R_6$ is hydrogen;

Y is 2-methoxyethyl, alkyl is 1 to 6 carbon atoms, benzyl, or substituted benzyl;

W is

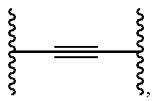

E— and Z——CH=CH—, —CONH—, —CONHCH$_2$—, —CONHCH$_2$CH$_2$— or —CH$_2$—CH$_2$—;

n is an integer of 1 to 9;

Ar' is thienyl, pyridinyl or a moiety of the formula:

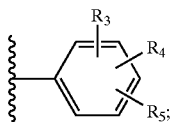

$R_3$, $R_4$, $R_5$, are independently selected from hydrogen, alkoxy of 1 to 6 carbon atoms, alkyl of 1 to 6 carbon atoms, fluoro, bromo, chloro, iodo, nitro, amino, hydroxy, azido, cyano, phenyl, phenoxy, trifluoromethyl, trifluoromethoxy, methanesulphonyl, 1-pyrrolyl, —CO$_2$R$_7$, —CONHR$_8$, —CH$_2$CONHR$_9$, —NHCO$_2$R$_{10}$, —NHCOR$_{11}$, and —NHCONHR$_{12}$;

$R_7$ is selected from H, and alkyl of 1 to 6 carbon atoms, $R_8$ is selected from H, and alkyl of 1 to 6 carbon atoms;

$R_9$ is selected from H, and alkyl of 1 to 6 carbon atoms;

$R_{10}$ is selected from alkyl of 1 to 6 carbon atoms, benzyl, nitrobenzyl, and chlorophenyl;

$R_{11}$ is selected from alkyl of 1 to 6 carbon atoms, benzyl, phenyl, halophenyl, alkyl(1 to 6 carbon atoms)phenyl, alkoxy(1 to 6 carbon atoms)phenyl, and biphenyl;

$R_{12}$ is benzyl, alkyl of 1 to 6 carbon atoms, alkoxy(1 to 6 carbon atoms)phenyl, halophenyl, and alkyl(1 to 6 carbon atoms)phenyl;

provided that when W is

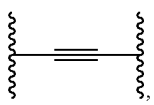

then n is other than 2;

further provided that when n is 1, m is 0 or 2, $R_6$ is H and

W is

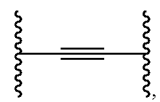

then:

Ar is not phenyl, 2-naphthyl, alkyl substituted phenyl, alkoxy substituted phenyl, halogen substituted phenyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, 2-benzo-[b]-thienyl; and Ar' is not phenyl, alkyl substituted phenyl, perfluoroalkyl (mono or di)substituted phenyl, halogen substituted phenyl, alkoxy substituted phenyl, perfluoroalkoxy substituted phenyl and alkylthio substituted phenyl;

or pharmaceutically acceptable salts thereof, which comprises:

reacting a compound of the formula:

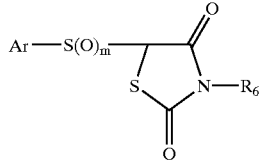

with an alkyne of the formula:

wherein LG is a leaving group, in the presence of a base to give a compound of Formula (I) or a pharmaceutically acceptable salt thereof.

32. The process according to claim 31 wherein the base is selected from alkali metal hydrides, alkali metal alkyls and alkali metal amide bases.

33. The process according to claim 32 wherein the alkali metal hydride is sodium hydride.

34. The process according to claim 32 wherein the alkali metal alkyl is butyl lithium.

35. The process according to claim 32 wherein the alkali metal amide base is selected from lithium diisopropylamide and lithium bis(trimethylsilyl)amide.

36. The process according to claim 31 wherein the leaving group is p-toluenesulfonyloxy.

* * * * *

UNITED STATES PATENT AND TRADEMARK OFFICE
CERTIFICATE OF CORRECTION

PATENT NO. : 6,784,184 B2
DATED : August 31, 2004
INVENTOR(S) : Joseph William Epstein et al.

It is certified that error appears in the above-identified patent and that said Letters Patent is hereby corrected as shown below:

Column 62,
Line 22, delete "4-(5-[5-(4-Methoxybenzenesulfonyl)-2,4-dioxothiazolidin-5-yl]pent-1-ynyl)-3-methylbenzoic Acid Methyl Ester" and insert -- 4-{5-[-(4-Methoxybenzenesulfonyl)-2,4-dioxothiazolidin-5-yl]pent-1-ynyl}-3-methylbenzoic Acid Methyl Ester --

Column 63,
Line 35, delete "N-[3-(5-{5-[(4-Methoxyphenyl)sulfonyl-2,4-dioxo-1,3-thiazolidin-5-yl}-1-pentynyl)-methytphenyl]-N'(4-methylphenyl)urea" and insert -- N-[3-(5-{5-[(4-Methoxyphenyl)sulfonyl]-2,4-dioxo-1,3-thiazolidin-5-yl}-1-pentynyl)-methylpheny]-N'-(4-methylphenyl)urea --
Line 57, delete "tert-Butyl 3-[5-(2,4-dioxo-5-{[5-(2 pyridinyl)-2-thienyl]sulfonyl}-1,3-thlazolidin-l-pentynyl)-4-methylphenylcarbamate" and insert -- tert-Butyl 3-[5-(2,4-dioxo-5-{[5-(2 pyridinyl)-2-thienyl]sulfonyl}-1,3-thiazolidin-5-yl)-1-pentynyl]-4-methylphenylcarbamate --

Column 64,
Line 33, delete "5-[5-(2,5-Dichlorophenyl)-4-pentynyl]-5-{[4-(4-pyridinyloxy)phenyl]sulfonyl}-3-thiazolidine-2,4-dione" and insert -- 5-[5-(2,5-Dichlorophenyl)-4-pentynyl]-5-{[4-(4-pyridinyloxy)phenyl]sulfonyl}-1,3-thiazolidine-2,4-dione --

Column 69,
Line 58, delete "5-(5-(2-Methyl-5-nitrophenyl)-pent-4-ynyl]-5-(naphthalene-1-sulfonyl)thiazolidine-2,4-dione" and insert -- 5-[5-(2-Methyl-5-nitrophenyl)-pent-4-ynyl]-5-(naphthalene-l-sulfonyl)thiazolidine-2,4-dione --

Signed and Sealed this

Eleventh Day of January, 2005

JON W. DUDAS
*Director of the United States Patent and Trademark Office*